(12) United States Patent
Glynias et al.

(10) Patent No.: US 10,460,830 B2
(45) Date of Patent: Oct. 29, 2019

(54) COMPUTER-BASED SYSTEMS AND METHODS FOR ANALYZING GENOMES BASED ON DISCRETE DATA STRUCTURES CORRESPONDING TO GENETIC VARIANTS THEREIN

(71) Applicant: GenomOncology, LLC, Cleveland, OH (US)

(72) Inventors: Manuel J. Glynias, Westlake, OH (US); Ian T. Maurer, Lakewood, OH (US)

(73) Assignee: GENOMONCOLOGY, LLC, Cleveland, OH (US)

( * ) Notice: Subject to any disclaimer, the term of this patent is extended or adjusted under 35 U.S.C. 154(b) by 1341 days.

(21) Appl. No.: 14/465,599

(22) Filed: Aug. 21, 2014

(65) Prior Publication Data

US 2015/0073719 A1    Mar. 12, 2015

Related U.S. Application Data

(60) Provisional application No. 61/869,002, filed on Aug. 22, 2013.

(51) Int. Cl.
*G16B 40/00* (2019.01)
*G16B 30/00* (2019.01)
*G16B 50/00* (2019.01)
*G01N 33/53* (2006.01)
*G16B 20/00* (2019.01)

(52) U.S. Cl.
CPC ......... *G16B 40/00* (2019.02); *G01N 33/5308* (2013.01); *G16B 30/00* (2019.02); *G16B 50/00* (2019.02)

(58) Field of Classification Search
CPC .......... G06F 19/24; G06F 19/22; G06F 19/28; G01N 33/5308
See application file for complete search history.

(56) References Cited

U.S. PATENT DOCUMENTS

| | | |
|---|---|---|
| 6,741,986 B2 | 5/2004 | Cho et al. |
| 7,577,683 B2 | 8/2009 | Cho et al. |
| 7,584,058 B2 | 9/2009 | Zabeau et al. |
| 7,650,339 B2 | 1/2010 | Cho et al. |
| 7,657,383 B2 | 2/2010 | Allard et al. |
| 7,756,873 B2 | 7/2010 | Gould et al. |
| 7,865,534 B2 | 1/2011 | Chandra et al. |
| 8,340,914 B2 | 12/2012 | Gatewood et al. |
| 8,392,353 B2 | 3/2013 | Cho et al. |
| 2002/0120602 A1 | 8/2002 | Overbeek et al. |
| 2003/0220820 A1 | 11/2003 | Sears et al. |
| 2005/0136457 A1 | 6/2005 | Sugiyama et al. |
| 2005/0158742 A1 | 7/2005 | Sugiyama et al. |
| 2007/0027630 A1* | 2/2007 | Sanchez ................ G06F 19/28 702/19 |
| 2007/0178473 A1 | 8/2007 | Chen et al. |
| 2008/0125978 A1 | 5/2008 | Robson et al. |
| 2010/0161607 A1 | 6/2010 | Singh et al. |
| 2011/0191286 A1 | 8/2011 | Cho et al. |
| 2011/0196872 A1 | 8/2011 | Sims et al. |

FOREIGN PATENT DOCUMENTS

| | | | |
|---|---|---|---|
| EP | 1387292 A1 * | 2/2004 | ....... G06F 17/30949 |
| EP | 1387292 | 4/2004 | |
| EP | 2133829 | 12/2009 | |
| WO | 01/06358 | 1/2001 | |
| WO | 12/098515 | 7/2012 | |

OTHER PUBLICATIONS

Brandon et al. (Bioinfornnatics (2009) vol. 25, No. 14:1731-1738).*
O'Connor et al. (BMC Bioinformatics (2010) vol. 11 (Suppl 12):epp. 1-9).*
International Searching Authority, PCT Written Opinion for the International Searching Authority for PCT/US2014/052138, 5 pages (dated Dec. 2, 2014).
The 1000 Genomes Project Consortium, "An integrated map of genetic variation from 1,092 human genomes," Nature, 491: 56-65 (Nov. 1, 2012).
The 1000 Genomes Project Consortium, "An integrated map of genetic variation from 1,092 human genomes: Supplementary Material," pp. 1-113 (Nov. 1, 2012).
Bray et al., eds., "Extensible Markup Language (XML) 1.0 (Fifth Edition); W3C Recommendation Nov. 26, 2008," retrieved from the Internet at URL: http://www.23.org/TR/2008/REC-xml-20081126/, 63 pages (retrieved on Apr. 26, 2013).
Carlson et al., "Apache Lucene-Query Parser Syntax," The Apache Software Foundation, retrieved from the Internet at URL: http://lucene.apache.org/core/old_versioned_docs/versions/2_9_1/queryparsersyntax.html, pp. 1-7 (2006).
CLC Bio, "IBM and CLC bio deliver combined turnkey genomics sequencing analytics solution," retrieved from the Internet at URL: http://www.clcbio.com/wp-content/uploads/2013/04/IBM-and-CLC-bio-deliver-combined-turnkey-genomics-sequencing-analytics-solution1.pdf, 2 pages (Apr. 9, 2013).

(Continued)

*Primary Examiner* — Lori A. Clow
(74) *Attorney, Agent, or Firm* — Jones Day

(57) ABSTRACT

A computer-based method for analyzing genetic variants within a plurality of genomes includes submitting a query term to a database storing a plurality of discrete data structures within a memory. Each data structure can uniquely correspond to only one of the genetic variants present within the plurality of genomes, and can include a first data field comprising a unique alphanumeric identifier for the corresponding genetic variant and a second data field comprising a unique alphanumeric identifier for a genome in which the corresponding genetic variant is present. The query term can include a unique alphanumeric identifier for at least one genome and an operation to be performed. The method further can include searching the second data fields of the plurality of data structures stored in the database for matches to the query term that satisfy the operation; and generating an output representing the search result.

22 Claims, 41 Drawing Sheets

Specification includes a Sequence Listing.

(56) References Cited

OTHER PUBLICATIONS

Danecek et al., "The variant call format and VCFtools," Bioinformatics, 27(15):2156-2158 (2011).
Ng et al., "SIFT: predicting amino acid changes that affect protein function," Nucleic Acids Research, 31(13):3 812-3814 (2003).
International Searching Authority, PCT International Search Report for PCT/US2014/052138, 4 pages (dated Dec. 2, 2014).
1000 Genomes, "1000 Genomes: A Deep Catalog of Human Genetic Variation," retrieved from the Internet at URL: www.1000genomes.org/wiki/Analysis/Variant%20Call%20Format/vcf-cariant-call-f . . . , 15 pages (retrieved on Apr. 19, 2013).
Broad Institute, "File Formats," retrieved from the Internet at URL: http://www.broadinstitute.org/igv/book/export/html/16, 18 pages (retrieved on May 21, 2013).
NCBI→BLAST, "Web BLAST page options," retrieved from the Internet at URL: http://blast.ncbi.nlm.nih.gov/blastcgihelp.shtml, 15 pages (retrieved on May 30, 2013).

\* cited by examiner

G1, C1: [c t a g a t a g g c t a a g a a a a c a t c ...g]
G2, C1: [c t a g c t a g g c t a a g a a a a c a t c ...g]
Gref, C1: [c t a g a t a g g c t a a g a a a a c c a t ...g]
         5                                    20-22
FIG. 1A
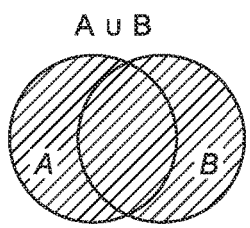
FIG. 1B
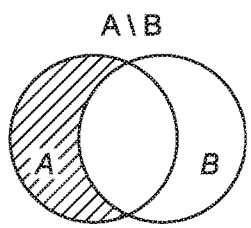
FIG. 1C
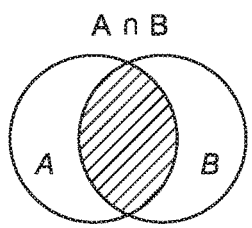
FIG. 1D
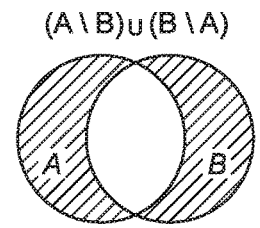
FIG. 1E
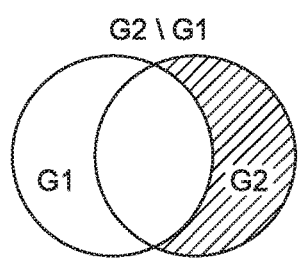
FIG. 1F
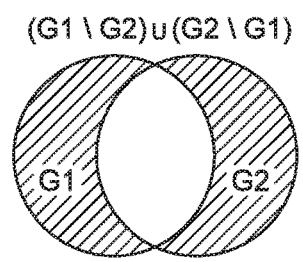
FIG. 1G
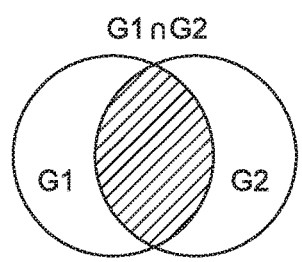
FIG. 1H

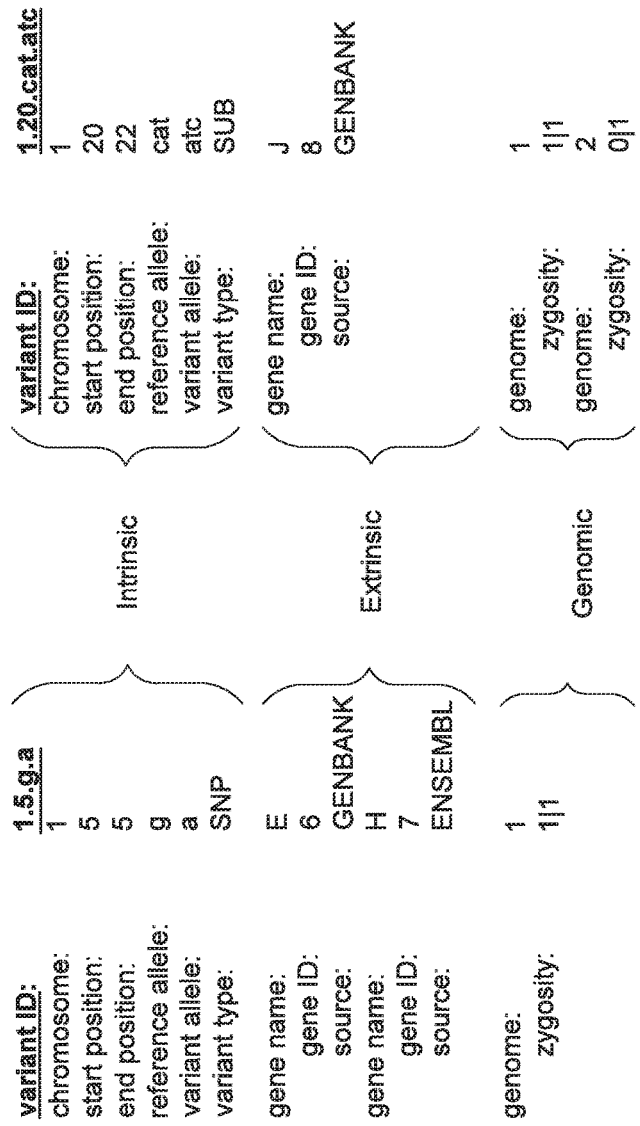

G1,C1: [ctagataggctaagaaacatc...g]
G1,C2: [actgataaacgatccccttcta...c]

G1,CX: [taggcccattgacaatgcgaga...a]

GN,C1: [ctagctaggctaagaaacatc...g]
GN,C2: [actgataaaacgatccccttcta...c]

GN,CX: [taggcccattgagaatgcgaga...a]

| #Chrom | Pos | Ref | Alt | Format |
|---|---|---|---|---|
| 1 | 5 | g | a | 1/1 |
| 1 | 20 | cat | atc | 0/1 |
| ... | | | | |
| X | 13 | g | c | 1/1 |

GN:

| #Chrom | Pos | Ref | Alt | Format |
|---|---|---|---|---|
| 1 | 5 | g | c | 0/1 |
| 1 | 20 | cat | atc | 0/1 |
| 2 | 6 | t | ta | 1/1 |
| ... | | | | |

FIG. 4B

Variant Data 1
variant ID: 1.5.g.a
chromosome: 1
start position: 5
end position: 5
reference allele: g
alternate allele: a
variant type: SNP

Variant Data 2
variant ID: 1.20.cat.atc
chromosome: 1
start position: 20
end position: 22
reference allele: cat
alternate allele: atc
variant type: SUB

Genome Data 1
variant ID: 1.5.g.a
genome: 1
zygosity: 1|1

*FIG. 5A*

Genome Data 2
variant ID: 1.20.cat.atc
genome: 1
zygosity: 0|1

*FIG. 5B*

Variant Data 4
variant ID: 1.5.g.c
chromosome: 1
start position: 5
end position: 5
reference allele: g
alternate allele: c
variant type: SNP

Genome Data 3
variant ID: 1.20.cat.atc
genome: N
zygosity: 0|1

*FIG. 5C*

Genome Data 4
variant ID: 1.5.g.c
genome: N
zygosity: 1|1

*FIG. 5D*

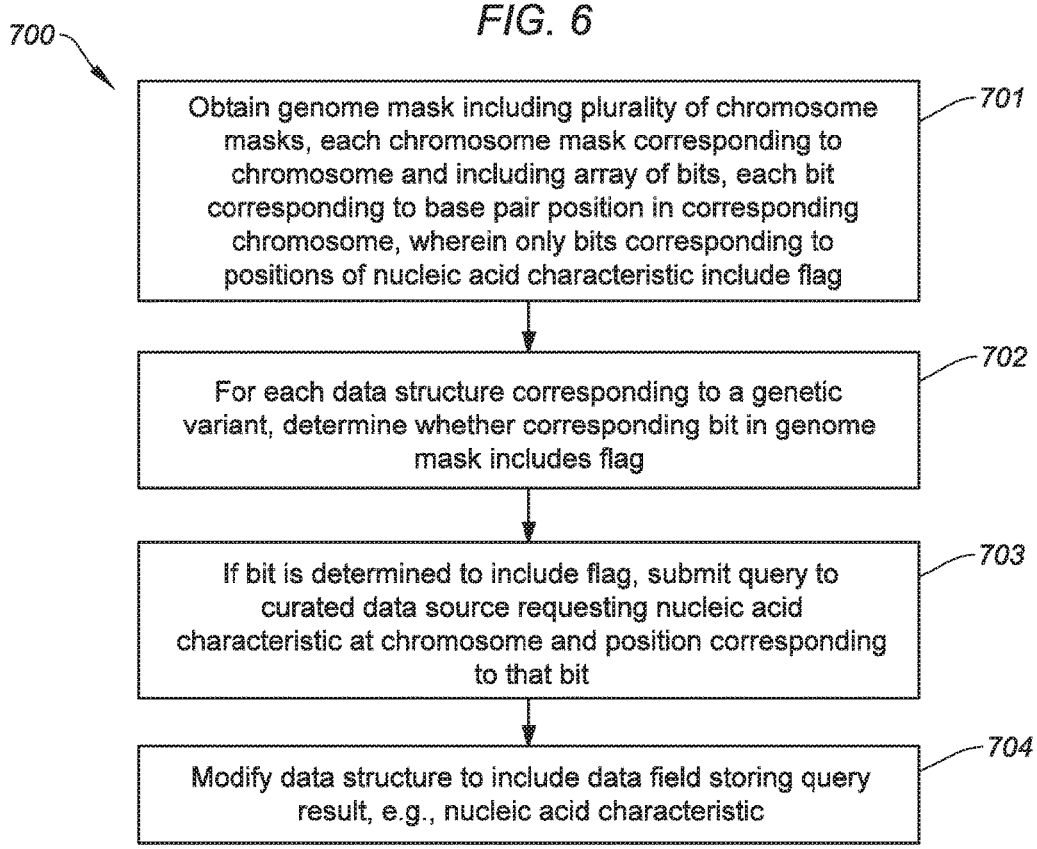

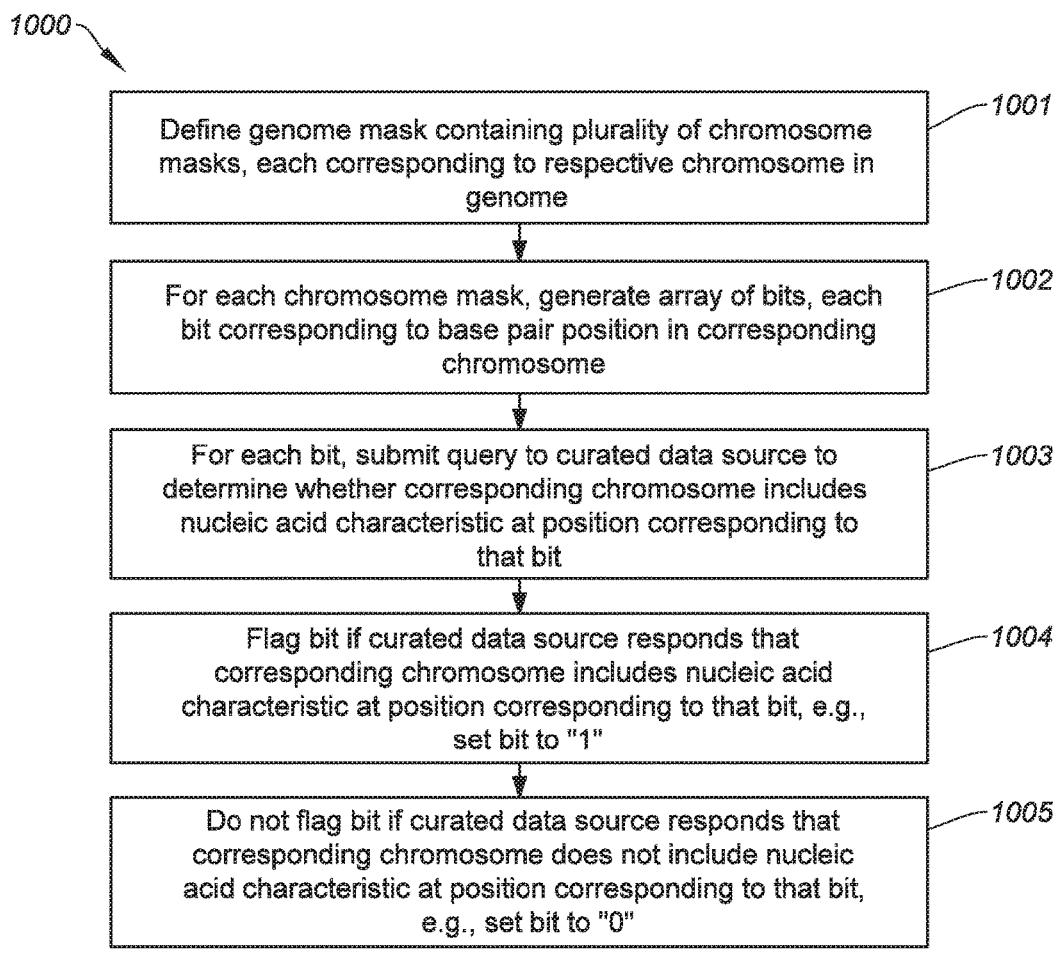

|  |  |  | variant ID: | 1.5.g.a |  |  |
|---|---|---|---|---|---|---|
| chromosome: | 1 | 5' UTR: | efgh | genome: | 1 |
| start position: | 5 | 3' UTR: | ijkl | zygosity: | homozygous |
| end position: | 5 | missense: | no | quality: | 90 |
| reference allele: | g | splice junctions: | no | depth: | 70 |
| alternate allele: | a | CpG islands: | no | phenotype: | breast cancer |
| variant type: | SNP | dbSNP: | yes | clinical: | precancerous |
| gene name: | J | PolyPhen: | yes | genome: | 2 |
| gene ID: | 1234 | PolyPhen-2: | 85 | zygosity: | heterozygous |
| trans. ID: | 4567 | SIFT score: | 45 | quality: | 85 |
| source: | GENBANK | segmental dupl.: | no | depth: | 35 |
| gene name: | EFGH | allele freq.: | 1 | phenotype: | colon cancer |
| gene ID: | 8765 | OMIM: | no | clinical: | stage 4 |
| trans. ID: | 4321 |  |  |  |  |
| source: | ENSEMBL |  |  |  |  |

*FIG. 12*

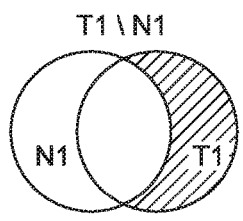
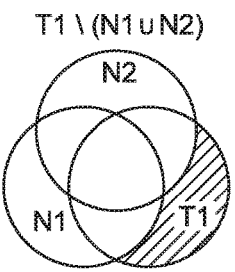
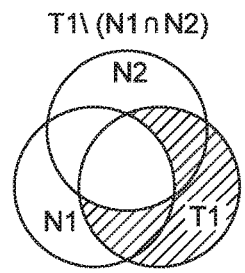

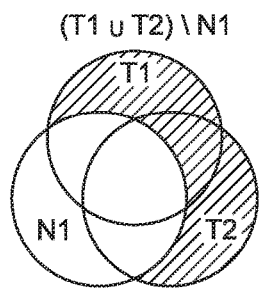
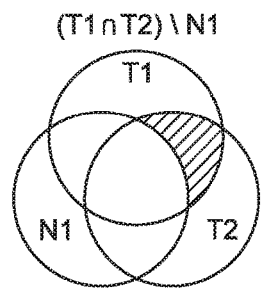

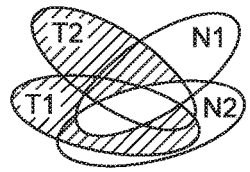
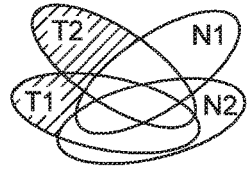
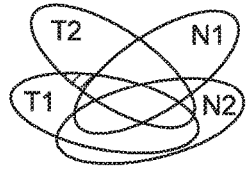
FIG. 13F  FIG. 13G  FIG. 13H
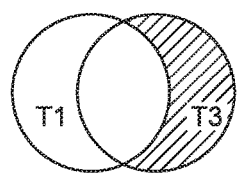
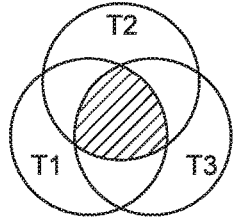
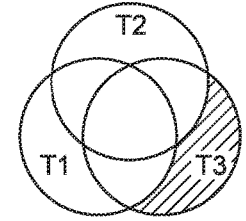
FIG. 13I  FIG. 13J  FIG. 13K
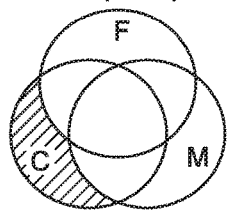
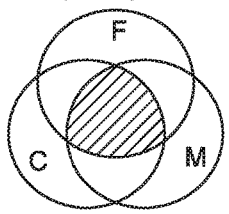
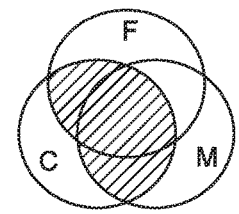
FIG. 13L  FIG. 13M  FIG. 13N
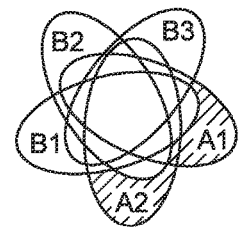
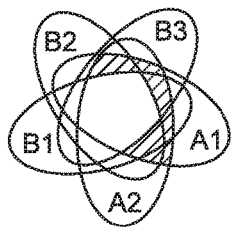
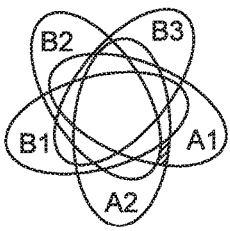
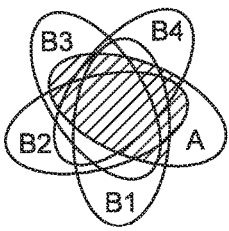
FIG. 13O  FIG. 13P  FIG. 13Q  FIG. 13R

FIG. 15A

Genome Reference Window Preferences Tools Logout
Browse Genomes
3037.interval.V2 & 2 other genomes

| Variations | Chromosomes | CpG islands | lncRNA | Maps | Genes | GO | Pathways | Report | Summary |

☐ Zygosity (○Hom ○Het)  ☐ Quality(edit)  ☐ Depth(edit)  ☐ dbSNP(○out○in)  ☐ Allele Freq(edit)  ☐ COSMIC(edit)  ☐ Pathway(edit)  ☐ SIFT(edit)  ☐ Polyphen-2(edit)
☐ Polyphen-2 Score(edit)  ☐ Pfam(edit)  ☐ OMIM(edit)  ☐ Gene Ontology(edit)  ☐ Gene Expr(edit)  ☐ Gene List(edit)  ☐ Segmental Duplication(edit)  ☐ TCGA(edit)  ☐ TCGA Pheno(edit)
☐ ESP6500(edit)

| Chromosomes | Location | Variation Types | Variation Filters | Templates |

Genomes with Variants  ☐ Fewer Than or Equal To 1(33%)  ☐ More Than or Equal To 0(0%)  *1501*

| Genome | N (%) | Chr | Start | End | VT | Ref | Alt | dbSNP | AF | AMR_AF | ASN_AF | AFR_AF | EUR_AF |
|---|---|---|---|---|---|---|---|---|---|---|---|---|---|
| 3037.interval.V2(0|1, q=43) | 1(33%) | 1 | 865665 | 865665 | snp | G | A | rs145442390 | 0 | 0 | 0 | 0 | 0 |
| 3121.interval.V2(0|1, q=3.01) | 1(33%) | 1 | 877563 | 877563 | snp | A | G | - | 0 | 0 | 0 | 0 | 0 |
| 3037.interval.V2(1|1, q=213) | 1(33%) | 1 | 888659 | 888659 | snp | T | A | - | 0 | 0 | 0 | 0 | 0 |
| 3121.interval.V2(1|1, q=222) 3037.interval.V2(1|1, q=222) 924.interval.V2(1|1, q=222) | 3(100%) | 1 | 888659 | 888659 | snp | T | C | rs3748597 | 0.93 | 0.92 | 0.92 | 0.9 | 0.95 |
| 3121.interval.V2(1|1, q=222) 3037.interval.V2(1|1, q=222) | 2(67%) | 1 | 909238 | 909238 | snp | G | C | rs3829740 | 0.74 | 0.67 | 0.89 | 0.81 | 0.61 |
| 3037.interval.V2(0|1, q=78) | 1(33%) | 1 | 909309 | 909309 | snp | T | C | rs3829738 | 0.22 | 0.23 | 0.27 | 0.21 | 0.18 |
| 3037.interval.V2(0|1, q=61) 924.interval.V2(0|1, q=61) | 2(67%) | 1 | 949608 | 949608 | snp | G | A | rs1921 | 0.34 | 0.3 | 0.21 | 0.43 | 0.4 |
| 924.interval.V2(0|1, q=84) | 1(33%) | 1 | 1179802 | 1179802 | snp | C | T | - | 0 | 0 | 0 | 0 | 0 |
| 924.interval.V2(0|1, q=4.77) | 1(33%) | 1 | 1244924 | 1244924 | snp | T | G | - | 0 | 0 | 0 | 0 | 0 |

See Fig. 15B-1 continued

*FIG. 15B-1*

See Fig. 15B-1

| | | | | | | | | |
|---|---|---|---|---|---|---|---|---|
| 3037.interval.V2(i1, q=84.1)<br>924.interval.V2(i1, q=84.1)<br>3121.interval.V2(i1, q=84.1) | 3(100%) | | | | | 0.96 | 0.99 | 0.97 |
| 924.interval.V2(01, q=6.2) | 1(33%) | 1 | 1269554 | snp | T | C | rs307377 | 0.99 0.91 |
| 3037.interval.V2(01, q=13.2) | 1(33%) | 1 | 1275797 | snp | G | C | rs200649758 | 0 0 0 |
| 924.interval.V2(01, q=24) | 1(33%) | 1 | 1290089 | snp | A | G | - | 0 0 0 |
| 3121.interval.V2(01, q=63)<br>3037.interval.V2(01, q=63)<br>924.interval.V2(01, q=63) | 3(100%) | 1 | 1431165 | snp | C | T | rs9792879 | 0.22 0.17 0.3 0.13 |
| 3037.interval.V2(01, q=187)<br>924.interval.V2(01, q=187) | 2(67%) | 1 | 1551927 | snp | T | C | rs7418389 | 0.51 0.57 0.19 0.71 |
| 3037.interval.V2(01, q=12.3) | 1(33%) | 1 | 1599812 | snp | C | T | rs76114385 | 0.55 0.62 0.5 0.47 0.62 |
| | 1(33%) | 1 | 1666175 | snp | C | T | rs61777509 | 0.11 0.15 0.05 0.09 0.14 |

Columns...   1-100 of 12,209

*FIG. 15B-1 continued*

| | | | | | | | | | |
|---|---|---|---|---|---|---|---|---|---|
| Genome Reference Window Preferences Tools Logout | | | | | | | | | |
| Browse Genomes | | | | | | | | | |
| 3037.interval.V2 & 2 other genomes | | | | | | | | | |
| Variations \| Chromosomes \| CpG Islands \| lncRNA \| Maps \| Genes \| GO \| Pathways \| Report \| Summary | | | | | | | | | |
| ☐ Zygosity (○Hom○Het)   ☐ Quality(edit)   ☐ Depth(edit)   ☐ dbSNP(○out○in)   ☐ Allele Freq(edit)   ☐ COSMIC(edit)   ☐ Pathway(edit)   ☐ SIFT(edit)   ☐ Polyphen-2(edit) | | | | | | | | | |
| ☐ Polyphen-2 Score(edit)   ☐ Pfam(edit)   ☐ OMIM(edit)   ☐ Gene Ontology(edit)   ☐ Gene List(edit)   ☐ Segmental Duplication(edit)   ☐ TCGA(edit)   ☐ TCGA Pheno(edit) | | | | | | | | | |
| ☐ ESP6500(edit) | | | | | | | | | |
| | | | Chromosomes | | Location | | Variation Types | Variation Filters | Templates |
| Genomes with Variants | ☐ Fewer Than or Equal To | | 1(33%) ▲▼ | | | ☐ More Than or Equal To | 0(0%) ▲▼ | | 1501 |
| AFR_AF | EUR_AF | In Gene? | In CDS? | Sift | Polyphen-2 | PP2 Score | Pfam | TCGA | |
| 0 | 0 | SAMD11 | R68Q | 0.16 | benign | 0.001 | PF07647 | - | |
| 0 | 0 | SAMD11 | H306R | 0.01 | benign | 0.091 | PF07647 | - | |
| 0 | 0 | NOC2L | I300F | 0.16 | benign | 0.051 | | - | |
| 0.9 | 0.95 | NOC2L | I300V | 1 | benign | 0 | PF03715 | - | |
| 0.81 | 0.61 | PLEKHN1 | R452P | 0.17 | benign | 0 | | - | |
| 0.21 | 0.18 | PLEKHN1 | S476P | 0.21 | benign | 0.002 | | - | |
| 0.43 | 0.4 | ISG15 | S83N | 0.35 | benign | 0.009 | PF00240 | - | |
| 0 | 0 | FAM132A | G85S | 0.06 | benign | 0.069 | | - | |
| 0 | 0 | PUSL1 | C138W | 0.02 | benign | 0.02 | PF01416 | - | |
| See Fig. 15B-2 continued | | | | | | | | | |

FIG. 15B-2

| See Fig. 15B-2 | | | | | | |
|---|---|---|---|---|---|---|
| 0.99 | 0.97 | TAS1R3 | C757R | 1 | benign | 0 | PF01094 | - |
| 0 | 0 | DVL1 | A231G | 0.05 | benign | 0.009 | PF12316 | - |
| 0 | 0 | MXRA8 | S299P | 0.28 | benign | 0.343 | PF07686 | - |
| 0.3 | 0.13 | ATAD3B | P639S | 0 | probably damaging | 0.904 | PF12037 | TCGA-AN-A0XL |
| 0.54 | 0.71 | MIB2 | F15L | 1 | benign | 0 | PF06701 | - |
| 0.47 | 0.62 | SLC35E2B | V312I | 0.64 | benign | 0.076 | PF03151 | - |
| 0.09 | 0.14 | SLC35E2 | R229H | 0.07 | benign | 0.132 | PF00892 | - |

Columns...    1-100 of 12,209

| | | See Fig. 15B-3 |
|---|---|---|
| *605865 TASTE RECEPTOR TYPE 1, MEMBER 3; TAS1R3 ;;T1R3 | | |
| *601365 DISHEVELLED 1; DVL1 ;;DSH, DROSOPHILA, HOMOLOG OF, 1; DVL | - | 1:1399460-1431722 (0.957944), 1:1439903-1470205 (0.957944) |
| *612317 ATPase FAMILY, AAA DOMAIN-CONTAINING, MEMBER 3B; ATAD3B ;;TOB3;; AAA-TOB3;; KIAA1273 | | |
| *611141 MINDBOMB, DROSOPHILA, HOMOLOG OF, 2; MIB2 ;;SKELETROPHIN | - | 1:1598263-1600000 (0.980551053), 1:1664635-1666363 (0.980551053) |
| | - | 1:1664635-1666363 (0.980551053), 1:1598263-1600000 (0.980551053) |
| | | Export... |

*FIG. 15B-3 continued*

| Genome | N (%) | Chr | Start | End | VT | Ref | Alt | dbSNP | AF | AMR_AF | ASN_AF | AFR_AF | EUR_AF |
|---|---|---|---|---|---|---|---|---|---|---|---|---|---|
| 3121.interval.V2(0/1, q=3.01) | 1(33%) | 1 | 877563 | 877563 | snp | A | G | - | 0 | 0 | 0 | 0 | 0 |
| 924.interval.V2(0/1, q=84) | 1(33%) | 1 | 1179802 | 1179602 | snp | C | T | - | 0 | 0 | 0 | 0 | 0 |
| 924.interval.V2(0/1, q=4.77) | 1(33%) | 1 | 1244924 | 1244924 | snp | T | G | - | 0 | 0 | 0 | 0 | 0 |
| 3037.interval.V2(0/1, q=13.2) | 1(33%) | 1 | 1290089 | 1290089 | snp | A | G | - | 0 | 0 | 0 | 0 | 0 |
| 3037.interval.V2(0/1, q=54) | 1(33%) | 1 | 3421853 | 3421853 | snp | C | T | - | 0 | 0 | 0 | 0 | 0 |
| 924.interval.V2(0/1, q=225) | 1(33%) | 1 | 3563259 | 3563259 | snp | G | A | - | 0 | 0 | 0 | 0 | 0 |
| 3121.interval.V2(0/1, q=17.1) | 1(33%) | 1 | 6528240 | 6528240 | snp | G | T | - | 0 | 0 | 0 | 0 | 0 |
| 3037.interval.V2(0/1, q=201) | 1(33%) | 1 | 11319309 | 11319309 | snp | C | T | - | 0 | 0 | 0 | 0 | 0 |

See Fig. 15C-1 continued

FIG. 15C-1

See Fig. 15C-1

| | | | | | | | |
|---|---|---|---|---|---|---|---|
| 924.interval.V2(0\|1, q=106) | 1(33%) | 1 | 11561155 | 11561155 snp | C | T | - | 0 | 0 | 0 | 0 |
| 3037.interval.V2(0\|1, q=225) | 1(33%) | 1 | 11882784 | 11882784 snp | G | A | - | 0 | 0 | 0 | 0 |
| 3037.interval.V2(0\|1, q=154) | 1(33%) | 1 | 12918959 | 12918959 snp | C | G | - | 0 | 0 | 0 | 0 |
| 3037.interval.V2(0\|1, q=125) | 1(33%) | 1 | 17666248 | 17666248 snp | A | T | - | 0 | 0 | 0 | 0 |
| 924.interval.V2(0\|1, q=5,46) | 1(33%) | 1 | 22211047 | 22211047 snp | C | A | - | 0 | 0 | 0 | 0 |
| 3121.interval.V2(0\|1, q=180) | 1(33%) | 1 | 24484104 | 24484104 snp | G | A | - | 0 | 0 | 0 | 0 |

Columns...    1-100 of 496

| EUR_AF | In Gene? | In CDS? | Sift | Polyphen-2 | PP2 Score |
|---|---|---|---|---|---|
| 0 | SAMD11 | H306R | 0.01 | benign | 0.091 |
| 0 | FAM132A | G85S | 0.06 | benign | 0.069 |
| 0 | PUSL1 | C138W | 0.02 | benign | 0.02 |
| 0 | MXRA8 | S299P | 0.28 | benign | 0.343 |
| 0 | MEGF6 | V598M | 0.11 | benign | 0.247 |
| 0 | WRAP73 | R104C | 0.05 | probably damaging | 1 |
| 0 | PLEKHG5 | L942M | 0.02 | possibly damaging | 0.869 |
| 0 | MTOR | R53Q | 0.06 | benign | 0.114 |

1502

See Fig. 15C-2 continued

*FIG. 15C-2*

| | | | | | |
|---|---|---|---|---|---|
| 0 | PTCHD2 | P36S | 0.05 | benign | 0.003 |
| 0 | CLCN6 | A127T | 0.18 | benign | 0.231 |
| 0 | PRAMEF2 | P32R | 0 | probably damaging | 0.994 |
| 0 | PADI4 | T198S | 0.08 | benign | 0.029 |
| 0 | HSPG2 | R543L | 0.26 | benign | 0.148 |
| 0 | IL28RA | S331L | 0 | possibly | 0.511 |

1502

See Fig. 15C-2

Export...

*FIG. 15C-2 continued*

Genome Reference Window Preferences Tools Logout

Browse Genomes 3037.interval.V2 & 2 other genomes

| Variations | Chromosomes | CpG Islands | lncRNA | Maps | Genes | GO | Pathways | Report | Summary |

☑ SNP Gene Variants ☐ StructVar Gene Variants ☐ CNV Gene Variants ☐ LOH Gene Variants ☐ Expression Gene Variants ☐ Methylation Gene Variants Genomes with Variant Genes   ☑ Fewer Than or Equal To  2(67%) ▲▼   ☑ More Than or Equal To  2(67%) ▲▼   *1503*

| Genome | N (%) | Gene Name | Variant Type | Chr | Description | Severity |
|---|---|---|---|---|---|---|
| 3121.interval.V2<br>924.interval.V2 | 2(67%) | DCHS2 (54798) | SNP/Small InDel | 4 | dachsous 2 (Drosophila) | Missense, SIFT<0.1 |
| 924.interval.V2<br>3037.interval.V2 | 2(67%) | SYNE2 (23224) | SNP/Small InDel | 14 | spectrin repeat containing, nuclear envelope 2 | Nonsense |
| 924.interval.V2<br>3121.interval.V2 | 2(67%) | CHST3 (9469) | SNP/Small InDel | 10 | carbohydrate (chondroitin 6) sulfotransferase 3 | Missense, SIFT<0.1 |
| 3121.interval.V2<br>3037.interval.V2 | 2(67%) | FASN (2194) | SNP/Small InDel | 17 | fatty acid synthase | Missense, SIFT<0.1 |
| 924.interval.V2<br>3121.interval.V2 | 2(67%) | APRT (353) | SNP/Small InDel | 16 | adenine phosphoribosyltransferase | Nonsense |
| 3037.interval.V2<br>3121.interval.V2 | 2(67%) | LRWD1 (222229) | SNP/Small InDel | 7 | leucine-rich repeats and WD repeat domain containing 1 | Missense |

See Fig. 15D continued

*FIG. 15D*

See Fig. 15D

| Interval | Count | Gene | Variant Type | Chr | Description | Effect |
|---|---|---|---|---|---|---|
| 3121.interval.V2 / 924.interval.V2 | 2(67%) | ABCA2 (20) | SNP/Small InDel | 9 | ATP-binding cassette, sub-family A (ABC1), member 2 | Missense, SIFT<0.1 |
| 3037.interval.V2 / 924.interval.V2 | 2(67%) | POLD1 (5424) | SNP/Small InDel | 19 | polymerase (DNA directed), delta 1, catalytic subunit | Missense, SIFT<0.1 |
| 924.interval.V2 / 3037.interval.V2 | 2(67%) | CCDC65 (85478) | SNP/Small InDel | 12 | coiled-coil domain containing 65 | Missense, SIFT<0.1 |
| 924.interval.V2 / 3037.interval.V2 | 2(67%) | AMDHD2 (51005) | SNP/Small InDel | 16 | amidohydrolase domain containing 2 | Missense |
| 924.interval.V2 / 3037.interval.V2 | 2(67%) | CELSR2 (1952) | SNP/Small InDel | 1 | cadherin, EGF LAG seven-pass G-type receptor 2 (flamingo homolog, Drosophila) | Missense, SIFT<0.1 |
| 3121.interval.V2 / 3037.interval.V2 | 2(67%) | KCNV2 (169522) | SNP/Small InDel | 9 | potassium channel, subfamily V, member 2 | Missense, SIFT<0.1 |
| 3121.interval.V2 / 3037.interval.V2 | 2(67%) | CELA1 (1990) | SNP/Small InDel | 12 | chymotrypsin-like elastase family, member 1 | Disrupted |
| 3037.interval.V2 / 924.interval.V2 | 2(67%) | HEPH (9843) | SNP/Small InDel | X | hephaestin | Disrupted |
| 3121.interval.V2 / 3037.interval.V2 | 2(67%) | OR1B1 (347169) | SNP/Small InDel | 9 | olfactory receptor, family 1, subfamily B, member 1 | Disrupted |
| 3121.interval.V2 / 3037.interval.V2 | 2(67%) | WHSC1 (7468) | SNP/Small InDel | 4 | Wolf-Hirschhorn syndrome candidate 1 | Disrupted |
| 3037.interval.V2 / 924.interval.V2 | 2(67%) | CLEC18B (497190) | SNP/Small InDel | 16 | C-type lectin domain family 18, member B | Missense, SIFT<0.1 |

| Genome Reference Window Preferences Tools Logout | | | | | |
|---|---|---|---|---|---|
| Browse Genomes | | | | | |
| 3037.interval.V2 & 2 other genomes | | | | | |
| Variations \| Chromosomes \| CpG Islands \| lncRNA \| Maps \| Genes \| GO \| Pathways \| Report \| Summary | | | | | |
| ☑ SNP Gene Variants ☐ StructVar Gene Variants ☐ CNV Gene Variants ☐ LOH Gene Variants ☐ Expression Gene Variants ☐ Methylation Gene Variants | | | | | | _1504_ |
| Genomes with variant Genes | ☐ Fewer Than or Equal To 2(67%) ▲▼ | | ☑ More Than or Equal To ALL ▲▼ | | |
| Genome | N (%) | Gene Name | Variant Type | Chr | Description | Severity |
| 3037.interval.V2 3121.interval.V2 924.interval.V2 | 3(100%) | MAX (4149) | SNP/Small InDel | 14 | MYC associated factor X | Nonsense |
| 3121.interval.V2 3037.interval.V2 924.interval.V2 | 3(100%) | PTCHD3 (374306) | SNP/Small InDel | 10 | patched domain containing 3 | Disrupted |

Genome Reference Window Preferences Tools Logout 924.interval.V2 & 0 other genomes vs 3037.interval.V2 & 3121.interval.V2

| Variations | Chromosomes | CpG Islands | lncRNA | Maps | Genes | GO | Pathways | Report | Summary |

☑1 ☑2 ☑3 ☑4 ☑5 ☑6 ☑7 ☑8 ☑9 ☑10 ☑11 ☑12 ☑13 ☑14 ☑15 ☑16 ☑17 ☑18 ☑19 ☑20 ☑21 ☑22 ☑X ☑Y  [Go To...]

Check All   Uncheck All

| Chromosomes | Location | Variation Types | Variation Filters | Templates |

_1505_

Genomes with Variants

☐ Fewer Than or Equal To [None ▲▼]    ☐ More Than or Equal To [ALL ▲▼]

| Genome | N (%) | Chr | Start | End | VT | Ref | Alt | dbSNP | AF | AMR_AF | ASN_AF | AFR_AF | EUR_AF |
|---|---|---|---|---|---|---|---|---|---|---|---|---|---|
| 3037.interval.V2(0\|1, q=43) | 0(0%) | 1 | 865665 | 865665 | snp | G | A | rs145442390 | 0 | 0 | 0 | 0 | 0 |
| 3121.interval.V2(0\|1, q=3.01) | 0(0%) | 1 | 877563 | 877563 | snp | A | G | - | 0 | 0 | 0 | 0 | 0 |
| 3037.interval.V2(1\|1, q=213) | 0(0%) | 1 | 888659 | 888659 | snp | T | A | - | 0 | 0 | 0 | 0 | 0 |
| 3121.interval.V2(1\|1, q=222) 3037.interval.V2(1\|1, q=213) 924.interval.V2(1\|1, q=222) | 1(100%) | 1 | 888659 | 888659 | snp | T | C | rs3748597 | 0.93 | 0.92 | 0.92 | 0.9 | 0.95 |
| 3121.interval.V2(1\|1, q=222) 3037.interval.V2(0\|1, q=72) | 0(0%) | 1 | 909238 | 909238 | snp | G | C | rs3829740 | 0.74 | 0.67 | 0.89 | 0.81 | 0.61 |
| 3037.interval.V2(0\|1, q=78) | 0(0%) | 1 | 909309 | 909309 | snp | T | C | rs3829738 | 0.22 | 0.23 | 0.27 | 0.21 | 0.18 |
| 3037.interval.V2(0\|1, q=61) | 1(100%) | 1 | 949608 | 949608 | snp | G | A | rs1921 | 0.34 | 0.3 | 0.21 | 0.43 | 0.4 |
| 924.interval.V2(0\|1, q=12A) | 1(100%) | 1 | 1179802 | 1179802 | snp | C | T | - | 0 | 0 | 0 | 0 | 0 |
| 924.interval.V2(0\|1, q=84) | 1(100%) | 1 | 1244924 | 1244924 | snp | T | G | - | 0 | 0 | 0 | 0 | 0 |
| 3037.interval.V2(0\|1, q=84.1) 924.interval.V2(0\|1, q=4.77) | 1(100%) | 1 | 1269554 | 1269554 | snp | T | C | rs307377 | 0.96 | 0.99 | 0.91 | 0.99 | 0.97 |
| 924.interval.V2(1\|1, q=112) 3121.interval.V2(1\|1, q=150) | | | | | | | | | | | | | |

*FIG. 15F-1*

See Fig. 15F-1 continued

See Fig. 15F-1

| | | | | | | | | | | |
|---|---|---|---|---|---|---|---|---|---|---|
| 924.interval.V2(0|,q=6.2) | 1(100%) | 1 | 1275797 | 1275797 | snp | G | C | rs200649758 | 0 | 0 | 0 | 0 |
| 3037.interval.V2(0|,q=13.2) | 0(0%) | 1 | 1290089 | 1290089 | snp | A | G | - | | | | |
| 924.interval.V2(0|,q=24) | 1(100%) | 1 | 1431165 | 1431165 | snp | C | T | rs9792879 | 0.22 | 0.17 | 0.3 | 0.13 |
| 3121.interval.V2(0|,q=63) | | | | | | | | | | | | |
| 3037.interval.V2(1|,q=151) | 1(100%) | 1 | 1551927 | 1551927 | snp | T | C | rs7418389 | 0.51 | 0.57 | 0.19 | 0.71 |
| 924.interval.V2(0|,q=44) | | | | | | | | | | | | |
| 3037.interval.V2(0|,q=187) | 1(100%) | 1 | 1599812 | 1599812 | snp | C | T | rs76114385 | 0.55 | 0.62 | 0.5 | 0.47 | 0.62 |
| 924.interval.V2(0|,q=201) | | | | | | | | | | | | |
| 3037.interval.V2(0|,q=12.3) | 0(0%) | 1 | 1666175 | 1666175 | snp | C | T | rs61777509 | 0.11 | 0.15 | 0.05 | 0.09 | 0.14 |

Columns...

| EUR_AF | In Gene? | In CDS? | Sift | Polyphen-2 | PP2 Score |
|---|---|---|---|---|---|
| 0 | SAMD11 | R68Q | 0.16 | benign | 0.001 |
| 0 | SAMD11 | H306R | 0.01 | benign | 0.091 |
| 0 | NOC2L | I300F | 0.16 | benign | 0.051 |
| 0.95 | NOC2L | I300V | 1 | benign | 0 |
| 0.61 | PLEKHN1 | R452P | 0.17 | benign | 0 |
| 0.18 | PLEKHN1 | S476P | 0.21 | benign | 0.002 |
| 0.4 | ISG15 | S83N | 0.35 | benign | 0.009 |
| 0 | FAM132A | G85S | 0.06 | benign | 0.069 |
| 0 | PUSL1 | C138W | 0.02 | benign | 0.02 |
| 0.97 | TAS1R3 | C757R | 1 | benign | 0 |

1505

See Fig. 15F-2 continued

FIG. 15F-2

| | | | | | See Fig. 15F-2 |
|---|---|---|---|---|---|
| 0 | DVL1 | A231G | 0.05 | benign | 0.009 |
| 0 | MXRA8 | S299P | 0.28 | benign | 0.343 |
| 0.13 | ATAD3B | P639S | 0 | probably damaging | 0.904 |
| 0.71 | MIB2 | F15L | 1 | benign | 0 |
| 0.62 | SLC35E2B | V312I | 0.64 | benign | 0.076 |
| 0.14 | SLC35E2 | R229H | 0.07 | benign | 0.132 |
| | | | | | Export... |

FIG. 15F-2 continued

Genome  Reference  Window  Preferences  Tools  Logout 924.interval.V2 & 0 other genomes vs 3037.interval.V2 & 3121.interval.V2

| Variations | Chromosomes | CpG islands | lncRNA | Maps | Genes | GO | Pathways | Report | Summary |

☑1 ☑2 ☑3 ☑4 ☑5 ☑6 ☑7 ☑8 ☑9 ☑10 ☑11 ☑12 ☑13 ☑14 ☑15 ☑16 ☑17 ☑18 ☑19 ☑20 ☑21 ☑22 ☑X ☑Y   Go To...

Check All / Uncheck All

| Chromosomes | Location | Variation Types | Variation Filters | Templates |

*1506*

Genomes with Variants

☐ Fewer Than or Equal To  None ▲▼      ☑ More Than or Equal To  ALL ▲▼

| Genome | N (%) | Chr | Start | End | VT | Ref | Alt | dbSNP | AF | AMR_AF | ASN_AF | AFR_AF | EUR_AF |
|---|---|---|---|---|---|---|---|---|---|---|---|---|---|
| 924.interval.V2(0\|1, q=84) | 1(100%) | 1 | 1179802 | 1179802 | snp | C | T | - | 0 | 0 | 0 | 0 | 0 |
| 924.interval.V2(0\|1, q=4.77) | 1(100%) | 1 | 1244924 | 1244924 | snp | T | G | - | 0 | 0 | 0 | 0 | 0 |
| 924.interval.V2(0\|1, q=6.2) | 1(100%) | 1 | 1275797 | 1275797 | snp | G | C | rs200649758 | 0 | 0 | 0 | 0 | 0.13 |
| 924.interval.V2(0\|1, q=24) | 1(100%) | 1 | 1431165 | 1431165 | snp | C | T | rs9792879 | 0.22 | 0.17 | 0.3 | 0.3 | 0.18 |
| 924.interval.V2(1\|1, q=222) | 1(100%) | 1 | 1900186 | 1900186 | snp | T | C | rs35269416 | 0.15 | 0.19 | 0.11 | 0.09 | 0.42 |
| 924.interval.V2(1\|1, q=222) | 1(100%) | 1 | 1900232 | 1900232 | snp | T | C | rs16824588 | 0.41 | 0.43 | 0.35 | 0.43 | 0.25 |
| 924.interval.V2(1\|1, q=163) | 1(100%) | 1 | 2938989 | 2938989 | snp | G | A | rs3795263 | 0.16 | 0.16 | 0.17 | 0.01 | 0 |
| 924.interval.V2(0\|1, q=225) | 1(100%) | 1 | 3563259 | 3563259 | snp | G | A | - | 0 | 0 | 0 | 0 | 0.59 |
| 924.interval.V2(1\|1, q=222) | 1(100%) | 1 | 6184092 | 6184092 | snp | A | G | rs2843493 | 0.7 | 0.61 | 0.99 | 0.61 | 0.01 |
| 924.interval.V2(0\|1, q=49) | 1(100%) | 1 | 6310562 | 6310562 | snp | C | G | rs142015102 | 0.0041 | 0.01 | 0 | 0 | 0.99 |
| 924.interval.V2(1\|1, q=18.8) | 1(100%) | 1 | 6614391 | 6614391 | snp | A | C | rs6693391 | 0.96 | 0.98 | 0.98 | 0.86 | 0.01 |
| 924.interval.V2(0\|1, q=59) | 1(100%) | 1 | 7869953 | 7869953 | snp | C | G | rs150812083 | 0.01 | 0.01 | 0 | 0.002 | |

*FIG. 15G-1*

See Fig. 15G-1 continued

See Fig. 15G-1

| | | | | | | | | | | | |
|---|---|---|---|---|---|---|---|---|---|---|---|
| 924.interval.V2(0]1, q=112) | 1(100%) | 1 | 7869960 | 7869960 | snp | A | G | rs139315125 | 0.01 | 0.01 | 0 | 0.002 | 0.01 |
| 924.interval.V2(0]1, q=159) | 1(100%) | 1 | 9165669 | 9165669 | snp | G | A | rs12075362 | 0.03 | 0.02 | 0.0035 | 0.07 | 0.03 |
| 924.interval.V2(0]1, q=225) | 1(100%) | 1 | 10460485 | 10460485 | snp | T | C | rs1049887 | 0.26 | 0.35 | 0.3 | 0.09 | 0.31 |
| 924.interval.V2(0]1, q=106) | 1(100%) | 1 | 11561155 | 11561155 | snp | C | T | - | 0 | 0 | 0 | 0 | 0 |
| 924.interval.V2(0]1, q=104) | 1(100%) | 1 | 11561164 | 11561164 | snp | G | A | rs41274528 | 0.13 | 0.09 | 0.03 | 0.38 | 0.06 |
| 924.interval.V2(0]1, q=68) | 1(100%) | 1 | 11579504 | 11579504 | snp | G | C | rs2072993 | 0.19 | 0.09 | 0.43 | 0.1 | 0.11 |

Columns...    1-100 of 2,269

FIG. 15G-1 continued

| EUR_AF | In Gene? | In CDS? | Sift | Polyphen-2 | PP2 Score |
|---|---|---|---|---|---|
| 0 | FAM132A | G85S | 0.06 | benign | 0.069 |
| 0 | PUSL1 | C138W | 0.02 | benign | 0.02 |
| 0 | DVL1 | A231G | 0.05 | benign | 0.009 |
| 0.13 | ATAD3B | P639S | 0 | probably damaging | 0.904 |
| 0.18 | KIAA1751 | K378R | 0.49 | benign | 0.01 |
| 0.42 | KIAA1751 | I363V | 1 | benign | 0 |
| 0.25 | ACTRT2 | G247R | 0.01 | probably damaging | 0.999 |
| 0 | WRAP73 | R104C | 0.05 | probably damaging | 1 |
| 0.59 | CHD5 | S396P | 0.39 | benign | 0 |
| 0.01 | GPR153 | G368R | 0.83 | benign | 0.003 |
| 0.99 | NOL9 | S58A | 1 | benign | 0 |
| 0.01 | PER3 | P415A | 0 | probably damaging | 0.999 |

See Fig. 15G-2 continued

| | | | | | See Fig. 15G-2 |
|---|---|---|---|---|---|
| 0.01 | PER3 | H417R | 0.01 | benign | |
| 0.03 | GPR157 | A223V | 0.02 | probably damaging | 0.108 |
| 0.31 | PGD | M46T | - | unknown | 0.992 |
| 0 | PTCHD2 | P36S | 0.05 | benign | 0 |
| 0.06 | PTCHD2 | G39R | 0.59 | benign | 0.003 |
| 0.11 | PTCHD2 | G661A | 0.08 | benign | 0.001 |
| | | | | | 0.271 |

[ Export... ]

Genome  Reference  Window  Preferences  Tools  Logout

Browse Genomes
HCC1187_T

| Variations | Chromosomes | CpG Islands | lncRNA | StructVar | Maps | Genes | GO | Pathways | Report | Summary |

☐ Zygosity (○Hom ○Het)    ☐ dbSNP(○out ○in)    ☐ Allele Freq(edit)    ☐ COSMIC(edit)       ☐ Pathway(edit)
☐ Polyphen-2 Score(edit)  ☐ Pfam(edit)   ☐ OMIN(edit)   ☐ Gene Ontology(edit)  ☐ Gene Expr(edit)    ☐ Segmental Duplication(edit)
☐ ESP6500(edit)

| Chromosomes | Location | Variation Types |

1507

| Chr | Start | End | VT | Ref | Alt | Zyg | dbSNP | AF | AMR_AF | ASN_AF | AFR_AF | EUR_AF |
|---|---|---|---|---|---|---|---|---|---|---|---|---|
| 1 | 69511 | 69511 | snp | A | G | 111 | rs75062661 | 0.65 | 0.65 | 0.87 | 0.33 | 0.7 |
| 1 | 69569 | 69569 | snp | T | C | 111 | rs2531267 | 0 | 0 | 0 | 0 | 0 |
| 1 | 888659 | 888659 | snp | T | C | 111 | rs3748597 | 0.93 | 0.92 | 0.92 | 0.9 | 0.95 |
| 1 | 949608 | 949608 | snp | G | A | 111 | rs1921 | 0.34 | 0.3 | 0.21 | 0.43 | 0.4 |
| 1 | 1269554 | 1269554 | snp | T | C | 111 | rs307377 | 0.96 | 0.99 | 0.91 | 0.99 | 0.97 |
| 1 | 1551927 | 1551927 | snp | T | C | 111 | rs7418389 | 0.51 | 0.57 | 0.19 | 0.54 | 0.71 |
| 1 | 1599812 | 1599812 | snp | C | T | 111 | rs76114385 | 0.55 | 0.62 | 0.5 | 0.47 | 0.62 |
| 1 | 1666251 | 1666251 | snp | G | A | 011 | rs77655487 | 0 | 0 | 0 | 0 | 0 |
| 1 | 1849529 | 1849529 | snp | A | G | 111 | rs28640257 | 0.39 | 0.51 | 0.45 | 0.07 | 0.49 |
| 1 | 1887019 | 1887019 | snp | A | G | 111 | rs28548017 | 0.81 | 0.83 | 0.86 | 0.73 | 0.82 |

See Fig. 15H-1 continued

See Fig. 15H-1

| | | | | | | | | | |
|---|---|---|---|---|---|---|---|---|---|
| 1 | 3328358 | 3328358 | snp | T | C | 111 | rs870124 | 0.93 | 0.87 | 1 | 0.99 | 0.86 |
| 1 | 3389727 | 3389727 | snp | C | T | 111 | rs2185639 | 0.69 | 0.73 | 0.69 | 0.38 | 0.88 |
| 1 | 3428608 | 3428608 | snp | G | A | 111 | rs11585362 | 0.28 | 0.23 | 0.41 | 0.36 | 0.14 |
| 1 | 3496479 | 3496479 | snp | T | C | 111 | rs2794340 | 0.85 | 0.92 | 0.68 | 0.88 | 0.91 |
| 1 | 3548832 | 3548832 | snp | G | C | 111 | rs2760320 | 0.04 | 0.12 | 0 | 0.03 | 0.05 |
| 1 | 3807593 | 3807593 | snp | G | C | 111 | rs4274008 | 1 | 1 | 1 | 1 | 0.99 |
| 1 | 6184092 | 6184092 | snp | A | G | 111 | rs2843493 | 0.7 | 0.61 | 0.99 | 0.61 | 0.59 |

Columns...

☐ SiFT(edit)    ☐ Polyphen-2(edit)
☐ TCGA(edit)    ☐ TCGA Pheno(edit)
                                      Go To...

| Variation Types | Variation Filters | Templates |

*1507*

| EUR_AF | In Gene? | In CDS? | Sift | Polyphen-2 | PP2 Score | Pfam | TCGA | OMIM |
|---|---|---|---|---|---|---|---|---|
| 0.7 | OR4F5 | T141A | 0.66 | benign | 0 | PF00001 | - | - |
| 0 | OR4F5 | L160P | 1 | benign | 0 | PF00001 | - | - |
| 0.95 | NOC2L | I300V | 1 | benign | 0 | PF03715 | - | *610770 NUCLE CEREVISIAE, H |
| 0.4 | ISG15 | S83N | 0.35 | benign | 0.009 | PF00240 | - | *147571 UBIQU PROTEIN IFI-15 |
| 0.97 | TAS1R3 | C757R | 1 | benign | 0 | PF01094 | - | *605865 TASTE |
| 0.71 | MIB2 | F15L | 1 | benign | 0 | PF06701 | - | *611141 MINDB ::SKELETROPH |
| 0.62 | SLC35E2B | V312I | 0.64 | benign | 0.076 | PF03151 | - | - |
| 0 | SLC35E2 | R204W | 0.09 | benign | 0 | PF00892 | - | - |
| 0.49 | TMEM52 | M126T | 0.12 | benign | 0.011 | - | TCGA-A8-A09M | - |
| 0.82 | KIAA1751 | X763Q | - | unknown | - | - | - | - |

*FIG. 15H-2*

See Fig. 15H-2 continued

| | | | | | | See Fig. 15H-2 |
|---|---|---|---|---|---|---|
| 0.86 | PRDM16 | S534P | 0.63 | benign | 0 | PF00096 | - | *605557 PR DO GENE 1; MEL 1 |
| 0.88 | ARHGEF16 | H82Y | 0.57 | benign | 0.044 | PF00621 | - | - |
| 0.14 | MEGF6 | A208V | 0.04 | benign | 0.201 | PF07645 | - | **604266 MULTI MEGF6 ::EPIDE FORMERLY |
| 0.91 | MEGF6 | S131G | 1 | benign | 0 | PF00053 | - | **604266 MULTI MEGF6 ::EPIDE FORMERLY |
| 0.05 | WRAP73 | I331M | 0.27 | benign | 0.086 | PF00400 | - | *606040 WD RE |
| 0.99 | C1orf174 | T53R | 1 | benign | 0 | - | - | - |
| 0.59 | CHD5 | S396P | 0.39 | benign | 0 | PF08074 | - | *610771 CHRO |

Export...

*FIG. 15H-2 continued*

Genome Reference Window Preferences Tools Logout

Browse Genomes

HCC1187_T

| Variations | Chromosomes | CpG Islands | ncRNA | StructVar | Maps | Genes | GO | Pathways | Report | Summary |

☐ COSMIC(edit)    ☐ Pathway(edit)
☐ Gene Expr(edit)    ☑ Gene List(edit)    ☐ Segmental Duplication(edit)

| Chromosomes | Location | Variation Types |

Parameters for Gene List Filter

Filter using gene names in: WashU-GPS-CancerPanel.txt    *1508*

| Name | Description |
|---|---|
| ProstateCancerSet.txt | |
| WashU-GPS-OvarianCancerSet.txt | |
| WashU-GPS-MyeloidDisorderSet.txt | |
| WashU-GPS-MelanomaSet.txt | |
| WashU-GPS-LungCancerSet.txt | |
| WashU-GPS-GIStromalTumorSet.txt | |
| WashU-GPS-EndometriumSet.txt | |
| WashU-GPS-ColonCancerSet.txt | |
| WashU-GPS-CancerPanel.txt | |

[Delete]  [Paste Genes...]  [Import...]
[OK]  [Cancel]

| Chr | AMR_AF | ASN_AF | AFR_AF | EUR_AF |
|---|---|---|---|---|
| 1 | 0.65 | 0.87 | 0.33 | 0.7 |
| 1 | 0 | 0 | 0 | 0 |
| 1 | 0 | 0 | 0 | 0 |
| 1 | 0.92 | 0.92 | 0.9 | 0.95 |
| 1 | 0.3 | 0.21 | 0.43 | 0.4 |
| 1 | 0.99 | 0.91 | 0.99 | 0.97 |
| 1 | 0.57 | 0.19 | 0.54 | 0.71 |
| 1 | 0.62 | 0.5 | 0.47 | 0.62 |
| 1 | 0 | 0 | 0 | 0 |
| 1 | 0.51 | 0.45 | 0.07 | 0.49 |
| 1 | 0.83 | 0.86 | 0.73 | 0.82 |

*FIG. 15I*

HCC1187_T

| Variations | Chromosomes | StructVar | Maps | Genes | GO | Pathways | Report | Summary |

☐ Zygosity (○Hom ○Het) ☐ CpG Islands ☐ lncRNA ☐ dbSNP(o out o in) ☐ Allele Freq(edit) ☐ COSMIC(edit) ☐ Pathway(edit) *1509*
☐ Polyphen-2 Score(edit) ☐ Pfam(edit) ☐ OMIN(edit) ☐ Gene Ontology(edit) ☐ Gene Expr(edit) ☑ Gene List(edit) ☐ Segmental Duplication(edit)
☐ ESP6500(edit)

| | | | | | | | Chromosomes | | Location | | Variation Types |
|---|---|---|---|---|---|---|---|---|---|---|---|
| Chr | Start | End | VT | Ref | Alt | Zyg | dbSNP | AF | AMR_AF | ASN_AF | AFR_AF | EUR_AF |
| 2 | 29416572 | 29416572 | snp | T | C | 111 | rs1670283 | 0.99 | 1 | 1 | 0.97 | 1 |
| 4 | 55593464 | 55593464 | snp | A | C | 011 | rs3822214 | 0.06 | 0.06 | 0.05 | 0.06 | 0.08 |
| 7 | 55273306 | 55273306 | snp | C | T | 011 | rs35918369 | 0 | 0 | 0 | 0 | 0 |
| 7 | 116340262 | 116340262 | snp | A | G | 111 | rs33917957 | 0.02 | 0.01 | 0.05 | 0 | 0.02 |
| 10 | 43610119 | 43610119 | snp | G | A | 011 | rs1799939 | 0.15 | 0.23 | 0.1 | 0.09 | 0.2 |
| 17 | 7577091 | 7577091 | snp | G | A | 111 | rs149633775 | 0 | 0 | 0 | 0 | 0 |
| 17 | 7579472 | 7579472 | snp | G | C | 111 | rs1042522 | 0.6 | 0.72 | 0.61 | 0.33 | 0.72 |

Columns...

| EUR_AF | In Gene? | In CDS? | Sift | Polyphen-2 | PP2 Score | Pfam | TCGA | OMIM |
|---|---|---|---|---|---|---|---|---|
| 1 | ALK | I1461V | 1 | benign | 0 | | - | *105590 ANAPL INCLUDED::AL GENE INCLUDE FUSION GENE |
| 0.08 | KIT | M537L | 0.21 | benign | 0.014 | PF07714 | - | *164920 V-KIT H ONCOGENE HO FACTOR RECEP |
| 0 | EGFR | A1157V | 0 | probably damaging | 0.984 | PF07714 | - | *131550 EPIDER AVAIN ERYTHR ONCOGENE ER |
| 0.02 | MET | N375S | 0.1 | benign | 0.072 | PF07714 | - | *164860 MET PR GROWTH FACT |
| 0.2 | RET | G691S | 0.25 | benign | 0.009 | PF01403 | - | *164761 REARR ::RET PROTOO HIRSCHSPRUN |
| 0 | TP53 | R283C | 0.11 | benign | 0.065 | PF07714 | - | *191170 TUMOR PROTEIN 53; TR |
| 0.72 | TP53 | P72R | 0.18 | benign | 0.172 | PF00870 | - | *191170 TUMOR PROTEIN 53; TR |

Genome  Reference  Window  Preferences  Tools  Logout

Browse Genomes

HCC1187_T

| Variations | Chromosomes | CpG Islands | ncRNA | StructVar | Maps | Genes | GO | Pathways | Report | Summary |

| Run Rules | Run Report |

1510

| | |
|---|---|
| Gene Name | ALK |
| Genome | Tumor |
| AA Variation | I1461V |
| Prevalence | ALK NSCLC: 3-7% |
| Therapy | Crizotinib;Improved response rate and progression-free survival when treated with either pemetrexed monotherapy or combination therapy; |
| Therapy Reference | http://www.ncbi.nlm.nih.gov/pubmed/20979469;http://www.ncbi.nlm.nih.gov/pubmed/21336183; |
| Updated | 8/6/2012 |
| Gene Name | KIT |
| Genome | Tumor |
| AA Variation | M537L |
| Mutation Effect | Generally a secondary mutation in progressing or refactory GIST |
| Prevalence | KIT GIST: 1% |
| Therapy | Studies suggest sunitinib inhibits while imatinib does not in KIT double mutants with an exon 14 mutation |
| Therapy Reference | http://www.ncbi.nlm.nih.gov/pubmed/18955451 |
| Updated | 8/6/2012 |
| Gene Name | MET |
| Genome | Tumor |
| AA Variation | N375S |
| Mutation Effect | Amplification |
| Prevalence | NSCLC:2-4%;Tumors with acquired resistance to EGFR TKIs:5-20% |
| Therapy | Preclinical studies have show inhibition of MEK pathway in gastric and NSCLC models leads to cell death;crizotinib; |
| Therapy Reference | http://www.ncbi.nlm.nih.gov/pubmed/21716144;http://www.ncbi.nlm.nih.gov/pubmed/21622265; |
| Contraindication | MET amplification plays a role in acquired resistance to EGFR inhibitors of patients with EGFR-mutant tumors; |
| Contraindication Reference | http://www.ncbi.nlm.nih.gov/pubmed/21248300; |
| Updated | 8/6/2012 |
| Gene Name | RET |
| Genome | Tumor |
| AA Variation | G691S |
| Prevalence | 20-50% sporadic MTC |
| Updated | 8/9/2012 |

| Parameters for TCGA Pheno Filter | ☒ |
|---|---|
| All genomes must match:ajcc_neoplasm_disease_lymph_node_stage = N0 (i-) | *1511* |

☑ ajcc_neoplasm_disease_lymph_node_stageAny of: [N0 / N0 (i+) / N0 (i-) / N0 (mol+)] and none of: [N0 / N0 (i+) / N0 (i-) / N0 (mol+)]

☐ breast_carcinoma_progesterone_receptor_statusAny of: [Negative / Positive] and none of: [Negative / Positive]

☐ age_at_initial_pathologic_diagnosis [        ] >= value <= [        ]

☐ lab_proc_her2_neu_immunohistochemistry_receptor_statusAny of: [Equivocal / Indeterminate / Negative / Not Performed] and none of: [Equivocal / Indeterminate / Negative / Not Performed]

☐ ajcc_cancer_metastasis_stage_codeAny of: [M0 / M1 / MX] and none of: [M0 / M1 / MX]

☐ raceAny of: [AMERICAN INDIAN OR ALASKA NATIVE / ASIAN / BLACK OR AFRICAN AMERICAN / WHITE] and none of: [AMERICAN INDIAN OR ALASKA NATIVE / ASIAN / BLACK OR AFRICAN AMERICAN / WHITE]

☐ ajcc_tumor_stage_codeAny of: [T1 / T1b / T1c / T2] and none of: [T1 / T1b / T1c / T2]

☐ er_level_cell_percentage_categoryAny of: [0-10% / 10-19% / 20-29% / 40-49%] and none of: [0-10% / 10-19% / 20-29% / 40-49%]

[Check All] [Uncheck All]

[OK] [Cancel]

*FIG. 15L*

COMPUTER-BASED SYSTEMS AND METHODS FOR ANALYZING GENOMES BASED ON DISCRETE DATA STRUCTURES CORRESPONDING TO GENETIC VARIANTS THEREIN

CROSS-REFERENCE TO RELATED APPLICATIONS

This application claims the benefit of U.S. Provisional Patent Application No. 61/869,002, filed Aug. 22, 2013, which is incorporated by reference herein in its entirety.

REFERENCE TO SEQUENCE LISTING SUBMITTED ELECTRONICALLY

This application incorporates by reference a Sequence Listing with this application as an ASCII text file entitled 13247-001-999_Sub_Sequence_Listing created Sep. 3, 2019, and having a size of 2,751 bytes.

FIELD OF INVENTION

This application relates to computer-based analysis of genomes.

BACKGROUND OF INVENTION

Comparing the genomes of individuals allows for identification of signature patterns of genetic variations between those individuals. For example, knowledge of the range and types of genetic variations between individuals, or between normal and diseased tissues of a given individual, and in particular knowledge of variations that are unique to the individuals or shared between the individuals, are important in understanding disease behavior and disease progression and thus are important for planning therapeutic interventions. For example, FIG. 1A illustrates a pair of exemplary genomes 1 and 2 and a reference genome, which respectively are referred to in FIG. 1A using the shorthand "G1," "G2," and "Gref," along chromosome 1, which is referred to in FIG. 1A using the shorthand "C1." The genomes each contain a sequence of nucleic acids represented by the letters "a," "g," "c," and "t," which respectively refer to adenine, guanine, cytosine, and thymine. As can be seen in FIG. 1A, genome 1 (G1, C1) (SEQ ID NO:1) and genome 2 (G2, C1) (SEQ ID NO:2) have substantially the same sequence of nucleic acids as one another along chromosome 1, except at position 5, at which genome 1 has an "a," while genome 2 has a "c," and the reference genome has an "a." Such a variation in a single nucleic acid in genome 2, relative to the reference genome, can be referred to as a single nucleotide polymorphism, or "SNP." Additionally, in the exemplary sequences illustrated in FIG. 1A, genomes 1 and 2 both have the nucleic acid sequence "atc" at positions 20-22 on chromosome 1. Although the two genomes' sequences are the same, the reference genome (Gref, C1) (SEQ ID NO: 3) instead can have the sequence "cat" at this position. Accordingly, genomes 1 and 2 both can be considered to have a variant at positions 20-22 on chromosome 1, in which the sequence "atc" is substituted for "cat." By determining the similarities or differences in genetic variants between genomes, e.g., by determining which variants that exemplary genomes 1 and 2 illustrated in FIG. 1A are shared or are unique to the respective genome, and that are the same as or different than a reference genome, it can be possible to deduce the effect that different genetic variations can have on disease, and thus can be useful in developing a way to treat such disease.

FIG. 1B illustrates a set of basic building blocks that can be used in the logical analysis of genetic variant data using genomic set theory, and that are intended to illustrate different ways in which two genomes can be compared to one another. Specifically, FIG. 1B illustrates the "union" operation A U B, defined to mean the set of all items that exist either in A or B. FIG. 1C illustrates the "differentiate" operation A\B, defined to mean the set of all items that exist in A but not B. FIG. 1D illustrates the "intersect" operation A∩B, defined to mean the set of all items that exist in both A and B. FIG. 1E illustrates the "symmetric differentiate" operation (A\B) U (B\A), defined to mean all items that exist in A or in B, but not in both.

Operations such as illustrated in FIGS. 1B-1E can be used to perform logical analysis of sets genomic data. For example, FIG. 1F illustrates differentiation of genome 1 from genome 2, while FIG. 1G illustrates symmetric differentiation of genome 1 from genome 2. Such operations output variants that are unique either to genome 1 or to genome 2. If these genomes correspond to healthy individuals, the output variants can explain differences in normal phenotypes that lack predisposition to diseases under "ideal" conditions. Alternatively, if genome 1 corresponds to healthy tissue in a given individual and genome 2 corresponds tumor tissue from that individual, the differentiation of genome 1 from genome 2 using operations such as illustrated in FIGS. 1F and 1G can isolate tumor specific variants, which can help in identifying "driver" and "passenger" mutations in a tumor, as well as key genes involved in tumor related processes. In comparison, FIG. 1H illustrates an intersection between genome 1 and genome 2, which outputs variants that are shared between genome 1 and genome 2 and can indicate, for example, conserved areas of genomes or regions of common or shared lineage.

However, note that each individual genome to be compared includes a vast amount of data. For example, each of the 23 chromosomes of a human genome can contain about 48 million to 250 million base pairs, for a total of over 3.2 billion base pairs. Although relatively short sections of a given chromosome can be compared to one another on a manual basis, such as illustrated in FIG. 1A, computer-based approaches to genome comparison are the only practicable way of processing such high volumes of data. In such approaches, each individual's genome can be digitally represented as a series of letters representing nucleic acids such as illustrated in FIG. 1A, and two genomes can be compared to one another using computational algorithms known in the art. For example, the nucleic acid sequences in the digital representations of two genomes can be aligned relative to one another, the letters of the sequence can be compared to one another, and information about the variations in the sequence and positions thereof can be recorded in a suitable digital format, e.g., using a file format known in the art as variant call format, or VCF. A VCF file can include a list of the chromosomes, positions, reference alleles, alternate alleles, and zygosity of genetic variants in a particular genome, among other items of information. For further details on the VCF format, see Danecek et al., "The variant call format and VCFtools," Bioinformatics 27(15): 2156-2158 (Jun. 7, 2011).

However, performing operations such as illustrated in FIGS. 1B-1H based on genomic data or VCF files can be computationally intensive, and can require a relatively large amount of memory to perform on an experimentally useful time frame. For example, on Apr. 9, 2013, IBM Corporation and CLC bio issued a press release announcing that they would offer a "next generation sequencing analytics solution" that includes between 48 and 192 CPU cores and between 192 and 768 GB of memory, and software for analyzing, comparing, and visualizing high-throughput sequencing data. See press release, "IBM and CLC bio deliver combined turnkey genomics sequencing analytics solution" dated Apr. 9, 2013, issued by CLC bio and available online at www.clcbio.com/wp-content/uploads/2013/04/IBM-and-CLC-bio-deliver-combined-turnkey-genomics-sequencing-analytics-solution 1.pdf.

Methods for compressing genomic data into a computationally more manageable size also have been developed. For example, U.S. Pat. No. 7,657,383 to Allard et al. is directed to a method of representing a genome as the set of differences between a subject genome and a reference genome. Specifically, Allard discloses comparing the subject genome to the reference genome, and determining whether a difference has been found. In response to the identification of a difference, a marker is located within the reference genome, and a corresponding marker is located in the subject genome. Allard discloses that the information portions of the sequence around the genetic markers then are compared, and any offset values associated with, or assigned to, the difference. Allard discloses that a label or indicator is assigned to the difference, such as the marker number, and a text description of the difference can be assigned, such as the type of difference, such as an addition, deletion, translocation, SNP, or repetitive microsatellite. Allard discloses that the accumulated data, such as indicators or marker numbers, starting and/or ending offsets, translocation information, and/or other information can be stored. Allard discloses that the entire set of descriptive data can specify the subject genome.

However, comparing two genomes along their entire lengths, as disclosed by Allard to generate a set of data specifying a subject genome, is computationally intensive. Moreover, the number of data sets thus generated scales linearly with the number of subject genomes analyzed, thus requiring at least a linear increase in the computational effort to perform such analysis and in the amount of storage space required to store the data sets.

Thus, what is needed is a computationally efficient method of storing and analyzing genomic data.

SUMMARY OF INVENTION

Embodiments of the present invention provide computer-based systems, methods, and data structures for use in analyzing genomic data based on discrete data structures corresponding to genetic variants therein.

Under one aspect of the present invention, a computer-based method for analyzing genetic variants within a plurality of genomes is provided. The method includes submitting a query term to a database storing a plurality of discrete data structures within a memory. Each data structure can uniquely correspond to only one of the genetic variants present within the plurality of genomes, and can include a first data field comprising a unique alphanumeric identifier for the corresponding genetic variant and a second data field comprising a unique alphanumeric identifier for a genome in which the corresponding genetic variant is present. The query term can include a unique alphanumeric identifier for at least one genome of the plurality of genomes and an operation to be performed on that genome. The method further can include searching the second data fields of the plurality of data structures stored in the database for unique alphanumeric identifiers that match the query term and satisfy the operation; and generating an output representing the result of performing the search.

In some embodiments, at least one of the discrete data structures comprises a third data field comprising a unique alphanumeric identifier for an additional genome in which the corresponding genetic variant is present. The query term can include unique alphanumeric identifiers for two or more genomes of the plurality of genomes. The operation can be selected from the group consisting of union, differentiate, intersect, and symmetric differentiate. The output can include a list or graphical representation of genetic variants that are shared between the two or more genomes or that are unique to only one of the two or more genomes. Preferably, the method is performed using a personal computer.

In some embodiments, the unique alphanumeric identifier for the corresponding genetic variant comprises a hash or concatenation of alphanumeric identifiers for a chromosome, position, reference allele, and variant allele for that genetic variant.

Each data structure further can include a plurality of additional data fields respectively storing alphanumeric identifiers for a chromosome, position, reference allele, and variant allele for the corresponding genetic variant.

In some embodiments, at least one of the discrete data structures further can include a third data field storing an alphanumeric representation of a nucleic acid characteristic. The query term can include an identification of the nucleic acid characteristic, and said searching further can include, in the data structures having second data fields comprising unique alphanumeric identifiers that match the query term and satisfy the operation, searching the third data fields for the identified nucleic acid characteristic.

The nucleic acid characteristic can be selected from the group consisting of: a gene based characteristic, a nucleotide-based characteristic, a score-based characteristic, a genome-based characteristic, and a sample-specific characteristic.

In some embodiments, the gene-based characteristic is selected from the group consisting of: a name or identifier of a gene in which the corresponding genetic variant is present, a biochemical pathway in which the genetic variant or a gene in which it is present is known to participate, an indication of whether the corresponding genetic variant is listed in a particular curated data source, a cancer type in which the corresponding genetic variant or a gene in which it is present is involved, a disease phenotype in which the corresponding genetic variant or a gene in which it is present is involved, a gene that is known to be expressed that contains the genetic variant, a dbSNP associated with the corresponding genetic variant, and a transcription factor that is at least partially encoded by the genetic variant.

In some embodiments, the nucleotide-based characteristic is an indication of methylation, is an alphanumeric description of a genomic location in which the corresponding genetic variant is present, the genomic location selected from the group consisting of: an exon, an intron, a regulatory region, a splice site, a flanking region, a promoter region, and a region that codes for non-coding RNA, or is an alphanumeric description of a type of the corresponding genetic variant selected from the group consisting of: missense, nonsense, synonymous, insertion, deletion, and structural variation.

In some embodiments, the score-based characteristic is selected from the group consisting of: an allele frequency associated with the corresponding genetic variant, a SIFT score associated with the corresponding genetic variant, a PolyPhen-2 score associated with the corresponding genetic variant, a PolyPhen score associated with the corresponding genetic variant, and a PFAM associated with the corresponding genetic variant.

In some embodiments, the genome-based characteristic is selected from the group consisting of: a zygosity of the genome in which the corresponding genetic variant is present, a fractional allele frequency for the corresponding genetic variant in the genome in which the corresponding genetic variant is present, a phenotype of the genome in which the corresponding genetic variant is present, a demographic of the genome in which the corresponding genetic variant is present, and a clinical indication of the genome in which the corresponding genetic variant is present.

In some embodiments, the sample-specific characteristic is selected from the group consisting of: a read quality of the genome in which the corresponding genetic variant is present, and a read depth of the genome in which the corresponding genetic variant is present.

In some embodiments, the plurality of discrete data structures includes at least 10 million discrete data structures. The method can be performed using a personal computer.

Under another aspect of the present invention, a computer-based system for analyzing genetic variants within a plurality of genomes is provided. The system can include a processor; and a memory in operable communication with the processor. The memory can store a query module configured to cause the processor to submit a query term to a database storing a plurality of data structures. Each data structure can uniquely correspond to only one of the genetic variants present within the plurality of genomes, and can include a first data field comprising a unique alphanumeric identifier for the corresponding genetic variant and a second data field comprising a unique alphanumeric identifier for a genome in which the corresponding genetic variant is present. The query term can include a unique alphanumeric identifier for at least one genome of the plurality of genomes and an operation to be performed on that genome. The query module further can be configured to cause the processor to search the data fields of the plurality of data structures stored in the database for unique alphanumeric identifiers that match the query term and satisfy the operation. The query module further can be configured to cause the processor to generate an output representing the result of performing the search.

In some embodiments, at least one of the discrete data structures comprises a third data field comprising a unique alphanumeric identifier for an additional genome in which the corresponding genetic variant is present. The query term can include unique alphanumeric identifiers for two or more genomes of the plurality of genomes. The operation can be selected from the group consisting of union, differentiate, intersect, and symmetric differentiate. The output can include a list or graphical representation of genetic variants that are shared between the two or more genomes or that are unique to only one of the two or more genomes. The computer-based system can be a personal computer.

In some embodiments, the unique alphanumeric identifier for the corresponding genetic variant comprises a hash or concatenation of alphanumeric identifiers for a chromosome, position, reference allele, and variant allele for that genetic variant. Each data structure further can include a plurality of additional data fields respectively storing alphanumeric identifiers for a chromosome, position, reference allele, and variant allele for the corresponding genetic variant.

In some embodiments, at least one of the discrete data structures further comprises a third data field storing an alphanumeric representation of a nucleic acid characteristic. The query term can include an identification of the nucleic acid characteristic, and said searching further can include, in the data structures having second data fields comprising unique alphanumeric identifiers that match the query term and satisfy the operation, searching the third data fields for the identified nucleic acid characteristic.

The nucleic acid characteristic can be selected from the group consisting of: a gene-based characteristic, a nucleotide-based characteristic, a genome-based characteristic, and a sample-specific characteristic.

In some embodiments, the gene-based characteristic is selected from the group consisting of: a name or identifier of a gene in which the corresponding genetic variant is present, a biochemical pathway in which the genetic variant or a gene in which it is present is known to participate, an indication of whether the corresponding genetic variant is listed in a particular curated data source, a cancer type in which the corresponding genetic variant or a gene in which it is present is involved, a disease phenotype in which the corresponding genetic variant or a gene in which it is present is involved, a gene that is known to be expressed that contains the genetic variant, a dbSNP associated with the corresponding genetic variant, and a transcription factor that is at least partially encoded by the genetic variant.

In some embodiments, the nucleotide-based characteristic is an indication of methylation, is an alphanumeric description of a genomic location in which the corresponding genetic variant is present, the genomic location selected from the group consisting of: an exon, an intron, a regulatory region, a splice site, a flanking region, a promoter region, and a region that codes for non-coding RNA, or is an alphanumeric description of a type of the corresponding genetic variant selected from the group consisting of: missense, nonsense, synonymous, insertion, deletion, and structural variation.

In some embodiments, the score-based characteristic is selected from the group consisting of: an allele frequency associated with the corresponding genetic variant, a SIFT score associated with the corresponding genetic variant, a PolyPhen-2 score associated with the corresponding genetic variant, a PolyPhen score associated with the corresponding genetic variant, and a PFAM associated with the corresponding genetic variant.

In some embodiments, the genome-based characteristic is selected from the group consisting of: a zygosity of the genome in which the corresponding genetic variant is present, a fractional allele frequency for the corresponding genetic variant in the genome in which the corresponding genetic variant is present, a phenotype of the genome in which the corresponding genetic variant is present, a demographic of the genome in which the corresponding genetic variant is present, and a clinical indication of the genome in which the corresponding genetic variant is present.

In some embodiments, the sample-specific characteristic is selected from the group consisting of: a read quality of the genome in which the corresponding genetic variant is present, and a read depth of the genome in which the corresponding genetic variant is present.

In some embodiments, the plurality of discrete data structures includes at least 10 million discrete data structures. The system can be a personal computer.

Under another aspect, a computer-based system for analyzing genetic variants within a plurality of genomes is provided. The system can include processing means; and storage means in operable communication with the processing means. The storage means can store query means for causing the processing means to submit a query term to database means storing a plurality of data structures. Each data structure can uniquely correspond to only one of the genetic variants present within the plurality of genomes, and can include a first data field comprising a unique alphanumeric identifier for the corresponding genetic variant and a second data field comprising a unique alphanumeric identifier for a genome in which the corresponding genetic variant is present. The query term can include a unique alphanumeric identifier for at least one genome of the plurality of genomes and an operation to be performed on that genome. The system further can include search means for causing the processing means to search the data fields of the plurality of data structures stored in the database means for unique alphanumeric identifiers that match the query term and satisfy the operation. The system further can include output means for causing the processing means to generate an output representing the result of performing the search.

Under another aspect, a memory for storing data for access by an application program being executed on a data processing system is provided. The memory can include a plurality of discrete data structures stored in said memory and including information resident in a database used by said application program. Each data structure can uniquely correspond to only one genetic variant present in a plurality of genomes, and can include a first data field uniquely comprising a unique alphanumeric identifier for the corresponding genetic variant and a second data field comprising a unique alphanumeric identifier for a genome in which that genetic variant is present.

In some embodiments, at least one of the discrete data structures comprises a third data field comprising a unique alphanumeric identifier for an additional genome in which the corresponding genetic variant is present.

In some embodiments, the data processing system is a personal computer.

In some embodiments, the unique alphanumeric identifier for the corresponding genetic variant comprises a hash or concatenation of alphanumeric identifiers for a chromosome, position, reference allele, and variant allele for that genetic variant.

In some embodiments, each data structure further comprises a plurality of additional data fields respectively storing alphanumeric identifiers for a chromosome, position, reference allele, and variant allele for the corresponding genetic variant.

In some embodiments, at least one of the discrete data structures further comprises a third data field storing an alphanumeric representation of a nucleic acid characteristic.

The nucleic acid characteristic can be selected from the group consisting of: a gene-based characteristic, a nucleotide-based characteristic, a score-based characteristic, a genome-based characteristic, and a sample-based characteristic.

In some embodiments, the gene-based characteristic is selected from the group consisting of: a name or identifier of a gene in which the corresponding genetic variant is present, a biochemical pathway in which the genetic variant or a gene in which it is present is known to participate, an indication of whether the corresponding genetic variant is listed in a particular curated data source, a cancer type in which the corresponding genetic variant or a gene in which it is present is involved, a disease phenotype in which the corresponding genetic variant or a gene in which it is present is involved, a gene that is known to be expressed that contains the genetic variant, a dbSNP associated with the corresponding genetic variant, and a transcription factor that is at least partially encoded by the genetic variant.

In some embodiments, the nucleotide-based characteristic is an indication of methylation, is an alphanumeric description of a genomic location in which the corresponding genetic variant is present, the genomic location selected from the group consisting of: an exon, an intron, a regulatory region, a splice site, a flanking region, a promoter region, and a region that codes for non-coding RNA, or is an alphanumeric description of a type of the corresponding genetic variant selected from the group consisting of: missense, nonsense, synonymous, insertion, deletion, and structural variation.

In some embodiments, the score-based characteristic is selected from the group consisting of: an allele frequency associated with the corresponding genetic variant, a SIFT score associated with the corresponding genetic variant, a PolyPhen-2 score associated with the corresponding genetic variant, a PolyPhen score associated with the corresponding genetic variant, and a PFAM associated with the corresponding genetic variant.

In some embodiments, the genome-based characteristic is selected from the group consisting of: a zygosity of the genome in which the corresponding genetic variant is present, a fractional allele frequency for the corresponding genetic variant in the genome in which the corresponding genetic variant is present, a phenotype of the genome in which the corresponding genetic variant is present, a demographic of the genome in which the corresponding genetic variant is present, and a clinical indication of the genome in which the corresponding genetic variant is present.

In some embodiments, the sample-specific characteristic is selected from the group consisting of: a read quality of the genome in which the corresponding genetic variant is present, and a read depth of the genome in which the corresponding genetic variant is present.

In some embodiments, the plurality of discrete data structures includes at least 10 million discrete data structures. The data processing system may be a personal computer.

Under another aspect of the present invention, a computer-based method for generating a database for use in analyzing genetic variants is provided. The method can include receiving a digital representation of genetic variants within a first genome, and for each genetic variant within the digital representation, determining whether that genetic variant corresponds to an existing discrete data structure within a plurality of existing discrete data structures stored within a database. Each existing discrete data structure can uniquely correspond to only one genetic variant present within at least one other genome, and can include a first data field comprising a unique alphanumeric identifier for the corresponding genetic variant and a second data field comprising a unique alphanumeric identifier for the at least one other genome. If that genetic variant is determined to correspond to an existing data structure, then the corresponding existing discrete data structure can be modified to include a third data field comprising a unique alphanumeric identifier for the first genome, the modified existing discrete data structure stored within the database. If that genetic variant instead is determined not to correspond to an existing discrete data structure, then the digital representation of that genetic variant can be converted into an additional discrete data structure uniquely corresponding to only that genetic variant, and including a first data field comprising a unique alphanumeric identifier for the corresponding genetic variant and a second data field comprising a unique alphanumeric identifier for the first genome, and stored the additional discrete data structure within the database.

In some embodiments, determining whether that genetic variant corresponds to an existing discrete data structure can include generating a unique alphanumeric identifier for that genetic variant; and searching the first data fields of the existing discrete data structures stored within the database for a unique alphanumeric identifier that matches the unique alphanumeric identifier for that genetic variant.

In some embodiments, at least one of the existing discrete data structures comprises one or more additional data fields comprising one or more unique alphanumeric identifiers for additional genomes in which the corresponding genetic variant is present.

In some embodiments, said digital representation of the genetic variants within the first genome comprises alphanumeric fields respectively describing a chromosome, a position along that chromosome, a reference allele, and a variant allele corresponding to each genetic variant, and said converting comprises generating the unique alphanumeric identifier for that genetic variant based on the alphanumeric fields respectively describing the position, chromosome, reference allele, and variant allele for that genetic variant.

In some embodiments, the unique alphanumeric identifier is generated by hashing or concatenating the alphanumeric identifiers for the chromosome, position, reference allele, and variant allele for that genetic variant.

Some embodiments further can include generating within the additional discrete data structure a plurality of additional data fields respectively storing the alphanumeric identifiers for the chromosome, position, reference allele, and variant allele of that genetic variant.

In some embodiments, the digital representation of the first genome is a variant call format (VCF) file, a genome variation format (GVF) file, a general feature format (GFF) file, a general transfer format (GTF) file, a sequence alignment data (SAM) file, a binary sequence alignment data (BAM) file, a BED file, a FASTA file, or a FASTQ file.

Some embodiments further can include generating within the additional discrete data structure a third data field storing an alphanumeric representation of a nucleic acid characteristic.

In some embodiments, the third data field can be generated by performing steps that include obtaining a genome mask comprising a plurality of chromosome masks. Each chromosome mask can correspond to a chromosome and include an array of bits, each bit corresponding to a base pair position in the corresponding chromosome, wherein only bits corresponding to a position of the nucleic acid characteristic include a flag. The steps further can include determining whether a bit within the genome mask that corresponds to the chromosome and position of the corresponding genetic variant includes a flag. If the bit is determined to include a flag, a query can be submitted to the curated data source requesting information about the nucleic acid characteristic at the chromosome and position corresponding to that bit, and the query result stored in the third data field.

Some embodiments further can include obtaining each chromosome mask comprises generating an array of bits, each bit corresponding to a base pair position in the corresponding chromosome. Then, for each bit, a query can be submitted to the curated data source requesting a response of whether the corresponding chromosome includes the nucleic acid characteristic at the position corresponding to that bit. The bit can be flagged if the curated data source responds that the corresponding chromosome does include the nucleic acid characteristic at the position corresponding to that bit; and the bit can not be flagged if the curated data source responds that the corresponding chromosome does not include the nucleic acid characteristic at the position corresponding to that bit. In some embodiments, flagging the bit comprises setting the bit to "1," and not flagging the bit comprises setting the bit to "0." In some embodiments, generating the array of bits comprises generating an array of M integers each having length N, wherein M×N≥L, where L is a number of base pairs in the corresponding chromosome.

The nucleic acid characteristic can be selected from the group consisting of: a gene-based characteristic, a nucleotide-based characteristic, a score-based characteristic, a genome-based characteristic, and a sample-specific characteristic.

In some embodiments, the gene-based characteristic is selected from the group consisting of: a name or identifier of a gene in which the corresponding genetic variant is present, a biochemical pathway in which the genetic variant or a gene in which it is present is known to participate, an indication of whether the corresponding genetic variant is listed in a particular curated data source, a cancer type in which the corresponding genetic variant or a gene in which it is present is involved, a disease phenotype in which the corresponding genetic variant or a gene in which it is present is involved, a gene that is known to be expressed that contains the genetic variant, and a transcription factor that is at least partially encoded by the genetic variant.

In some embodiments, the nucleotide-based characteristic is an indication of methylation, an alphanumeric description of a genomic location in which the corresponding genetic variant is present, the genomic location selected from the group consisting of: an exon, an intron, a regulatory region, a splice site, a flanking region, a promoter region, and a region that codes for non-coding RNA, or is an alphanumeric description of a type of the corresponding genetic variant selected from the group consisting of: missense, nonsense, synonymous, insertion, deletion, and structural variation.

In some embodiments, the score-based characteristic is selected from the group consisting of: an allele frequency associated with the corresponding genetic variant, a SIFT score associated with the corresponding genetic variant, a PolyPhen-2 score associated with the corresponding genetic variant, a PolyPhen score associated with the corresponding genetic variant, and a PFAM associated with the corresponding genetic variant.

In some embodiments, the genome-based characteristic is selected from the group consisting of: a zygosity of the genome in which the corresponding genetic variant is present, a fractional allele frequency for the corresponding genetic variant in the genome in which the corresponding genetic variant is present, a phenotype of the genome in which the corresponding genetic variant is present, a demographic of the genome in which the corresponding genetic variant is present, and a clinical indication of the genome in which the corresponding genetic variant is present.

In some embodiments, the sample-specific characteristic is selected form the group consisting of: a read quality of the genome in which the corresponding genetic variant is present, and a read depth of the genome in which the corresponding genetic variant is present.

In some embodiments, the resulting plurality of discrete data structures include at least 10 million discrete data structures. The method can be performed using a personal computer. In some embodiments, the method is performed in random access memory (RAM) of the personal computer.

Under another aspect of the present invention, a computer-based system for generating a database for use in analyzing genetic variants is provided. The system can include a processor; and a memory in operable communication with the processor, the memory storing a data structure module configured to cause the processor to receive a digital representation of genetic variants within a first genome. For each genetic variant within the first genome, the data structure module can cause the processor to determine whether that genetic variant corresponds to an existing discrete data structure within a plurality of existing discrete data structures stored within a database. Each existing discrete data structure can uniquely correspond to only one genetic variant present within at least one other genome, and can include a first data field comprising a unique alphanumeric identifier for the corresponding genetic variant and a second data field comprising a unique alphanumeric identifier for the at least one other genome. If that genetic variant is determined to correspond to an existing data structure, the data structure module can cause the processor to modify the corresponding existing discrete data structure to include a third data field comprising a unique alphanumeric identifier for the first genome, and to store the modified existing discrete data structure within the database. If instead that genetic variant is determined not to correspond to an existing discrete data structure, the data structure module can cause the processor to convert the digital representation of that genetic variant into an additional discrete data structure uniquely corresponding to only that genetic variant and to store the additional discrete data structure within the database. The additional discrete data structure can include a unique alphanumeric identifier for the corresponding genetic variant and a second data field comprising a unique alphanumeric identifier for the first genome.

In some embodiments, determining whether that genetic variant corresponds to an existing discrete data structure can include generating a unique alphanumeric identifier for that genetic variant; and searching the first data fields of the existing discrete data structures stored within the database for a unique alphanumeric identifier that matches the unique alphanumeric identifier for that genetic variant.

In some embodiments, at least one of the existing discrete data structures comprises one or more additional data fields comprising one or more unique alphanumeric identifiers for additional genomes in which the corresponding genetic variant is present.

In some embodiments, said digital representation of the genetic variants within the first genome comprises alphanumeric fields respectively describing a chromosome, a position along that chromosome, a reference allele, and a variant allele corresponding to each genetic variant. The data structure module can be configured to cause the processor to perform said converting by generating the unique alphanumeric identifier for that genetic variant based on the alphanumeric fields respectively describing the position, chromosome, reference allele, and variant allele for that genetic variant. In some embodiments, the data structure module is configured to cause the processor to generate the unique alphanumeric identifier by hashing or concatenating the alphanumeric identifiers for the chromosome, position, reference allele, and variant allele for that genetic variant. In some embodiments, the data structure module is further configured to cause the processor to generate within the additional discrete data structure a plurality of additional data fields respectively storing the alphanumeric identifiers for the chromosome, position, reference allele, and variant allele of that genetic variant.

In some embodiments, the digital representation of the first genome is a variant call format (VCF) file, a genome variation format (GVF) file, a general feature format (GFF) file, a general transfer format (GTF) file, a sequence alignment data (SAM) file, a binary sequence alignment data (BAM) file, a BED file, a FASTA file, or a FASTQ file.

In some embodiments, the memory further stores a decorator module configured to cause the processor to generate within the additional discrete data structure a third data field storing an alphanumeric representation of a nucleic acid characteristic.

In some embodiments, the memory further stores a decorator module configured to cause the processor to generate the third data field storing the alphanumeric representation of the nucleic acid characteristic by performing steps comprising: obtaining a genome mask comprising a plurality of chromosome masks, each chromosome mask corresponding to a chromosome and comprising an array of bits, each bit corresponding to a base pair position in the corresponding chromosome, wherein only bits corresponding to a position of the nucleic acid characteristic include a flag; and determining whether a bit within the genome mask that corresponds to the chromosome and position of the corresponding genetic variant includes a flag. If the bit is determined to include a flag, the processor can submit a query to the curated data source requesting information about the nucleic acid characteristic at the chromosome and position corresponding to that bit, and can store the query result in the third data field.

In some embodiments, the decorator module is configured to cause the processor to obtain each chromosome mask by performing steps comprising: generating an array of bits, each bit corresponding to a base pair position in the corresponding chromosome; and for each bit: submitting a query to the curated data source requesting a response of whether the corresponding chromosome includes the nucleic acid characteristic at the position corresponding to that bit; flagging the bit if the curated data source responds that the corresponding chromosome does include the nucleic acid characteristic at the position corresponding to that bit; and not flagging the bit if the curated data source responds that the corresponding chromosome does not include the nucleic acid characteristic at the position corresponding to that bit. In some embodiments, flagging the bit comprises setting the bit to "1," and not flagging the bit comprises setting the bit to "0." In some embodiments, generating the array of bits comprises generating an array of M integers each having length N, wherein $M \times N \geq L$, where L is a number of base pairs in the corresponding chromosome.

The nucleic acid characteristic can be selected from the group consisting of: a gene-based characteristic, a nucleotide-based characteristic, a score-based characteristic, a genome-based characteristic, and a sample-specific characteristic.

In some embodiments, the gene-based characteristic is selected from the group consisting of: a name or identifier of a gene in which the corresponding genetic variant is present, a biochemical pathway in which the genetic variant or a gene in which it is present is known to participate, an indication of whether the corresponding genetic variant is listed in a particular curated data source, a cancer type in which the corresponding genetic variant or a gene in which it is present is involved, a disease phenotype in which the corresponding genetic variant or a gene in which it is present is involved, a gene that is known to be expressed that contains the genetic variant, and a transcription factor that is at least partially encoded by the genetic variant.

In some embodiments, the nucleotide-based characteristic is an indication of methylation, is an alphanumeric description of a genomic location in which the corresponding genetic variant is present, the genomic location selected from the group consisting of: an exon, an intron, a regulatory region, a splice site, a flanking region, a promoter region, and a region that codes for non-coding RNA, or is an alphanumeric description of a type of the corresponding genetic variant selected from the group consisting of: missense, nonsense, synonymous, insertion, deletion, and structural variation.

In some embodiments, the score-based characteristic is selected from the group consisting of: an allele frequency associated with the corresponding genetic variant, a SIFT score associated with the corresponding genetic variant, a PolyPhen-2 score associated with the corresponding genetic variant, a PolyPhen score associated with the corresponding genetic variant, and a PFAM associated with the corresponding genetic variant.

In some embodiments, the genome-based characteristic is selected from the group consisting of: a zygosity of the genome in which the corresponding genetic variant is present, a fractional allele frequency for the corresponding genetic variant in the genome in which the corresponding genetic variant is present, a phenotype of the genome in which the corresponding genetic variant is present, a demographic of the genome in which the corresponding genetic variant is present, and a clinical indication of the genome in which the corresponding genetic variant is present.

In some embodiments, the sample-specific characteristic is selected from the group consisting of: a read quality of the genome in which the corresponding genetic variant is present, and a read depth of the genome in which the corresponding genetic variant is present.

In some embodiments, the resulting plurality of discrete data structures includes at least 10 million discrete data structures. The system may be a personal computer.

Under another aspect of the present invention, a computer-based system for generating database means for use in analyzing genetic variants is provided. The system can include processing means; and memory means in operable communication with the processor, the memory means storing data structure means for causing the processor to receive a digital representation of genetic variants within a first genome, and for each genetic variant within the digital representation: to determine whether that genetic variant corresponds to an existing discrete data structure within a plurality of existing discrete data structures stored within the database means, each existing discrete data structure uniquely corresponding to only one genetic variant present within at least one other genome, each existing discrete data structure comprising a first data field comprising a unique alphanumeric identifier for the corresponding genetic variant and a second data field comprising a unique alphanumeric identifier for the at least one other genome; if that genetic variant is determined to correspond to an existing data structure, to modify the corresponding existing discrete data structure to include a third data field comprising a unique alphanumeric identifier for the first genome, and to store the modified existing discrete data structure within the database means; and if that genetic variant is determined not to correspond to an existing discrete data structure, to convert the digital representation of that genetic variant into an additional discrete data structure uniquely corresponding to only that genetic variant, the additional discrete data structure comprising a first data field comprising a unique alphanumeric identifier for the corresponding genetic variant and a second data field comprising a unique alphanumeric identifier for the first genome, and to store the additional discrete data structure within the database means.

Under another aspect of the present invention, a computer-based method for generating a database for use in analyzing genetic variants is provided. The method can include converting a digital representation of genetic variants within a first genome into a plurality of discrete data structures. Each data structure can uniquely correspond to only one of the genetic variants present in the first genome and can include a first data field comprising a unique alphanumeric identifier for the corresponding variant and a second data field comprising a unique alphanumeric identifier for the first genome. The method also can include storing the plurality of discrete data structures in a database in a memory.

In some embodiments, said digital representation of the genetic variants within the first genome comprises alphanumeric fields respectively describing a chromosome, a position along that chromosome, a reference allele, and a variant allele corresponding to each genetic variant, and said converting can include generating the unique alphanumeric identifier for that genetic variant based on the alphanumeric fields respectively describing the position, chromosome, reference allele, and variant allele for that genetic variant.

In some embodiments, the unique alphanumeric identifier is generated by hashing or concatenating the alphanumeric identifiers for the chromosome, position, reference allele, and variant allele for that genetic variant.

Some embodiments further include generating within each discrete data structure a plurality of additional data fields respectively storing the alphanumeric identifiers for the chromosome, position, reference allele, and variant allele of that genetic variant.

In some embodiments, the digital representation of the first genome is a variant call format (VCF) file, a genome variation format (GVF) file, a general feature format (GFF) file, a general transfer format (GTF) file, a sequence alignment data (SAM) file, a binary sequence alignment data (BAM) file, a BED file, a FASTA file, or a FASTQ file.

Some embodiments further include generating within at least one of the discrete data structures a third data field storing an alphanumeric representation of a nucleic acid characteristic.

In some embodiments, the third data field can be generated by performing steps comprising: obtaining a genome mask comprising a plurality of chromosome masks, each chromosome mask corresponding to a chromosome and comprising an array of bits, each bit corresponding to a base pair position in the corresponding chromosome, wherein only bits corresponding to a position of the nucleic acid characteristic include a flag; and determining whether a bit within the genome mask that corresponds to the chromosome and position of the corresponding genetic variant includes a flag. If the bit is determined to include a flag, a query can be submitted to the curated data source requesting information about the nucleic acid characteristic at the chromosome and position corresponding to that bit, and the query result stored in the third data field.

In some embodiments, obtaining each chromosome mask comprises generating an array of bits, each bit corresponding to a base pair position in the corresponding chromosome; and for each bit: submitting a query to the curated data source requesting a response of whether the corresponding chromosome includes the nucleic acid characteristic at the position corresponding to that bit; flagging the bit if the curated data source responds that the corresponding chromosome does include the nucleic acid characteristic at the position corresponding to that bit; and not flagging the bit if the curated data source responds that the corresponding chromosome does not include the nucleic acid characteristic at the position corresponding to that bit. In some embodiments, flagging the bit comprises setting the bit to "1," and not flagging the bit comprises setting the bit to "0." In some embodiments, generating the array of bits comprises generating an array of M integers each having length N, wherein $M \times N \geq L$, where L is a number of base pairs in the corresponding chromosome.

The nucleic acid characteristic can be selected from the group consisting of: a gene-based characteristic, a nucleotide-based characteristic, a score-based characteristic, a genome-based characteristic, and a sample-specific characteristic.

In some embodiments, the gene-based characteristic is selected from the group consisting of: a name or identifier of a gene in which the corresponding genetic variant is present, a biochemical pathway in which the genetic variant or a gene in which it is present is known to participate, an indication of whether the corresponding genetic variant is listed in a particular curated data source, a cancer type in which the corresponding genetic variant or a gene in which it is present is involved, a disease phenotype in which the corresponding genetic variant or a gene in which it is present is involved, a gene that is known to be expressed that contains the genetic variant, a dbSNP associated with the corresponding genetic variant, and a transcription factor that is at least partially encoded by the genetic variant.

In some embodiments, the nucleotide-based characteristic is an indication of methylation, is an alphanumeric description of a genomic location in which the corresponding genetic variant is present, the genomic location selected from the group consisting of: an exon, an intron, a regulatory region, a splice site, a flanking region, a promoter region, and a region that codes for non-coding RNA, or is an alphanumeric description of a type of the corresponding genetic variant selected from the group consisting of: missense, nonsense, synonymous, insertion, deletion, and structural variation.

In some embodiments, the score-based characteristic is selected from the group consisting of: an allele frequency associated with the corresponding genetic variant, a SIFT score associated with the corresponding genetic variant, a PolyPhen-2 score associated with the corresponding genetic variant, a PolyPhen score associated with the corresponding genetic variant, and a PFAM associated with the corresponding genetic variant.

In some embodiments, the genome-based characteristic is selected from the group consisting of: a zygosity of the genome in which the corresponding genetic variant is present, a fractional allele frequency for the corresponding genetic variant in the genome in which the corresponding genetic variant is present, a phenotype of the genome in which the corresponding genetic variant is present, a demographic of the genome in which the corresponding genetic variant is present, and a clinical indication of the genome in which the corresponding genetic variant is present.

In some embodiments, the sample-specific characteristic is selected from the group consisting of: a read quality of the genome in which the corresponding genetic variant is present, and a read depth of the genome in which the corresponding genetic variant is present.

Some embodiments further include obtaining digital representations of genetic variants within additional genomes, and for each genetic variant within each digital representation: determining whether that genetic variant corresponds to a discrete data structure stored within the database. If that genetic variant is determined to correspond to a stored discrete data structure, the corresponding stored discrete data structure can be modified to include a third data field comprising a unique alphanumeric identifier for the additional genome, and storing the modified discrete data structure within the database. If instead that genetic variant is determined not to correspond to a stored discrete data structure, the digital representation of that genetic variant can be converted into an additional discrete data structure uniquely corresponding to only that genetic variant and including a first data field comprising a unique alphanumeric identifier for the corresponding genetic variant and a second data field comprising a unique alphanumeric identifier for the additional genome. The additional discrete data structure can be stored within the database.

In some embodiments, determining whether that genetic variant corresponds to a stored discrete data structure can include generating a unique alphanumeric identifier for that genetic variant; and searching the first data fields of the existing discrete data structures stored within the database for a unique alphanumeric identifier that matches the unique alphanumeric identifier for that genetic variant.

The resulting plurality of discrete data structures can include at least 10 million discrete data structures. The method can be performed using a personal computer. In particular, the method can be performed in random access memory (RAM) of the personal computer.

In some embodiments, a computer-based system for generating a database for use in analyzing genetic variants is provided. The system can include a processor; and a memory in operable communication with the processor. The memory can store a data structure module configured to cause the processor to receive a digital representation of genetic variants within a first genome, and for each genetic variant within the digital representation, to convert the digital representation of that genetic variant within the a discrete data structure uniquely corresponding to only that genetic variant, the data structure comprising a first data field comprising a unique alphanumeric identifier for the corresponding variant and a second data field comprising a unique alphanumeric identifier for the first genome; and to store the discrete data structure in a database in a memory.

In some embodiments, the digital representation of the genetic variants within the first genome comprises alphanumeric fields respectively describing a chromosome, a position along that chromosome, a reference allele, and a variant allele corresponding to each genetic variant, and said converting comprises generating the unique alphanumeric identifier for that genetic variant based on the alphanumeric fields respectively describing the position, chromosome, reference allele, and variant allele for that genetic variant.

In some embodiments, the data structure module is configured to cause the processor to generate the unique alphanumeric identifier by hashing or concatenating the alphanumeric identifiers for the chromosome, position, reference allele, and variant allele for that genetic variant.

In some embodiments, the data structure module further is configured to cause the processor to generate within each discrete data structure a plurality of additional data fields respectively storing the alphanumeric identifiers for the chromosome, position, reference allele, and variant allele of that genetic variant.

In some embodiments, the digital representation of the first genome is a variant call format (VCF) file, a genome variation format (GVF) file, a general feature format (GFF)

file, a general transfer format (GTF) file, a sequence alignment data (SAM) file, a binary sequence alignment data (BAM) file, a BED file, a FASTA file, or a FASTQ file.

In some embodiments, the memory further stores a decorator module configured to cause the processor to generate within the additional discrete data structure a third data field storing an alphanumeric representation of a nucleic acid characteristic.

In some embodiments, the memory further stores a decorator module configured to cause the processor to generate the third data field by performing steps comprising: obtaining a genome mask comprising a plurality of chromosome masks, each chromosome mask corresponding to a chromosome and comprising an array of bits, each bit corresponding to a base pair position in the corresponding chromosome, wherein only bits corresponding to a position of the nucleic acid characteristic include a flag; and determining whether a bit within the genome mask that corresponds to the chromosome and position of the corresponding genetic variant includes a flag. If the bit is determined to include a flag, the processor can submit a query to the curated data source requesting information about the nucleic acid characteristic at the chromosome and position corresponding to that bit, and storing the query result in the third data field.

In some embodiments, the decorator module is configured to cause the processor to obtain each chromosome mask by performing steps comprising: generating an array of bits, each bit corresponding to a base pair position in the corresponding chromosome; and for each bit: submitting a query to the curated data source requesting a response of whether the corresponding chromosome includes the nucleic acid characteristic at the position corresponding to that bit; flagging the bit if the curated data source responds that the corresponding chromosome does include the nucleic acid characteristic at the position corresponding to that bit; and not flagging the bit if the curated data source responds that the corresponding chromosome does not include the nucleic acid characteristic at the position corresponding to that bit.

In some embodiments, flagging the bit comprises setting the bit to "1," and wherein not flagging the bit comprises setting the bit to "0." In some embodiments, generating the array of bits comprises generating an array of M integers each having length N, wherein $M \times N \geq L$, where L is a number of base pairs in the corresponding chromosome.

The nucleic acid characteristic can be selected from the group consisting of: a gene-based characteristic, a nucleotide-based characteristic, a score-based characteristic, a genome-based characteristic, and a sample-specific characteristic.

In some embodiments, the gene-based characteristic is selected from the group consisting of: a name or identifier of a gene in which the corresponding genetic variant is present, a biochemical pathway in which the genetic variant or a gene in which it is present is known to participate, an indication of whether the corresponding genetic variant is listed in a particular curated data source, a cancer type in which the corresponding genetic variant or a gene in which it is present is involved, a disease phenotype in which the corresponding genetic variant or a gene in which it is present is involved, a gene that is known to be expressed that contains the genetic variant, a dbSNP associated with the corresponding genetic variant, and a transcription factor that is at least partially encoded by the genetic variant.

In some embodiments, the nucleotide-based characteristic is an indication of methylation, is an alphanumeric description of a genomic location in which the corresponding genetic variant is present, the genomic location selected from the group consisting of: an exon, an intron, a regulatory region, a splice site, a flanking region, a promoter region, and a region that codes for non-coding RNA, or is an alphanumeric description of a type of the corresponding genetic variant selected from the group consisting of: missense, nonsense, synonymous, insertion, deletion, and structural variation.

In some embodiments, the score-based characteristic is selected from the group consisting of: an allele frequency associated with the corresponding genetic variant, a SIFT score associated with the corresponding genetic variant, a PolyPhen-2 score associated with the corresponding genetic variant, a PolyPhen score associated with the corresponding genetic variant, and a PFAM associated with the corresponding genetic variant.

In some embodiments, the genome-based characteristic is selected from the group consisting of: a zygosity of the genome in which the corresponding genetic variant is present, a fractional allele frequency for the corresponding genetic variant in the genome in which the corresponding genetic variant is present, a phenotype of the genome in which the corresponding genetic variant is present, a demographic of the genome in which the corresponding genetic variant is present, and a clinical indication of the genome in which the corresponding genetic variant is present.

In some embodiments, the sample-specific characteristic is selected from the group consisting of: a read quality of the genome in which the corresponding genetic variant is present, and a read depth of the genome in which the corresponding genetic variant is present.

In some embodiments, the data structure module further is configured to cause the processor to digital representations of genetic variants within additional genomes, and for each genetic variant within each digital representation: to determine whether that genetic variant corresponds to a discrete data structure stored within the database; if that genetic variant is determined to correspond to a stored discrete data structure, to modify the corresponding stored discrete data structure to include a third data field comprising a unique alphanumeric identifier for the additional genome, and to store the modified discrete data structure within the database; and if that genetic variant is determined not to correspond to a stored discrete data structure, to convert the digital representation of that genetic variant into an additional discrete data structure uniquely corresponding to only that genetic variant, the additional discrete data structure comprising a first data field comprising a unique alphanumeric identifier for the corresponding genetic variant and a second data field comprising a unique alphanumeric identifier for the additional genome, and to store the additional discrete data structure within the database.

In some embodiments, the data structure module is configured to cause the processor to determine whether that genetic variant corresponds to a stored discrete data structure by performing steps comprising: generating a unique alphanumeric identifier for that genetic variant; and searching the first data fields of the existing discrete data structures stored within the database for a unique alphanumeric identifier that matches the unique alphanumeric identifier for that genetic variant.

In some embodiments, the resulting plurality of discrete data structures includes at least 10 million discrete data structures. The system can be a personal computer.

Under another aspect of the present invention, a computer-based system for generating database means for use in analyzing genetic variants is provided. The system can include processing means; and memory means in operable communication with the processor, the memory means storing data structure means for causing the processor to receive a digital representation of genetic variants within a first genome, and for each genetic variant within the digital representation: to convert the digital representation of that genetic variant within the a discrete data structure uniquely corresponding to only that genetic variant, the data structure comprising a first data field comprising a unique alphanumeric identifier for the corresponding variant and a second data field comprising a unique alphanumeric identifier for the first genome; and to store the discrete data structure in the database means.

Under another aspect of the present invention, a memory for storing data for access by an application program being executed on a data processing system is provided. The memory can include a genome mask stored in said memory and comprising a plurality of chromosome masks, each chromosome mask corresponding to a chromosome and comprising an array of bits, each bit corresponding to a base pair position in the corresponding chromosome, wherein only bits corresponding to positions of a nucleic acid characteristic include a flag.

The nucleic acid characteristic can be selected from the group consisting of: a gene-based characteristic, a nucleotide-based characteristic, a score-based characteristic, a genome-based characteristic, and a sample-specific characteristic.

In some embodiments, the gene-based characteristic is selected from the group consisting of: a name or identifier of a gene in which the corresponding genetic variant is present, a biochemical pathway in which the genetic variant or a gene in which it is present is known to participate, an indication of whether the corresponding genetic variant is listed in a particular curated data source, a cancer type in which the corresponding genetic variant or a gene in which it is present is involved, a disease phenotype in which the corresponding genetic variant or a gene in which it is present is involved, a gene that is known to be expressed that contains the genetic variant, a dbSNP associated with the corresponding genetic variant, and a transcription factor that is at least partially encoded by the genetic variant.

In some embodiments, the nucleotide-based characteristic is an indication of methylation, is an alphanumeric description of a genomic location in which the corresponding genetic variant is present, the genomic location selected from the group consisting of: an exon, an intron, a regulatory region, a splice site, a flanking region, a promoter region, and a region that codes for non-coding RNA, or is an alphanumeric description of a type of the corresponding genetic variant selected from the group consisting of: missense, nonsense, synonymous, insertion, deletion, and structural variation.

In some embodiments, the score-based characteristic is selected from the group consisting of: an allele frequency associated with the corresponding genetic variant, a SIFT score associated with the corresponding genetic variant, a PolyPhen-2 score associated with the corresponding genetic variant, a PolyPhen score associated with the corresponding genetic variant, and a PFAM associated with the corresponding genetic variant.

In some embodiments, the genome-based characteristic is selected from the group consisting of: a zygosity of the genome in which the corresponding genetic variant is present, a fractional allele frequency for the corresponding genetic variant in the genome in which the corresponding genetic variant is present, a phenotype of the genome in which the corresponding genetic variant is present, a demographic of the genome in which the corresponding genetic variant is present, and a clinical indication of the genome in which the corresponding genetic variant is present.

In some embodiments, the sample-specific characteristic is selected from the group consisting of: a read quality of the genome in which the corresponding genetic variant is present, and a read depth of the genome in which the corresponding genetic variant is present.

Under yet another aspect of the present invention, a computer-based method for analyzing genetic variants within a plurality of genomes is provided. The method can include submitting a query term to a database storing a plurality of discrete data structures within a memory, each data structure uniquely corresponding to only one of the genetic variants present within the plurality of genomes, each data structure comprising a first data field comprising a unique alphanumeric identifier for the corresponding genetic variant and a second data field comprising a unique alphanumeric identifier for a genome in which the corresponding genetic variant is present, the query term comprising a unique alphanumeric identifier for at least one genome of the plurality of genomes and an operation to be performed on that genome; searching the second data fields of the plurality of data structures stored in the database for unique alphanumeric identifiers that match the query term and satisfy the operation; and generating an output representing the result of performing the search, wherein at least one of the discrete data structures comprises a third data field comprising a unique alphanumeric identifier for an additional genome in which the corresponding genetic variant is present, wherein the query term comprises unique alphanumeric identifiers for two or more genomes of the plurality of genomes, wherein the output comprises a list or graphical representation of genetic variants that are shared between the two or more genomes or that are unique to only one of the two or more genomes, wherein at least one of the discrete data structures further comprises a fourth data field storing an alphanumeric representation of a nucleic acid characteristic, wherein the nucleic acid characteristic is selected from the group consisting of: a gene-based characteristic, a nucleotide-based characteristic, a score-based characteristic, a genome-based characteristic, and a sample-specific characteristic, and wherein the plurality of discrete data structures includes at least 10 million discrete data structures.

Under another aspect of the present invention, a computer-based system for analyzing genetic variants within a plurality of genomes is provided. The system can include a processor; and a memory in operable communication with the processor, the memory storing a query module configured to cause the processor to submit a query term to a database storing a plurality of data structures, each data structure uniquely corresponding to only one of the genetic variants present within the plurality of genomes, each data structure comprising a first data field comprising a unique alphanumeric identifier for the corresponding genetic variant and a second data field comprising a unique alphanumeric identifier for a genome in which the corresponding genetic variant is present, the query term comprising a unique alphanumeric identifier for at least one genome of the plurality of genomes and an operation to be performed on that genome, the query module further being configured to cause the processor to search the data fields of the plurality of data structures stored in the database for unique alphanumeric identifiers that match the query term and satisfy the operation, the query module further being configured to cause the processor to generate an output representing the result of performing the search, wherein at least one of the discrete data structures comprises a third data field comprising a unique alphanumeric identifier for an additional genome in which the corresponding genetic variant is present, wherein the query term comprises unique alphanumeric identifiers for two or more genomes of the plurality of genomes, wherein the output comprises a list or graphical representation of genetic variants that are shared between the two or more genomes or that are unique to only one of the two or more genomes, wherein at least one of the discrete data structures further comprises a fourth data field storing an alphanumeric representation of a nucleic acid characteristic, wherein the nucleic acid characteristic is selected from the group consisting of: a gene-based characteristic, a nucleotide-based characteristic, a score-based characteristic, a genome-based characteristic, and a sample-specific characteristic, and wherein the plurality of discrete data structures includes at least 10 million discrete data structures.

Under still another aspect of the present invention, a memory for storing data for access by an application program being executed on a data processing system is provided. The memory can include a plurality of discrete data structures stored in said memory and including information resident in a database used by said application program, each data structure uniquely corresponding to only one genetic variant present in a plurality of genomes, each data structure comprising a first data field uniquely comprising a unique alphanumeric identifier for the corresponding genetic variant and a second data field comprising a unique alphanumeric identifier for a genome in which that genetic variant is present, wherein at least one of the discrete data structures comprises a third data field comprising a unique alphanumeric identifier for an additional genome in which the corresponding genetic variant is present, wherein at least one of the discrete data structures further comprises a fourth data field storing an alphanumeric representation of a nucleic acid characteristic, wherein the nucleic acid characteristic is selected from the group consisting of: a gene-based characteristic, a nucleotide-based characteristic, a score-based characteristic, a genome-based characteristic, and a sample-specific characteristic, and wherein the plurality of discrete data structures includes at least 10 million discrete data structures.

Under another aspect of the present invention, a computer-based method for generating a database for use in analyzing genetic variants is provided. The method can include receiving a digital representation of genetic variants within a first genome, and for each genetic variant within the digital representation: determining whether that genetic variant corresponds to an existing discrete data structure within a plurality of existing discrete data structures stored within a database, each existing discrete data structure uniquely corresponding to only one genetic variant present within at least one other genome, each existing discrete data structure comprising a first data field comprising a unique alphanumeric identifier for the corresponding genetic variant and a second data field comprising a unique alphanumeric identifier for the at least one other genome; if that genetic variant is determined to correspond to an existing data structure, modifying the corresponding existing discrete data structure to include a third data field comprising a unique alphanumeric identifier for the first genome, and storing the modified existing discrete data structure within the database; and if that genetic variant is determined not to correspond to an existing discrete data structure, converting the digital representation of that genetic variant into an additional discrete data structure uniquely corresponding to only that genetic variant, the additional discrete data structure comprising a first data field comprising a unique alphanumeric identifier for the corresponding genetic variant and a second data field comprising a unique alphanumeric identifier for the first genome, and storing the additional discrete data structure within the database, wherein determining whether that genetic variant corresponds to an existing discrete data structure comprises: generating a unique alphanumeric identifier for that genetic variant; and searching the first data fields of the existing discrete data structures stored within the database for a unique alphanumeric identifier that matches the unique alphanumeric identifier for that genetic variant, wherein at least one of the existing discrete data structures comprises one or more additional data fields comprising one or more unique alphanumeric identifiers for additional genomes in which the corresponding genetic variant is present, wherein the digital representation of the first genome is a variant call format (VCF) file, a genome variation format (GVF) file, a general feature format (GFF) file, a general transfer format (GTF) file, a sequence alignment data (SAM) file, a binary sequence alignment data (BAM) file, a BED file, a FASTA file, or a FASTQ file, wherein the method further comprises generating within the additional discrete data structure a fourth data field storing an alphanumeric representation of a nucleic acid characteristic, wherein the fourth data field is generated by performing steps comprising: obtaining a genome mask comprising a plurality of chromosome masks, each chromosome mask corresponding to a chromosome and comprising an array of bits, each bit corresponding to a base pair position in the corresponding chromosome, wherein only bits corresponding to a position of the nucleic acid characteristic include a flag; determining whether a bit within the genome mask that corresponds to the chromosome and position of the corresponding genetic variant includes a flag; if the bit is determined to include a flag, submitting a query to the curated data source requesting information about the nucleic acid characteristic at the chromosome and position corresponding to that bit, and storing the query result in the fourth data field, wherein the nucleic acid characteristic is selected from the group consisting of: a gene-based characteristic, a nucleotide-based characteristic, a score-based characteristic, a genome-based characteristic, and a sample-specific characteristic.

Under yet another aspect of the present invention, a computer-based system for generating a database for use in analyzing genetic variants is provided. The system can include a processor; and a memory in operable communication with the processor, the memory storing a data structure module configured to cause the processor to receive a digital representation of genetic variants within a first genome, and for each genetic variant within the digital representation: to determine whether that genetic variant corresponds to an existing discrete data structure within a plurality of existing discrete data structures stored within a database, each existing discrete data structure uniquely corresponding to only one genetic variant present within at least one other genome, each existing discrete data structure comprising a first data field comprising a unique alphanumeric identifier for the corresponding genetic variant and a second data field comprising a unique alphanumeric identifier for the at least one other genome; if that genetic variant is determined to correspond to an existing data structure, to modify the corresponding existing discrete data structure to include a third data field comprising a unique alphanumeric identifier for the first genome, and to store the modified existing discrete data structure within the database; and if that genetic variant is determined not to correspond to an existing discrete data structure, to convert the digital representation of that genetic variant into an additional discrete data structure uniquely corresponding to only that genetic variant, the additional discrete data structure comprising a first data field comprising a unique alphanumeric identifier for the corresponding genetic variant and a second data field comprising a unique alphanumeric identifier for the first genome, and to store the additional discrete data structure within the database, wherein determining whether that genetic variant corresponds to an existing discrete data structure comprises: generating a unique alphanumeric identifier for that genetic variant; and searching the first data fields of the existing discrete data structures stored within the database for a unique alphanumeric identifier that matches the unique alphanumeric identifier for that genetic variant, wherein at least one of the existing discrete data structures comprises one or more additional data fields comprising one or more unique alphanumeric identifiers for additional genomes in which the corresponding genetic variant is present, wherein the digital representation of the first genome is a variant call format (VCF) file, a genome variation format (GVF) file, a general feature format (GFF) file, a general transfer format (GTF) file, a sequence alignment data (SAM) file, a binary sequence alignment data (BAM) file, a BED file, a FASTA file, or a FASTQ file, the memory further storing a decorator module configured to cause the processor to generate within the additional discrete data structure a fourth data field by performing steps comprising: obtaining a genome mask comprising a plurality of chromosome masks, each chromosome mask corresponding to a chromosome and comprising an array of bits, each bit corresponding to a base pair position in the corresponding chromosome, wherein only bits corresponding to a position of the nucleic acid characteristic include a flag; determining whether a bit within the genome mask that corresponds to the chromosome and position of the corresponding genetic variant includes a flag; if the bit is determined to include a flag, submitting a query to the curated data source requesting information about the nucleic acid characteristic at the chromosome and position corresponding to that bit, and storing the query result in the fourth data field, wherein the nucleic acid characteristic is selected from the group consisting of: a gene-based characteristic, a nucleotide-based characteristic, a score-based characteristic, a genome-based characteristic, and a sample-specific characteristic.

Under another aspect of the present invention, a computer-based method for generating a database for use in analyzing genetic variants is provided. The method can include: converting a digital representation of genetic variants within a first genome into a plurality of discrete data structures, each data structure uniquely corresponding to only one of the genetic variants present in the first genome, each data structure comprising a first data field comprising a unique alphanumeric identifier for the corresponding variant and a second data field comprising a unique alphanumeric identifier for the first genome; and storing the plurality of discrete data structures in a database in a memory, wherein the digital representation of the first genome is a variant call format (VCF) file, a genome variation format (GVF) file, a general feature format (GFF) file, a general transfer format (GTF) file, a sequence alignment data (SAM) file, a binary sequence alignment data (BAM) file, a BED file, a FASTA file, or a FASTQ file, the method further comprising generating within the discrete data structure a third data field storing an alphanumeric representation of a nucleic acid characteristic, wherein the third data field is generated by performing steps comprising: obtaining a genome mask comprising a plurality of chromosome masks, each chromosome mask corresponding to a chromosome and comprising an array of bits, each bit corresponding to a base pair position in the corresponding chromosome, wherein only bits corresponding to a position of the nucleic acid characteristic include a flag; determining whether a bit within the genome mask that corresponds to the chromosome and position of the corresponding genetic variant includes a flag; if the bit is determined to include a flag, submitting a query to the curated data source information about the nucleic acid characteristic at the chromosome and position corresponding to that bit, and storing the query result in the third data field, wherein the nucleic acid characteristic is selected from the group consisting of: a gene-based characteristic, a nucleotide-based characteristic, a score-based characteristic, a genome-based characteristic, and a sample-specific characteristic, the method further comprising obtaining digital representations of genetic variants within a plurality of additional genomes, and for each genetic variant within each additional genome: determining whether that genetic variant corresponds to a discrete data structure stored within the database; if that genetic variant is determined to correspond to a stored discrete data structure, modifying the corresponding stored discrete data structure to include a third data field comprising a unique alphanumeric identifier for the first genome, and storing the modified discrete data structure within the database; and if that genetic variant is determined not to correspond to a stored discrete data structure, converting the digital representation of that genetic variant into an additional discrete data structure uniquely corresponding to only that genetic variant, the additional discrete data structure comprising a first data field comprising a unique alphanumeric identifier for the corresponding genetic variant and a second data field comprising a unique alphanumeric identifier for the first genome, and storing the additional discrete data structure within the database, wherein determining whether that genetic variant corresponds to a stored discrete data structure comprises: generating a unique alphanumeric identifier for that genetic variant; and searching the first data fields of the existing discrete data structures stored within the database for a unique alphanumeric identifier that matches the unique alphanumeric identifier for that genetic variant, and wherein the resulting plurality of discrete data structures includes at least 10 million discrete data structures.

Under another aspect of the present invention, a computer-based system for generating a database for use in analyzing genetic variants is provided. The system can include a processor; and a memory in operable communication with the processor, the memory storing a data structure module configured to cause the processor to receive a digital representation of genetic variants within a first genome, and for each genetic variant within the digital representation: to convert the digital representation of that genetic variant within the a discrete data structure uniquely corresponding to only that genetic variant, the data structure comprising a first data field comprising a unique alphanumeric identifier for the corresponding variant and a second data field comprising a unique alphanumeric identifier for the first genome; and to store the discrete data structure in a database in a memory, wherein the digital representation of the first genome is a variant call format (VCF) file, a genome variation format (GVF) file, a general feature format (GFF) file, a general transfer format (GTF) file, a sequence alignment data (SAM) file, a binary sequence alignment data (BAM) file, a BED file, a FASTA file, or a FASTQ file, wherein the memory further stores a decorator module configured to cause the processor to generate a third data field storing an alphanumeric representation of a nucleic acid characteristic by performing steps comprising: obtaining a genome mask comprising a plurality of chromosome masks, each chromosome mask corresponding to a chromosome and comprising an array of bits, each bit corresponding to a base pair position in the corresponding chromosome, wherein only bits corresponding to a position of the nucleic acid characteristic include a flag; determining whether a bit within the genome mask that corresponds to the chromosome and position of the corresponding genetic variant includes a flag; if the bit is determined to include a flag, submitting a query to the curated data source requesting information about the nucleic acid characteristic at the chromosome and position corresponding to that bit, and storing the query result in the third data field, wherein the nucleic acid characteristic is selected from the group consisting of: a gene-based characteristic, a nucleotide-based characteristic, a score-based characteristic, a genome-based characteristic, and a sample-specific characteristic, wherein the data structure module further is configured to cause the processor to receive digital representations of genetic variants within a plurality of additional genomes, and for each genetic variant within each additional genome: to determine whether that genetic variant corresponds to a discrete data structure stored within the database; if that genetic variant is determined to correspond to a stored discrete data structure, to modify the corresponding stored discrete data structure to include a third data field comprising a unique alphanumeric identifier for the first genome, and to store the modified discrete data structure within the database; and if that genetic variant is determined not to correspond to a stored discrete data structure, to convert the digital representation of that genetic variant into an additional discrete data structure uniquely corresponding to only that genetic variant, the additional discrete data structure comprising a first data field comprising a unique alphanumeric identifier for the corresponding genetic variant and a second data field comprising a unique alphanumeric identifier for the first genome, and to store the additional discrete data structure within the database, wherein the data structure module is configured to cause the processor to determine whether that genetic variant corresponds to a stored discrete data structure by performing steps comprising: generating a unique alphanumeric identifier for that genetic variant; and searching the first data fields of the existing discrete data structures stored within the database for a unique alphanumeric identifier that matches the unique alphanumeric identifier for that genetic variant, wherein the resulting plurality of discrete data structures includes at least 10 million discrete data structures.

Under another aspect of the present invention, a memory is provided for storing data for access by an application program being executed on a data processing system, comprising: a genome mask stored in said memory and comprising a plurality of chromosome masks, each chromosome mask corresponding to a chromosome and comprising an array of bits, each bit corresponding to a base pair position in the corresponding chromosome, wherein only bits corresponding to positions of a nucleic acid characteristic include a flag, wherein the nucleic acid characteristic is selected from the group consisting of: a gene-based characteristic, a nucleotide-based characteristic, a score-based characteristic, a genome-based characteristic, and a sample-specific characteristic.

BRIEF DESCRIPTION OF DRAWINGS

FIG. 1A schematically illustrates digital representations of a pair of exemplary genomes and genetic variants therein.

FIGS. 1B-1E schematically illustrate basic building blocks that can be used in the logical analysis of genetic variant data using genomic set theory.

FIGS. 1F-1H schematically illustrate application of the building blocks of FIGS. 1B-1E to identify relationships between genetic variants within the exemplary genomes of FIG. 1A.

FIGS. 2A-2D schematically illustrate discrete data structures corresponding to genetic variants within the exemplary genomes of FIG. 1A, according to some embodiments of the present invention.

FIG. 4A schematically illustrates digital representations of N exemplary genomes.

FIG. 4B schematically illustrates the use of previously known data structures to represent genetic variants within the N exemplary genomes of FIG. 4A.

FIGS. 5A-5D schematically illustrate intermediate data structures that can be formed during execution of the method of FIG. 3, according to some embodiments of the present invention.

FIG. 6 illustrates an exemplary genome mask for use in modifying data structures corresponding to genetic variants therein so as to include extrinsic information, according to some embodiments of the present invention.

FIG. 7 illustrates steps in a computer-based method of using a genome mask such as illustrated in FIG. 6 to modify data structures corresponding to genetic variants within genomes so as to include extrinsic information, according to some embodiments of the present invention.

FIG. 8 schematically illustrates the use of an exemplary genome mask during execution of the method of FIG. 7, according to some embodiments of the present invention.

FIG. 9 schematically illustrates an exemplary alternative genome mask, according to some embodiments of the present invention.

FIG. 10 illustrates steps in a computer-based method of generating a genome mask such as illustrated in FIG. 6, according to some embodiments of the present invention.

FIGS. 11A-11B schematically illustrate intermediate data structures that can be formed during execution of the method of FIG. 10, according to some embodiments of the present invention.

FIG. 12 schematically illustrates a discrete data structure representing an exemplary genetic variant and including intrinsic, extrinsic, and genomic information about that variant, according to some embodiments of the present invention.

FIGS. 13A-13R schematically illustrate genomic set representations of various query operations that can be applied to discrete data structures corresponding to genetic variants within a plurality of genomes, according to some embodiments of the present invention.

FIGS. 15A-15L schematically illustrate exemplary graphical user interfaces that can be generated during use of the computer-based system of FIG. 14.

DETAILED DESCRIPTION

Overview

Figure 3:
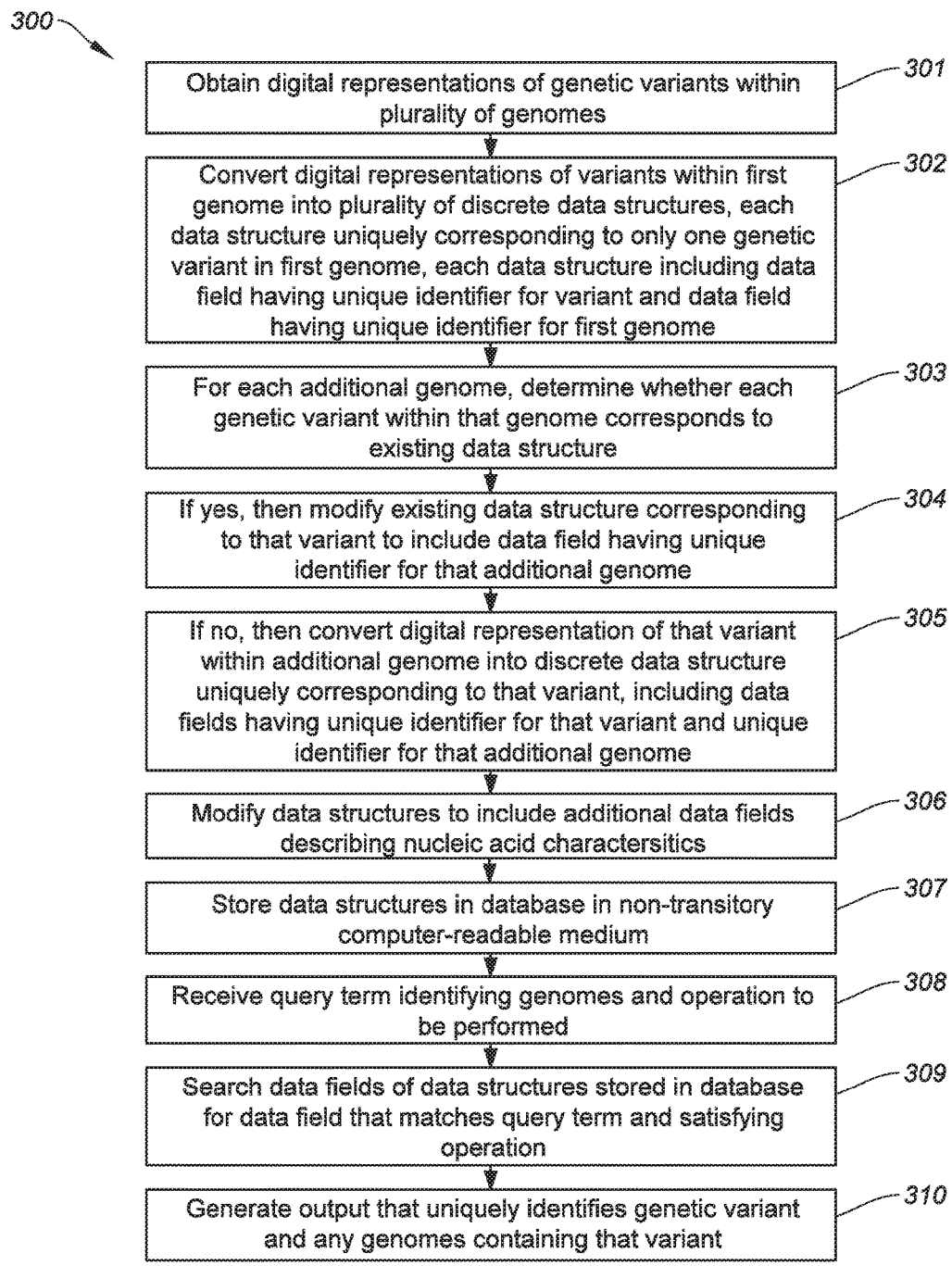
FIG. 3 illustrates steps in a computer-based method of analyzing a plurality of genomes based on discrete data structures corresponding to genetic variants therein, according to some embodiments of the present invention.

Embodiments of the present invention provide computer-based systems, methods, and data structures for use in analyzing genomes based on discrete data structures, each of which preferably uniquely represents a corresponding genetic variant. More specifically, the present systems, methods, and data structures are designed to facilitate the analysis and comparison of multiple genomes with high efficiency and with significantly less computational power and storage space than can be required in previously known methods of genomic analysis. Such efficiency is believed to derive, at least in part, from using the present systems and methods to convert a digital representation of genetic variants within a genome (such as a VCF file or other suitably formatted file) into a plurality of discrete data structures that respectively correspond to those genetic variants. Preferably, each resulting data structure uniquely corresponds only to a single genetic variant, and contains data fields having a unique alphanumeric identifier for that genetic variant and a unique alphanumeric identifier for that genome. Additionally, as noted above, the genomes of different individuals can include the same genetic variants as one another. Rather than generating an additional complete set of data structures for each additional genome to be analyzed, the present systems and methods instead can determine whether the genetic variants within that genome correspond to any existing data structures—that is, whether the additional genome shares a variant with a previously analyzed genome. If so, then the data structure corresponding to that variant can be modified to include a data field having a unique alphanumeric identifier for that additional genome. In essence, the resulting set of data structures deconstructs entire genomes into a plurality of discrete computational entities, each of which uniquely identifies the corresponding variant and any genomes that contain that variant. Note that because the genomes can share genetic variants with one another, and thus can share data structures, the number of data structures can increase sub-linearly with the number of genomes analyzed.

The resulting set of discrete data structures—which can represent all or substantially all of the genetic variants within all of the genomes thus analyzed—can be stored in a searchable database. For example, the searchable database can include 1000 or more discrete data structures, or 10,000 or more discrete data structures, or 100,000 or more discrete data structures, or 1 million or more discrete data structures, or 10 million or more discrete data structures, or can include 20 million or more discrete data structures, or can include 30 million or more discrete data structures, or can include 40 million or more discrete data structures, or can include 50 million or more discrete data structures, or even can include 100 million or more discrete data structures. Should a user wish to analyze whether a given set of genomes share any variants with one another, or have any variants that differ from one another, the user can submit to the database a query that identifies the genomes and an operation to be performed on the genomes, in a manner analogous to that described above with reference to FIGS. 1F-1H. However, rather than loading and then comparing the genomic sequences or the variant call files (VCFs) of the genomes identified by the user—which would require a large amount of computational memory and power—the database instead can simply can be searched for data structures having alphanumeric data fields that match the query terms, and can thereafter or concurrently perform the operation defined in the query. For example, if the user wishes to identify genetic variants shared by genomes 1 and 2 illustrated in FIG. 1A, the database can relatively rapidly search for data structures that include data fields having alphanumeric identifiers for both genomes 1 and 2, and can output a list (or other representation) of the variants corresponding to those data structures. Alternatively, if the user wishes to identify variants that are unique to genome 1 relative to genome 2, the database can relatively rapidly search for data structures that include data fields having an alphanumeric identifier for genome 1, but not for genome 2, and can output a list (or other representation) of the variants corresponding to those data structures. Note that the amount of computational power and memory that can be needed for such queries can increase sublinearly, and indeed may not even increase significantly, with the number of genomes to be analyzed or the type of operation to be performed. Accordingly, the present queries can be performed using a personal computer, rather than a massively parallel system such as may be required in previously known analytical methods.

The present data structures also can be "decorated," i.e., annotated, so as to include supplemental information about the variant, which information is referred to herein as a "nucleic acid characteristic," e.g., a gene-based characteristic, a nucleotide-based characteristic, a score-based characteristic, a genome-based characteristic, or a sample-specific characteristic such as those described in greater detail herein. For example, each data structure can include data fields with alphanumeric identifiers for the position, chromosome, reference allele, and variant allele, which can be considered to be intrinsic information about the variant and can be obtained from the digital representations of the genomes, e.g., from VCF files or other suitably formatted files for those genomes. Or, for example, each data structure can include data fields with alphanumeric identifiers of the respective zygosity and read quality or read depth of the genomes containing the corresponding genetic variant, which similarly can be obtained from the digital representations of the genomes. The zygosity of the genome containing the genetic variant can be considered to be a "genome-based characteristic," because it relates to a property of the genome that contains the variant, while the read quality or read depth of the genome containing the genetic variant can be considered to be a "sample-specific characteristic," because it relates to a property of the genomic sample that was analyzed. More specifically, the read depth of a genome means the total number of bases sequenced at a given reference base position, such as described online at www.illumina.com/truseq/quality_101/coverage/coverage_distribution.ilmn; and the read quality of a genome is an estimate of the accuracy of calling a nucleotide base at each position, and therefore the accuracy of the read sequence, such as described online at maq.sourceforge.net/qual.shtml.

Each data structure also can be annotated so as to include extrinsic information such as any genes in which the variant is known to be present, which can be considered a "gene-based characteristic," an indication of whether the variant is in an exon, which can be considered a "nucleic acid characteristic," a SIFT or PolyPhen or PolyPhen-2 score for the variant, which can be considered a "score-based characteristic," and the like. Such information can be obtained by submitting queries to curated data sources, and storing the query results, which preferably are alphanumeric, in additional data fields in the corresponding data structures. So as to improve the computational efficiency of performing such queries, the present systems and methods can utilize a data structure referred to herein as a "genome mask" to submit queries only for those regions of an individual's genome that are known to contain extrinsic information, e.g., a gene, an exon, or the like. As described in greater detail below, the genome mask can contain an array of bits that respectively correspond to positions of nucleic acids in the genome. Preferably, bits within the mask contain a flag such as the value "1" only if the nucleic acid position corresponding to that bit is known to fall within a region corresponding to a gene, an exon, or the like. For each data structure corresponding to a genetic variant, a query can be submitted to a curated data source based on the mask, requesting the name or identifier of the gene, an indication of whether the region is within an exon, or the like, at the nucleic acid position corresponding to that bit. The result of the query can be stored in a corresponding data field in the data structure. For example, if a genetic variant is determined to be within a gene, then the alphanumeric name or identifier of that gene can be stored in the data structure corresponding to that variant. Or, for example, if a genetic variant is determined to be positioned within an exon, then an alphanumeric designation such as "exon: yes" or the like can be stored in the data structure corresponding to that variant. Note that the use of the genome mask obviates the need to submit queries for regions of an individual's genome that are not known to include a gene or other extrinsic information—which can constitute 90% or more of the genome—thus significantly reducing the amount of computational power that otherwise can have been required to annotate the data structure. Accordingly, such annotation can be performed using a personal computer rather than a massively parallel computing system.

The annotations describing nucleic acid characteristics that can be stored within data fields of the present data structures can be used to provide a user with significantly enhanced information about the corresponding genetic variants than otherwise can be available based solely on a comparison of the sequences or VCF files, or other suitably formatted files, of genomes. Indeed, such annotations can be considered to distill the vast amount of information contained within numerous curated data sources into readily searchable alphanumeric data fields. Such annotations can be used in combination with query operations so as to help the user to more quickly identify unique or shared genetic variants that can be of particular interest to the problem he is trying to solve. For example, continuing with the above-mentioned illustrative operations on genomes 1 and 2, the user can further specify in the query term that only genetic variants known to be within genes should be outputted. The output thus can include only data structures that include a data field with an alphanumeric name or identifier of a gene. In this regard, note that the greater number of such annotation-based query terms that the user applies, and the greater number of genomes to be compared, the more data structures the database can rapidly exclude as irrelevant, thus leading to a more rapid return of results to the user.

Indeed, because of the many computational efficiencies provided by the systems, methods, and data structures herein, it has been observed that queries performing operations on multiple genomes and applying any desired combination of annotation-based query terms can return results to the user on the order of tens of milliseconds or less, using a personal computer such as a dual processor Macintosh computer with a relatively small amount of memory, e.g., 8-16 GB of memory. As such, the user conveniently can submit and receive the results of multiple queries in a single session, and the marginal cost in time and money of performing any given query is negligible. Accordingly, the present systems and methods can facilitate a greatly increased pace of genomic analysis. In contrast, as evidenced by the above-noted press release, previously known methods of analyzing genomes can require specialized, massively parallel computer equipment with dozens of processors and hundreds of GB of memory, and the anticipated time for performing each query is not stated. Of course, implementing the present systems and methods on specialized or high power computer equipment can provide even greater speed.

First, an illustrative pair of discrete data structures corresponding to genetic variants within an exemplary set of genomes will be described. Then, a computer-based method for generating such data structures, and intermediate data structures that can be formed during such a method, will be described. Computer-based methods for generating and using genome masks to modify such data structures, and intermediate data structures that can be formed during such methods, then will be described. Exemplary operations that readily can be performed with high computational efficiency using the present data structures then will be described. An exemplary computer system for use in generating, modifying, storing, and querying the present data structures, and exemplary graphical user interfaces that can be generated during use of such a system, then will be described. Lastly, some exemplary genomic analyses that were performed using the systems, methods, and data structures provided herein will be described.

Discrete Data Structures Corresponding to Genetic Variants

Embodiments of the present invention provide data structures that are discrete from one another, and that uniquely correspond to genetic variants that are present in one or more genomes. Each of the data structures preferably includes a data field that includes a unique alphanumeric identifier for the genetic variant to which the data structure corresponds, and a data field that includes a unique alphanumeric identifier for each genome that has been identified as including that genetic variant. Accordingly, the data structures readily can be searched for one or more genomes that include the corresponding variants, based on a query that includes a unique alphanumeric identifier for such genomes. As described in greater detail herein, the data structures also can include data fields that store information that is intrinsic or extrinsic to the genetic variant, e.g., that store one or more nucleic acid characteristics. The data structures can be stored in a memory, e.g., a non-volatile computer readable medium within a memory device, and preferably are organized within a searchable database therein.

FIGS. 2A and 2B illustrate a pair of discrete data structures that correspond to certain variants within exemplary genomes 1 and 2 described above with reference to FIG. 1A. Each data structure includes alphanumeric representations of nucleic acid characteristics, including a set of data fields corresponding to intrinsic information about the variant, a set of data fields corresponding to extrinsic information about the variant, and a set of data fields corresponding to genomic information about the variant. Specifically, the intrinsic information includes a data field that uniquely identifies the variant. For example, "variant ID: 1.5.g.a" in FIG. 2A corresponds to the SNP variant at position 5 in genome 1, in which the reference allele "g" is substituted with the variant allele "a." This data field includes the field name "variant ID" and the value "1.5.g.a." The field name identifies the type of information contained within the value, namely the unique identifier ("ID") of the variant. The value "1.5.g.a" is a hash or concatenation of alphanumeric fields corresponding to the chromosome (1), position (5), reference allele (g), and variant allele (a) of the variant, in which the punctuation "." delimits the different fields of the value from one another. Analogously, the data structure in FIG. 2B includes the data field "variant ID: 1.20.cat.atc," corresponding to the substitution at positions 20-22 of the reference allele "cat" with the variant allele "atc," in which the value "1.20.cat.atc" is a hash or concatenation of alphanumeric fields corresponding to the chromosome (1), the start position (20), reference allele (cat) and variant allele (atc). In this regard, note that a third data structure corresponding to the SNP at position 5 of genome 2 of the variant allele "c" for the reference allele "g" can be provided in a manner analogous to that shown in FIG. 2A, but is not illustrated. It should be appreciated that the data structures provided herein can include any suitable, unique, alphanumeric identifier for a given genetic variant. For example, the identifier can include hashes or concatenations that exclude punctuation or other symbols to delimit the fields from one another, that include additional fields such as a text-based indication of the type of variant (e.g., including "D" for deletion, "_" for SNP, or "S" for substitution), and the like. Preferably, the identifier for the variant excludes any information or identifier for any genome that can contain that variant, so that a given variant will have the same identifier regardless of the particular genome in which it is present.

As illustrated in FIGS. 2A-2B, the data fields corresponding to intrinsic information about the corresponding variant also can include alphanumeric identifiers for the position, chromosome, reference allele, or variant allele. As described in greater detail below with reference to FIG. 3, such intrinsic information can be determined based on the digital representations of the genomes being analyzed, e.g., can be extracted from a VCF file or other suitably formatted file, and stored within respective data fields of the data structure. Additionally, the data fields can include an alphanumeric identifier of the variant type, e.g., SNP in FIG. 2A or substitution ("SUB") in FIG. 2B. Such an alphanumeric identifier can be determined based on the digital representations of the genomes being analyzed, e.g., can be extracted or computationally inferred from a VCF file or other suitably formatted file and stored within a respective data field of the data structure.

The data fields corresponding to nucleic acid characteristics, if provided, preferably include an alphanumeric name or identifier of a gene in which the genetic variant is present, and optionally can include an alphanumeric name of a curated data source that provided that name or identifier. For example, it can be seen that the variant in FIG. 2A is annotated as being present in a gene named "E" and having gene identifier (ID) "6," the curated data source of which gene is GENBANK, and also is present in a gene named "H" and having gene ID "7," the curated data source of which gene is ENSEMBL. Or, for example, it can be seen that the variant in FIG. 2B is annotated as being present in a gene named "J" and having gene ID "8," the curated data source of which gene is GENBANK. In this regard, note that different curated data sources can define a given gene differently than one another, e.g., can use different names or numerical identifiers for that gene. The present data structures readily can accommodate such different gene definitions by providing additional data fields corresponding to each such definition and curated data source. For example, genomic researchers can identify new genes with which a given variant can be associated, and can either update an existing curated data source to reflect the new gene or even can generate a new curated data source storing information about that gene. The present data structures can include information about this new gene and the corresponding curated data source in a pair of additional data fields. Moreover, the content of a given curated data source can evolve over time, e.g., can have different versions over time. The present data structures readily can record the version of a particular data source from which extrinsic information was obtained, by providing an additional data field that stores information identifying the version of the curated data source, e.g., a version number or a date on which the extrinsic information was obtained from the curated data source. Then, if a user is interested only in a particular version number, date, range of version numbers, or range of dates, they can define the query term appropriately in a manner such as described further herein. Methods for incorporating nucleic acid characteristics into the present data structures based on curated data sources are described in greater detail below with reference to FIGS. 7 and 10.

In FIGS. 2A-2B, the data fields preferably also include a unique alphanumeric identifier for any genome that has been identified as containing that variant. For example, data structure 1.5.g.a illustrated in FIG. 2A includes a data field with a unique identifier for genome "1," representing that only genome 1 contains that variant. In comparison, data structure 1.20.cat.atc illustrated in FIG. 2B includes a data field with a unique identifier for genome "1" and another data field with a unique identifier for genome "2," indicating that both genomes 1 and 2 contain that variant. It should be understood that any suitable format can be used for the alphanumeric identifier for the genomes that contain that variant. For example, different sources of genomic sequence data, VCF files, or other suitably formatted files can use different naming conventions, and any unique alphanumeric identifier produced using any such naming convention suitably can be stored within a data structure. However, the unique alphanumeric identifier of the genome preferably is not a pointer to the genome, but instead is simply a text field containing a name, number, or mixture of letters and numbers that uniquely identifies the genome. In this regard, the data structures can be considered to be "denormalized" because they are discrete and self-contained, which can increase the computational speed with which the data structures can be queried, rather than referring to other information such as via a pointer to a genome, which can decrease the query speed. However, as noted below with reference to FIG. 12, one or more data fields of a data structure optionally can include a pointer to information that may not conveniently be stored as an alphanumeric text field.

Additionally, each of the data structures preferably contains a data field identifying the zygosity of the genome for the respective variant. For example, data structure 1.5.g.a illustrated in FIG. 2A includes a data field storing the alphanumeric identifier "1|1" representing that genome 1 is homozygous for the corresponding variant, that is, that both of the individual's alleles contain that variant. Data structure 1.20.cat.atc illustrated in FIG. 2B includes a data field storing the alphanumeric identifier "1|1" representing that genome 1 is homozygous for the corresponding variant, and a data field storing the alphanumeric identifier "0|1" representing that genome 2 is heterozygous for the corresponding variant, that is, that only one of the individual's alleles contain that variant. As described in greater detail below with reference to FIG. 3, such a nucleic acid characteristic can be determined based on the digital representations of the genomes being analyzed, e.g., can be extracted from a VCF file or other suitably formatted file and stored within a respective data field of the data structure. Additionally, note that a given data structure preferably does not store alphanumeric identifiers for any genomes that do not contain the corresponding variant, e.g., genomes for which an alphanumeric identifier "010" would be appropriate for that variant because neither of the individual's alleles contain that variant.

As described in greater detail below with reference to FIG. 12, the present data structures optionally can include additional data fields containing additional nucleic acid characteristics beyond that illustrated in FIGS. 2A-2B. Such nucleic acid characteristics can include, for example, nucleotide based characteristics such as alphanumeric characterizations of the genomic regions in which the variant is present, or sample-specific characteristics such as the quality of the genomic sequencing based upon which the variant is identified, or other characteristics such as described in greater detail herein.

Data structures corresponding to genetic variants, such as the exemplary data structures described above with reference to FIGS. 2A-2B or below with reference to FIG. 12, can be stored in any suitable format within a database in any suitable non-transitory computer-readable medium, such as described below with reference to FIG. 14. For example, the different data fields can be delimited from one another using any suitable format, such as tabs, commas, colons, spaces, pipes ("I") or the like. Additionally, any data fields that contain a delimiter (such as a colon or pipe) optionally can be enclosed with double quotes so as to reduce the risk of multiple data fields inadvertently being interpreted as together constituting a single data field; alternatively, all data fields optionally can be enclosed with double quotes. The data fields further can include field names or labels such as "chromosome" or "genome" and the like, such as shown in FIGS. 2A-2B; simplified field names such as "c" for chromosome or "g" for genome suitably can be used so as to reduce the number of bits required to store and process the field name. Depending on the particular type of database being used, including such field names within the data structures can reduce the amount of computational power needed to search those data structures, because it can allow the information within the data fields having the field names designated in the query to be searched selectively relative to other information within the data structures. However, it should be understood that labels or field names need not necessarily be included. For example, the information within data structures 1.5.g.a and 1.20.cat.atc of FIGS. 2A-2B suitably can be provided in a comma-delimited file without labels and without double quotes, such as respectively illustrated in FIGS. 2C-2D. However, it should be understood that other file formats that can be stored and queried within a searchable database suitably can be used. For example, the data structures can be provided as corresponding extensible markup language (XML) documents that respectively include different content fields corresponding to the above-noted data fields, or any other suitable format. For further information on the XML format, see Bray et al., eds., "Extensible Markup Language (XML) 1.0 (Fifth Edition), W3C Recommendation 26 Nov. 2008," available online at www.w3.org/TR/2008/REC-xml-20081126/.

The searchable database in which the data structures can be stored in a memory or computer-readable medium can be based on any suitable programming language, and can utilize any suitable method of storing, indexing and querying the discrete data structures stored therein. In one illustrative example, the database in which the discrete data structures are stored is based on Lucene, which is an open source information retrieval software library written in Java or other suitable programming language, and supported by the Apache Software Foundation (Delaware, United States). As is known in the art, a database based on Lucene can index documents added thereto based on the field names of data fields therein, and can accept a query syntax that identifies the field name to be searched and the value of that field name. For further details on query syntaxes for use with a Lucene database, please see Carlson, "Apache Lucene—Query Parser Syntax," The Apache Software Foundation (2006), available online at lucene.apache.org/core/old_versioned_docs/versions/2_9_1/queryparsersyntax.html.

In one illustrative example, a Lucene database containing data structures 1.5.g.a and 1.20.cat.atc can accept the following query term to identify the variants that are present in genome 1, e.g., to perform the "union" operation on the genome having unique alphanumeric identifier "1":

+(genome: 1)

where the symbol "+" means required, the term "genome" means to search data fields having the field name "genome," the value "1" is the value to be searched, here the unique alphanumeric identifier for genome 1, and the symbol ":" delimits the field name from the value to be searched. Based on the query, the database can identify both of data structures 1.5.g.a and 1.20.cat.atc as containing the value "1" in the genome field, and can output any suitable representation of the genetic variants corresponding to those data structures. For example, the database can output the labels for those data structures, can output the start and end positions, reference allele, variant allele, or variant type corresponding to those data structures, or can output a graphical representation of the position(s) of the variants within the genomes. Preferably, the database provides such output on a display screen that is either colocated with the database or is remote from the database such as described below with reference to FIG. 14, but the output alternatively can be stored in a memory or computer-readable medium.

Continuing with this example, the Lucene database also can accept the following query term to identify variants that are present in either genome 1 or in genome 2, e.g., to perform the "union" operation on the genomes having unique alphanumeric identifiers "1" and "2":

+(genome:1 genome:2).

Based on such a query, the database can identify data structure 1.5.g.a as containing the value "1" in the genome field and can identify data structure 1.20.cat.atc as containing the value "1" or the value "2" in the genome field, and provide an appropriate output indicating that both of the corresponding variants satisfy the query.

The Lucene database also can accept the following query syntax to identify variants that are present in genome 2 but not in genome 1, e.g., to perform the "differentiate" operation (G2 G1) illustrated in FIG. 1F on the genomes having unique alphanumeric identifiers "1" and "2":

+(+genome:2−genome: 1)

in which the symbol "−" means exclude. Based on such a query, the database can identify no data structure as satisfying the query because both of data structures 1.5.g.a and 1.20.cat.atc contain the value "1" in the genome field and thus would be excluded from the search results.

The Lucene database also can accept the following query syntax to identify variants that are present in genome 1 or in genome 2, but not in both genome 1 and genome 2, e.g., to perform the "symmetric differentiate" operation (G1 G2) U (G2 G1) illustrated in FIG. 1G on the genomes having unique alphanumeric identifiers "1" and "2":

+(+(+genome: 1−genome:2)+(+genome:2−genome: 1)).

Based on such a query, the database can identify data structure 1.5.g.a as satisfying the first portion of the query, "+(+genome: 1−genome:2)," because that data structure contains the value "1" but not the value "2" in the genome field, and can identify no data structure as satisfying the second portion of the query, +(+genome:2−genome: 1)," because there is no data structure that contains the value "2" but not the value "1" in the genome field. Accordingly, the result of the query is data structure 1.5.g.a, which the database suitably can output.

The Lucene database also can accept the following query syntax to identify variants that are present in both genome 1 and genome 2, e.g., to perform the "union" operation G1∩G2 illustrated in FIG. 1H on the genomes having unique alphanumeric identifiers "1" and "2":

+(+genome:1+genome:2).

Based on such a query, the database can identify data structure 1.20.cat.atc as containing both of the values "1" and "2" in the genome field, and can provide a suitable output. Other exemplary queries that can be performed on greater numbers of genomes are described in greater detail below with reference to FIGS. 13A-13R. It should be appreciated that other query syntaxes suitably can be used with other file formats or other types of databases, such as other Document-oriented databases (e.g., MongoDB) or relational databases based on structured query language (SQL).

From the foregoing examples, it can be seen that data structures such as described herein can include a relatively large amount of relevant information in a relatively small amount of space. For example, rather than expressing a genome as a sequence of 3 billion or more nucleic acids that contain various genetic variants, the genome instead can be expressed as a relatively short alphanumeric data field within discrete data structures corresponding to those variants. Additionally, those data structures can include a relatively low number of relatively short alphanumeric data fields that describe nucleic acid characteristics, e.g., intrinsic, extrinsic, or genomic information about the corresponding genetic variant. Accordingly, queries such as described above can be performed using relatively small amount of computational power, thus facilitating a significant increase in the speed of genomic analysis with significantly less computational power and memory than used in previously known methods. Exemplary graphical user interfaces that can facilitate queries such as described above are described further below with reference to Examples 2-5 and FIGS. 15A-15L.

Methods of Generating, Modifying, Storing, and Querying Data Structures Corresponding to Genetic Variants within Genomes Illustrative computer-based methods of generating, modifying, storing, and querying data structures that correspond to genetic variants within genomes now will be described with reference to FIG. 3.

Computer-based method 300 illustrated in FIG. 3 begins with obtaining digital representations of genetic variants within a plurality of genomes (step 301). Such digital representations can be in any of a variety of suitable formats. For example, as is known in the art, a given genome can be digitally represented as a sequence of letters respectively corresponding to different nucleic acids within the chromosomes of the genome. FIG. 4A schematically illustrates a digital representation of a plurality of genomes 1 . . . N (designated G1 . . . GN), each of which includes a sequence of letters corresponding to the nucleic acid sequence of each of the 1 . . . X chromosomes within the respective chromosome. Depicted are G1,C1 (SEQ ID NO: 1), G1,C2 (SEQ ID NO:4), G1,CX (SEQ ID NO:5), GN,C1 (SEQ ID NO:6), GN,C2 (SEQ ID NO:7), and GN,CX (SEQ ID NO:8). The genetic variants within the 1 . . . N genomes are denoted with bolding and underlining in FIG. 4A, in a manner analogous to that illustrated in FIG. 1A. As is mentioned above and as is known in the art, genetic sequences such as illustrated in FIG. 4A can be converted into a file format known as the variant call format (VCF) that expresses a genome as a list of the chromosomes, positions, reference alleles, alternate alleles, and zygosity of genetic variants, among other items of information, in a particular genome. Exemplary methods for analyzing the variants within a genome, and a description of information that can be included with a VCF file, can be found within the article entitled "An integrated map of genetic variation from 1,092 human genomes" authored by participants of the 1000 Genomes Project, Nature 491: 56-65 (November 2012), as well as the supplementary information thereof. Exemplary VCF files that were produced in conjunction with this article can be obtained online from The 1000 Genomes Project website at ftp://ftp.1000genomes.ebi.ac.uk/vol1/ftp/release or at ftp://ftp-trace.ncbi.nih.gov/1000genomes/ftp/. A definition of the VCF file format can be found in Danecek et al., "The variant call format and VCFtools," Bioinformatics 27(15): 2156-2158 (Jun. 7, 2011).

It should be noted, however, that the digital representation of the variants obtained in step 301 can have any suitable file format. In addition to VCF, other exemplary file formats that can be used include, but are not limited to, genome variation format (GVF), general feature format (GFF), general transfer format (GTF), sequence alignment data (SAM), binary sequence alignment data (BAM), BED, FASTA, and FASTQ. Information about the GVF format can be obtained online at www.sequenceontology.org/resources/gvf.html. Information about the GFF format can be obtained online from the Wellcome Trust Sanger Institute at www.sanger.ac.uk/resources/software/gff/spec.html. Additional information about the GFF format and information about the GTF format may be obtained online from uswest.ensembl.org/info/website/upload/gff.html. Information about the SAM and BAM formats can be obtained online from samtools.sourceforge.net/. Information about the BED, FASTA, and BAM formats may be obtained online from www.broadinstitute.org/igv/book/export/html/16. Information about the FASTQ format can be obtained online from illumina.ucr.edu/ht/documentation/file-formats or maq.sourceforge.net/fastq.shtml. Preferably, the digital representation of the variants includes at least the chromosome, location, reference allele, and alternate allele of a plurality of variants of an individual.

In preferred embodiments, step 301 of method 300 includes obtaining a VCF file for each of the 1 . . . N genomes to be analyzed. FIG. 4B illustrates a simplified version of exemplary VCF files that can be obtained from the above-noted 1000 Genomes Project website for genomes 1 . . . N (designated G1 . . . GN in FIG. 4B). The VCF file for each genome can be seen to include identifiers for the chromosome ("#Chrom") and position ("Pos") thereon at which each variant was found, e.g., at chromosome 1, position 5 for the first variant listed in genome 1's VCF file. The VCF file for each genome also can be seen to include an identifier for a reference allele ("Ref") and an alternate allele ("Alt") for each variant, e.g., "g" and "a" respectively for the first variant listed in genome 1's VCF file. Additionally, the VCF file can include the zygosity ("Format") of the genome for that allele, using the notation 1/1 to designate homozygous and 0/1 to designate heterozygous, e.g., 1/1 for the first variant listed in genome 1's VCF file. The different information in the VCF file can be delimited from one another using tabs or other suitable delimiters. It should be understood that method 300 can include obtaining digital representations of genetic variants within genomes in suitable file formats other than VCF. Preferably, any such digital representation can include information uniquely identifying the reference allele and the variant allele.

Method 300 further can include converting the digital representations of the variants within a first genome of the plurality of genomes into a plurality of discrete data structures (step 302). Preferably, each data structure uniquely corresponds to only one genetic variant within the first genome, and preferably includes a first data field having a unique identifier for the corresponding variant and a second data field having a unique identifier for the corresponding genome. Such a conversion step can include a plurality of substeps. For example, the conversion step can include identifying within the digital representation of the variants within the first genome an alphanumeric field that identifies the first genome, as well as alphanumeric fields respectively describing a chromosome, a position along that chromosome, a reference allele, and a variant allele corresponding to each genetic variant. Preferably, the digital representation of the first genome has a known format, so that the different pieces of information readily can be identified based on their positions within the digital representation.

A data structure then can be generated, optionally in a step-wise manner, based on the identified alphanumeric fields. For example, FIG. 5A illustrates a pair of intermediate data structures respectively labeled "Variant Data 1" and "Genome Data 1" that are based on information identified within the digital representation of the first genome (in this example, the VCF file for genome 1), that can be generated concurrently or sequentially, and that preferably are discrete from one another. It should be understood that labels such as "Variant Data 1" and "Genome Data 1" need not necessarily be included in intermediate data structures such as illustrated in FIG. 5A, but instead are intended to assist the reader in understanding the roles of the respective, preferably discrete data structures.

The intermediate data structure labeled "Variant Data 1" includes a data field storing a unique alphanumeric identifier for the corresponding variant. This data field can be generated based on the identified alphanumeric fields respectively describing the chromosome, position, reference allele, and variant allele for the corresponding variant listed in the digital representation, in the illustrated example "1.5.g.a." For example, these different fields can be computationally hashed or concatenated with one another in any suitable format to generate an alphanumeric string that preferably uniquely identifies this particular variant relative to all other variants, such as described further above with reference to FIGS. 2A-2B. A data structure having a data field can be generated, e.g., instantiated with empty values, and the alphanumeric identifier of the variant then can be stored within that data field. Preferably, the data field thus generated also includes a field name such as "variant ID" or "v," which can facilitate subsequent queries as noted elsewhere herein. Other data fields optionally also can be generated within the intermediate data structure and used to store intrinsic or extrinsic information about the corresponding genetic variant, e.g., information that was previously identified within the digital representation of the first genome, or that is identified based on curated data sources such as described in greater detail below with reference to step 306 of method 300. In one example, the VCF or other suitably formatted file for the first genome can not necessarily include the end position or the type of a given variant, but such information can be computationally inferred from the information within the file and stored in corresponding data fields within the intermediate data structure.

The intermediate data structure labeled "Genome Data 1" illustrated in FIG. 5A can be generated during one exemplary implementation of step 302 by generating data fields that uniquely identify the genome and one of the genetic variants contained by that genome. For example, as noted above with reference to an earlier substep, the method can include identifying within the digital representation of the variants within the first genome an alphanumeric identifier of the first genome, e.g., the numeral "1" within the VCF or other suitably formatted file for genome 1. This alphanumeric identifier can be used without alteration as the unique alphanumeric identifier of the genome and stored within one of the data fields of the intermediate data structure labeled "Genome Data 1." Alternatively, if this alphanumeric identifier does not uniquely identify the first genome, or if such an identifier is absent from the digital representation of the variants within the first genome, a unique identifier for the first genome instead can be generated, e.g., by generating any suitable combination of numbers, letters, or other characters based upon which the first genome can uniquely be identified. Preferably, the data field thus generated also includes a field name such as "genome" or "g" so as to facilitate subsequent queries. Additionally, the unique alphanumeric identifier of the variant contained by the first genome, e.g., "1.5.g.a," which can be generated as described above can be stored within the intermediate data structure labeled "Genome Data 1." Additional nucleic acid characteristics further can be stored in data fields of the intermediate data structure labeled "Genome Data 1." For example, as noted above, a digital representation of variants within a given genome, such as a VCF or other suitably formatted file, can include an alphanumeric identification of the genome's zygosity for each genetic variant. Such an alphanumeric identification can be identified within the digital representation and then stored within a data field generated within the corresponding intermediate data structure, preferably with a field name such as "zygosity" or "z" so as to facilitate querying that field. The zygosity of the genome for the variant can be considered to be a genome-based characteristic of the variant. The genome's VCF or other suitably formatted file further can include information reflecting the confidence with which each variant is identified, such as the "read quality" and "read depth," which can be considered to be sample-specific characteristics of the variant. Such information can be identified within the VCF or other suitably formatted file and then stored in additional data fields within the data structure.

Such a process of generating intermediate data structures can be repeated for each other genetic variant within the digital representation of the variants within the first genome. For example, for the second variant listed within the exemplary VCF file for the first genome illustrated in FIG. 4B, "Variant Data 2" and "Genome Data 2" intermediate data structures such as illustrated in FIG. 5B can be generated that respectively have data fields analogous to those described above for "Variant Data 1" and "Genome Data 1." It can be seen that "Genome Data 2" is similar to "Genome Data 1" in that both data structures include the unique alphanumeric identifier "1" for the genome, but is different in that "Genome Data 1" includes the unique alphanumeric identifier "1.5.g.a" corresponding to the first listed variant, while "Genome Data 2" includes the unique alphanumeric identifier "1.20.cat.atc" Corresponding pairs of intermediate data structures analogously can be generated for each other genetic variant within the digital representation of the variants within the first genome. Within each pair, it can be seen that the "Variant Data" data structure stores intrinsic information about the variant, including the unique alphanumeric identifier of the variant, but no information about the genome containing that variant, while the "Genome Data" data structure stores genomic information about the genome containing that variant, as well as the unique identifier of the variant.

Intermediate data structures such as those labeled "Variant Data 1" and "Genome Data 1" illustrated in FIG. 5A or those labeled "Variant Data 2" and "Genome Data 2" can be stored separately from one another, preferably in random access memory of the computer system performing the processing such as described further below with reference to FIG. 14, and subsequently can be merged together in a subsequent processing step. Specifically, the "Variant Data" and "Genome Data" intermediate data structures can be matched together by comparing the unique alphanumeric identifiers of the variants that are stored within the intermediate data structures to one another. Based on such a comparison, any intermediate data structures that are determined to include the same unique alphanumeric identifier of the variant as one another are assembled together to form a single data structure such as illustrated in FIGS. 2A-2B or, for formats that exclude field names, such as illustrated in FIGS. 2C-2D. The resulting data structure subsequently can be "decorated," i.e., annotated, so as to include extrinsic information about the corresponding genetic variant, such as described further below with reference to step 306 of method 300 illustrated in FIG. 3. Alternatively, the "Variant Data" intermediate data structures can be decorated in an analogous manner as described below with reference to step 306 before assembling those data structures together with the corresponding "Genome Data" intermediate data structures. That is, step 306, described in greater detail below, can be performed at any suitable time during the execution of method 300.

Additionally, it should be noted that intermediate data structures such as the "Variant Data" and "Genome Data" structures described above need not necessarily be generated separately from one another and later merged together. Instead, in some embodiments, a single data structure that contains intrinsic and genomic data about a variant can be generated. For example, unique alphanumeric identifiers can be generated for the corresponding genetic variant and first genome in a manner such as described above, and can be stored in respective data fields of a single data structure. That data structure subsequently can be "decorated" using step 306 of method 300. Other suitable computer-based methods of generating the present data structures alternatively can be used.

Following the completion of step 302 of method 300 illustrated in FIG. 3, the digital representation of the genetic variants within the first genome has been transformed into a set of discrete data structures, each of which includes a data field storing a unique alphanumeric identifier for the corresponding variant and a data field storing a unique alphanumeric identifier for the first genome. Such a set of discrete data structures can be considered to form a "base set" of data structures that subsequently can be modified or expanded so as to include the variants within other genomes. For example, method 300 further can include, for each additional genome, determining whether each genetic variant within that genome corresponds to an existing data structure (step 303). If that genetic variant is determined to correspond to an existing data structure, then the corresponding existing data structure can be modified so as to include an additional data field that includes a unique alphanumeric identifier for that additional genome (step 304). However, if that genetic variant is determined not to correspond to an existing data structure, then the digital representation of that genetic variant can be converted into an additional discrete data structure uniquely corresponding to that variant, and that includes data fields respectively storing unique alphanumeric identifiers for that variant and that genome (step 305).

In one example, step 303 can be implemented by generating a unique alphanumeric identifier for each variant within the digital representation of the variants within the additional genome, e.g., Nth genome, e.g., in a manner described above with reference to step 302 of method 300. The appropriate data fields of existing data structures then can be searched for a unique alphanumeric identifier that matches the unique alphanumeric identifier for the genetic variant in question. If such a match is found, a new data structure need not be formed so as to correspond to the genetic variant in question. Instead, the existing data structure can be modified by forming an additional data field therein, and storing within that additional data field a unique alphanumeric identifier of the Nth genome, along with any other appropriate genomic information such as described above.

In one illustrative example, it can be determined that genome N contains the same genetic variant "atc" at chromosome 1, position 20, as does genome 1 by generating the unique alphanumeric identifier for that variant within genome N, and matching that identifier to the same identifier within the existing data structure "variant ID: 1.20.cat.atc" illustrated in FIG. 2B. Based on such a match, an additional intermediate data structure containing genomic data can be generated in a manner such as described above, e.g., an intermediate data structure such as labeled "Genome Data 3" in FIG. 5C that contains the unique alphanumeric identifier of the corresponding variant, here "1.20.cat.atc," and the unique alphanumeric identifier of the corresponding genome, here "N." The intermediate data structure then can be matched with and merged with the existing data structure, e.g., data fields can be generated within the existing data structure that store the information within the data fields of the additional intermediate data structure, so as to result in a data structure such as illustrated in FIG. 2B. Such a modification process can be repeated for any other genomes that are identified as containing a variant for which a data structure has already been created. Other methods of modifying an existing data structure to include a unique alphanumeric identifier for any additional genome that includes the corresponding genetic variant suitably can be used. Alternatively, corresponding intermediate data structures such as "Variant Data 2," "Genome Data 2," and "Genome Data 3" can be merged with one another substantially concurrently so as to form a single data structure such as illustrated in FIG. 2B that includes data fields respectively storing intrinsic information about a variant and genomic information about multiple genomes, optionally with extrinsic information such as described below with reference to step 306 of method 300 illustrated in FIG. 3.

Alternatively, if a match between the additional genetic variant within the additional genome is not found, then an additional data structure corresponding to that genetic variant can be generated in a manner analogous to that described above with reference to step 302 of method 300. For example, FIG. 5D illustrates an exemplary pair of intermediate data structures, "Variant Data 4" and "Genome Data 4," that can be generated for the additional variant at chromosome 1, position 5 of genome N such as illustrated in FIG. 4A and described in the VCF file of FIG. 4B. Note that although this additional variant is of the same type (SNP), is at the same chromosome (1) and position (5), and has the same reference allele as does the corresponding variant within genome 1, note that this variant has a different alternate allele, namely "c" instead of "a." Accordingly, the unique alphanumeric identifier for this additional variant within genome N, namely "1.5.g.c" is different from that of the variant within genome 1, namely "1.5.g.a," which causes a new data structure to be generated for the additional variant. For example, the intermediate data structures within FIG. 5D can be merged with one another in a manner such as described above with reference to FIG. 5A so as to generate a data structure analogous to that illustrated in FIG. 2A and having data fields containing intrinsic, genomic, and extrinsic information about the variant, e.g., containing nucleic acid characteristics of the variant.

Following the completion of steps 303-305 of method 300 illustrated in FIG. 3, the digital representation of the genetic variants within the plurality of genomes has been transformed into a set of discrete data structures, each of which includes a data field storing a unique alphanumeric identifier for the corresponding variant and a data field storing a unique alphanumeric identifier for the first genome. Such a set of discrete data structures can be considered to form a "complete set" of data structures that together represent all or substantially all of the identified variants within the plurality of genomes. Note that because at least some of the variants within any given genome can be the same as the variants within one or more other genomes, the total number of data structures can scale sub-linearly with the total number of genomes analyzed. Indeed, as described in the above-noted article entitled "An integrated map of genetic variation from 1,092 human genomes" authored by the 1000 Genome Project, the genomes that were studied of the 1,092 individuals from 14 populations were found collectively to contain on the order of about 39 million genetic variations. Using the present systems and methods, each such genetic variation can be expressed as a corresponding data structure that identifies any genome containing that variant. As a result, the about 39 million genetic variants that the 1,000 Genome Project identified within the 1,092 studied genomes can be converted into about 39 million of the discrete data structures provided herein. It should be appreciated that modern personal computers can have sufficient computing power to perform relatively complex queries on such a number of data structures on an experimentally useful timescale—indeed on the order of milliseconds or tens of milliseconds—thus obviating the need for relatively high-powered, massively parallel computers such as described in the above-noted press release. Additionally, it should be appreciated that as new genetic variants are identified during the course of medicinal research, such variants readily can be converted into new data structures corresponding to such variants.

Moreover, the present data structures further can be modified so as to include additional data fields describing nucleic acid characteristics (step 306 of method 300 illustrated in FIG. 3). Such nucleic acid characteristics can be used during queries of the data structures so as to facilitate more rapid identification of variants that can be of interest to a researcher. For example, additional data fields can be generated within the data structures that store gene-based characteristics, such as information about one or more genes in which the corresponding genetic variant is present, or biochemical pathways in which such variants or one or more genes in which the variants are present are known to participate. Because not all genetic variants may be present in a gene or may be present in a gene that participates in a pathway, adding such information can help a user to more rapidly identify variants that are in genes or in genes that are of interest to a particular research problem. Analogously, additional data fields can be generated within the data structures that store nucleotide-based characteristics, such as information about the corresponding variants' location within the genome, or whether the variant includes a methylation, and the like. Other exemplary nucleic acid characteristics are described below with reference to Tables 2-5 and elsewhere herein.

Preferably, the present data structures corresponding to genetic variants within genomes are modified so as to include nucleic acid characteristics based on another type of data structure referred to herein as a "genome mask." Preferably, a different genome mask is generated and used for each different type of nucleic acid characteristic to be included within the present data structures corresponding to genetic variants. For example, FIG. 6 illustrates an exemplary genome mask for use in modifying the present data structures to include information about genes in which the corresponding variants can be present, which can be referred to herein using the shorthand "genemask." As described further below with reference to FIG. 9, other genome masks can be generated and used for obtaining other types of nucleic acid characteristics.

Genome masks preferably include a plurality of chromosome masks, each of which corresponds to a chromosome within the genomes being studied. For example, a human genome mask preferably includes 23 chromosome masks, while a genome mask for a different species can include a different number of chromosome masks. In the example illustrated in FIG. 6, the genemask includes chromosome masks 1 . . . X, respectively labeled using the shorthand "C1" . . . "CX," where "X" refers to the X chromosome. Preferably, each of the chromosome masks includes an array of bits, in which each of the bits corresponds to a base pair in the corresponding chromosome, and in which only bits corresponding to the positions of genes (or other extrinsic information of interest) include a flag. For example, the chromosome mask containing gene information for chromosome 1, labeled "genemaskC1" in FIG. 6, includes an array of bits that either have the value "O" or "1," in which the value "1" is a flag indicating that the chromosome contains a gene at the position corresponding to that bit. It should be understood that suitable flags other than "1" can be used. Any such genome masks preferably are stored in a non-volatile computer-readable medium such as described below with reference to FIG. 14.

FIG. 7 illustrates an exemplary method 700 for modifying a data structure corresponding to a genetic variant so as to include a nucleic acid characteristic, based on a genome mask. Method 700 includes obtaining a genome mask that includes a plurality of chromosome masks (step 701). As noted above with reference to FIG. 6, each chromosome mask can corresponding to a chromosome and can include an array of bits, each bit corresponding to a base pair position in the corresponding chromosome. Preferably, only bits corresponding to positions of known genes, or other extrinsic information, include a flag. In the illustrative example of FIG. 6, only bits that correspond to positions of known genes are flagged with a "1" while other bits are set to "0." An exemplary method of generating a genome mask is described further below with reference to FIG. 10.

Method 700 illustrated in FIG. 7 further includes determining, for each data structure corresponding to a genetic variant, whether the corresponding bit in the genome mask includes a flag (step 702). Specifically, the chromosome and position for each data structure can be obtained from that data structure's data fields respectively storing intrinsic information, e.g., chromosome 1 and position 5 for the exemplary data structure having variant ID 1.5.g.a illustrated in FIG. 2A. The bit in the genome mask that correspond to that chromosome and position can be located based on the obtained information, and subsequently can be tested to determine whether that bit includes a flag. For example, it can be readily computationally determined whether a bit includes a "0" (no flag) or a "1" (flag).

Then, if the bit corresponding to the chromosome and position of the genetic variant is determined to include a flag, a query can be submitted to a curated data source requesting the nucleic acid characteristic at the chromosome and position corresponding to that bit (step 703). In one example, the nucleic acid characteristic is a gene-based characteristic, such as a name or identifier of a gene in which the corresponding variant is present. An exemplary curated data source that can store such a nucleic acid characteristic is GENBANK, which is a publically accessible database of nucleotide sequences and their protein translations supported by the United States National Institute of Health (NIH) and is accessible online at www.ncbi.nlm.nih.gov/genbank/. Another exemplary suitable curated data source is REFSEQ, which is also supported by the NIH and is accessible online at www.ncbi.nlm.nih.gov/refseq/. Another exemplary suitable curated data source is ENSEMBL, which is supported by the European Bioinformatics Institute and the European Molecular Biology Laboratory (EMBL-EBI) and the Wellcome Trust Sanger Institute and is accessible online at uswest.ensembl.org/index.html. In one illustrative embodiment, relevant nucleic acid characteristics are extracted from such a curated data source and stored locally in a format that facilitates computationally fast queries, e.g., within a searchable database stored on a non-volatile computer readable medium such as described further below with reference to FIG. 14. For the purposes of the present invention, such locally stored nucleic acid characteristics shall be considered to be a curated data source, and can increase the speed with which data structures can be modified to include nucleic acid characteristics by obviating the need to submit queries over the Internet and await a response from a remote source, and by suitably reformatting the information in a manner that can further reduce the query time.

FIG. 8 schematically illustrates an exemplary process by which bits can be tested and a curated data source containing gene-based characteristics, e.g., GENBANK (or a reformatted, locally stored version thereof), can be queried using a genome mask such as illustrated in FIG. 6 during steps 702 and 703 of method 700 illustrated in FIG. 7. In FIG. 8, the information within the curated data source can be represented as including a plurality of arrays of characters, one array for each chromosome, in which the characters along the array represent the names or identifiers of genes at positions corresponding to those characters. For example, the information within GENBANK for chromosome 1, labeled "genbankC1," includes the letter "B" at positions 6-13, representing that a gene identified as "B" is known to be present at the corresponding positions on chromosome 1; includes the letter "J" at positions 20-22, representing that a gene identified as "J" is known to be present at the corresponding positions on chromosome 1; and dashes ("–") at the remaining positions, representing that there is no known gene stored within the GENBANK data source at those positions. It should be appreciated that such a format is only one way in which the information within a curated data source can be represented.

FIG. 8 illustrates that during step 702, within the exemplary genome mask for chromosome 1, "genemaskC1," the bit position 5, which corresponds to the variant "1.5.g.a" illustrated in FIG. 2A, can be tested to determine whether the bit includes a flag. Analogously, the bits at positions 20-22, which correspond to the variant "1.20.cat.atc" illustrated in FIG. 2B, can be tested to determine whether any of those bits include a flag. The bit at position 5 can be determined not to include a flag, e.g., because it is set to "0," while the bits at positions 20-22 can be determined to include flags, e.g., because they are set to "1." Accordingly, at step 703, the curated data source is not queried in an attempt to locate a gene corresponding to position 5, and thus no further computational power is needed with regards to this position. However, the curated data source can be queried to request the name or identifier of the gene or genes at positions 20-22, as represented by the dashed rectangle in FIG. 8. Such a query can include fields including the chromosome number (1) and the position number (20-22). The information about gene names or identifiers that is stored within the curated data source, e.g., can include reply with the alphanumeric identifier "J," corresponding to the name or identifier of the gene at that chromosome or position.

Referring again to FIG. 7, the data structure then can be "decorated" or modified so as to include a data field storing the query result, e.g., the nucleic acid characteristic (step 704). For example, continuing with the query response illustrated in FIG. 8, a data field storing the value "J" can be generated within the data structure, preferably with a field name such as "gene ID." In some embodiments, another data field storing the name of the curated data source, e.g., "GENBANK," is also generated within the data structure. Alternatively, the field name of the data field can indicate the data source, e.g., by appending the name of the data source to the field name (such as "genbankgene" or the like). In the example provided further below, the field names for genes identified using GENBANK or REFSEQ can omit such an appended data source name, but the field names for genes identified using other data sources such as ENSEMBL can include such an appended data source name; accordingly, if the field name omits a data source name, it can be inferred to mean that the data source was GENBANK or REFSEQ. It should be appreciated that method 700 illustrated in FIG. 7 can require a relatively small amount of computational power, e.g., to test whether the bits of the genome mask contain a flag such as "1," and if so to submit a query identifying the chromosome and position to a curated data source, and then to store the response to the query in a data field.

Moreover, although the example described above with reference to FIG. 8 focuses on the use of a genome mask to decorate the present data structures with information about a gene-based characteristic, such as a gene in which the corresponding variants are present, it should be appreciated that any suitable genome mask can be used to decorate the present data structures with any suitable nucleic acid characteristic. For example, FIG. 9 illustrates the array corresponding to chromosome 1 of an alternative exemplary genome mask for use in decorating a data structure with a nucleotide-based characteristic, such as information about untranslated regions of the genome from the 5' end, labeled "5'UTRmaskC1." It can be seen that the array includes flagged bits at positions 1-3 of chromosome 1, but at no other positions. The corresponding curated data source, labeled "5'UTRsourcC1" can include the value "1" at positions 1-3 of chromosome 1, representing that these positions are known to be untranslated. Accordingly, if any of the present data structures correspond to a genetic variant at positions 1-3 of chromosome 1, then the genome mask "5'UTRmaskC1" can be used to query the corresponding data source "5'UTRsourcC1" and the query result stored in a corresponding data field of that data structure. Or, for example, if new genes are identified during the course of medical research and information about those genes is stored in a curated data source, the existing genome mask can be modified or a new genome mask can be generated so as to include flags at any bits corresponding to those new genes, and that genome mask then used to decorate the present data structures with additional data fields corresponding to those new genes using a method such as illustrated in FIG. 7.

An exemplary method of generating a genome mask such as illustrated in FIG. 6 and as can be used during the method illustrated in FIG. 7 now will be described with reference to FIG. 10. Method 1000 illustrated in FIG. 10 includes defining a genome mask containing a plurality of chromosome masks, each corresponding to a respective chromosome in the genome (step 1001). Such a definition can include instantiating a data structure (a genome mask) that contains a number of subordinate data structures (chromosome masks) equal to the number of chromosomes within the genome (for humans, 23). Then, for each chromosome mask, an array of bits can be generated, in which each bit corresponds to a base pair position in the corresponding chromosome (step 1002). In one illustrative example, such an array can be instantiated by generating an array of M integers, each having a length N, where M×N is equal to or only slightly greater than L, the number of base pairs in the corresponding chromosome. For example, FIG. 11A illustrates an intermediate genome mask for genes within chromosome 1, labeled "genemaskC1-a," that includes an 1 . . . M empty integers ("Int1 . . . IntM") of exemplary length N=4. Preferably, 4×M is equal to or only slightly greater than L=249250621, the number of base pairs in chromosome 1. In some embodiments, N is a factor of 2, e.g., can be of length 2, 4, 16, 32, 64, or more. However, it should be appreciated than M and N can have any suitable values.

For each bit in the genome mask, a query can be submitted to a curated data source to determine whether the corresponding chromosome includes a nucleic acid characteristic at the position corresponding to that bit (step 1003). Optionally, such queries can be performed on a per-integer basis. If the curated data source responds that the corresponding chromosome includes the nucleic acid characteristic at the position corresponding to that bit, the bit can be flagged, e.g., can be set to "1" (step 1004). If the curated data source instead responds that the corresponding chromosome does not include the nucleic acid characteristic at the position corresponding to that bit, the bit can not be flagged, e.g., can be set to "0" (step 1005). For example, FIG. 11B illustrates submission of a query to GENBANK (which is represented analogously as in FIG. 8) for the first integer ("Int1") within genemaskC1-a, corresponding to positions 1-4. It can be seen that GENBANK does not store a gene identifier at these positions, as represented by "-," and thus responds to the query with an appropriate indication that chromosome 1 does not include a gene at the corresponding positions. Accordingly, the bits within the chromosome mask are not flagged, e.g., are set to "0," resulting in the intermediate chromosome mask "genemaskC1-b." GENBANK then can be queried for the positions corresponding to other integers within the chromosome mask, and the bits appropriately flagged, or not flagged according to the response. Such a process can be repeated for the other chromosome masks within the genome mask so as to generate a full genome mask such as illustrated in FIG. 6. Other suitable steps for generating a genome mask suitably can be used. For example, the chromosome masks need not necessarily be instantiated with empty values, but instead can be instantiated with a non-flag value such as "0" and then flagged based on the query result, or alternatively can be instantiated with a flag value "1" and then un-flagged based on the query result. The resulting genome mask can be stored in a memory, and in particular within a database within the memory.

In one illustrative example, a genome mask having chromosome masks therein can be generated during step 1001 using the following code:

```
public class GenomeMask {
    private Map<String, ChromosomeMask> fMaskMap;
    public GenomeMask( ) {
        fMaskMap = new HashMap<String, ChromosomeMask>( );
        for (String aChr : Constants.CHR_PATH_NAME) {
            ChromosomeMask aMask = new ChromosomeMask(aChr);
            fMaskMap.put(aChr, aMask);
        }
    }
    private ChromosomeMask getMask(String theChr) {
        return fMaskMap.get(theChr);
    }
```

The arrays of the chromosome masks then can be generated during step 1002 using the following code, in which M long integers of length N=64 are used in each array:

```
public class GenomeMask {
    private Map<String, ChromosomeMask> fMaskMap;
    public GenomeMask( ) {
        fMaskMap = new HashMap<String, ChromosomeMask>( );
        for (String aChr : Constants.CHR_PATH_NAME) {
            ChromosomeMask aMask = new ChromosomeMask(aChr);
            fMaskMap.put(aChr, aMask);
        }
    }
    private ChromosomeMask getMask(String theChr) {
        return fMaskMap.get(theChr);
    }
``` and in which the following constraints for the numbering and lengths of the chromosomes are applied:

```
public static final String[] CHR_PATH_NAME =
    { "1", "2", "3", "4", "5", "6", "7", "8", "9", "10",
      "11", "12 ", "13", "14", "15", "16",
      "17", "18", "19", "20", "21", "22", "23", "X", "Y",};
public static final int[] sChromosomeLength =
    { 249250621,243199373,198022430,191154276,180915260,
      171115067,159138663,146364022,141213431,135534747,
      135006516,133851895,115169878,107349540,102531392,
      90354753,81195210,78077241,59128983,63025520,
      48129895,51304566,155270560,59373566};
```

The bits within the resulting genome mask then can be flagged during steps 1003-1005 appropriately using the following exemplary code:

```
public void mark(int theStartPosition, int the EndPosition) {
    int aStartBlock = theStartPosition / sLONG_BIT_SIZE;
    int aEndBlock = theEndPosition / sLONG_BIT_SIZE;
    for (int aCurrBlock = aStartBlock; aCurrBlock <= aEndBlock;
        aCurrBlock++) {
        long aLowerMask = -1L;
        if (aCurrBlack == aStartBlock) {
            aLowerMask = -1L << (theStartPosition %
            sLONG_BIT_SIZE);
        }
        long aUpperMask = -1;
        if (aCurrBlock == aEndBlock) {
            int aMaskEnd = (theEndPosition %
            sLONG_BIT_SIZE) + 1;
            if (aMaskEnd < 64) {
                aUpperMask = (1L << aMaskEnd) - 1;
            }
        }
        getBigArray( )[aCurrBlock] = aLowerMask & aUpperMask;
    }
}
```

Referring again to FIG. 7, step 702 can be implemented using the following exemplary code:

```
public boolean test(int thePosition) {
    int pos = thePosition / sLONG_BIT_SIZE;
    int bit = thePosition % sLONG_BIT_SIZE;
    long l = 1L << bit;
    long v = getBigArray( )[pos] & 1;
    return (v != 0);
}
```

Note that because genome masks are simply genome-wide arrays of bits that represent genomic position indicators, they can be combined using bitwise operations to quickly perform the following operations:

Intersect: get minimum coverage mask using AND logic,
Union: get maximum coverage mask using OR logic,
Symmetrical Differentiate: get values unique to two masks, or,
Subtract: get values unique in one mask from another.

Accordingly, combined masks can be used to define more complex relationships between different types of nucleic acid characteristics. The above bitwise operations can be implemented using the following exemplary code:

```
public void intersect(ChromosomeMask theOther) {
    for (int i=0; i < getBigArray( ).length; i++) {
        getBigArray( )[i] = getBigArray( )[i] & theOther.getBigArray( )[i];
    }
}
public void union(ChromosomeMask theOther) {
    for (int i=0; i < getBigArray( ).length; i++) {
        getBigArray( )[i] = getBigArray( )[i] | theOther.getBigArray( )[i];
    }
}
public void symmCriticalDiff(ChromosomeMask theOther) {
    for (int i=0; i < getBigArray( ).length; i++) {
        getBigArray( )[i] = getBigArray( )[i] ^ theOther.getBigArray( )[i];
    }
}
public void subtract(ChromosomeMask theOther) {
    for (int i=0; i < getBigArray( ).length; i++) {
        getBigArray( )[i] = getBigArray( )[i] & -theOther.getBigArray( )[i];
    }
}
```

Additionally, as noted above, the step of modifying data structures can be performed at any suitable point during the execution of method 300 illustrated in FIG. 3. For example, modifying intermediate data structures such as illustrated in FIGS. 5A-5D can enhance the speed with which the modifications can be performed. In particular, because the intermediate variant and genome data structures both contain the same hash or concatenation that uniquely identifies the variant, the modification and merge steps can be performed in a multi-process manner so as to speed up processing time. For example, each process can be restricted to a subset of the data based on the hash or concatenation, permitting the modification and merge steps to be performed in parallel. By comparison, without using such a hash or concatenation to segment the data structures or intermediate data structures being processed, there can be a high disk input/output (I/O) contention between competing processes.

Using methods such as illustrated in FIGS. 7 and 10, it should be appreciated that the present data structures suitably can be decorated so as to include any desired nucleic acid characteristic with a relatively low amount of computational power required to do so. For example, such a nucleic acid characteristic can include gene-based characteristics such as a name or identifier of a gene in which the genetic variant is present, a biochemical pathway in which the genetic variant or a gene in which it is present is known to participate, an indication of whether the genetic variant is listed in a particular curated data source, a cancer type in which the genetic variant or a gene in which it is present is involved, a disease phenotype in which the genetic variant or a gene in which it is present is involved (e.g., correlated with disease presence), a gene that is known to be expressed that contains the genetic variant, a dbSNP associated with the genetic variant, or a transcription factor that is at least partially encoded by the genetic variant. Or, for example, such a nucleic acid characteristic can include a nucleotide-based characteristic such as an indication of methylation, or genomic location information such as an indication of whether the genetic variant is located in an exon, an intron, a regulatory region, a splice site, a flanking region, a promoter region, or a region that codes for non-coding RNA, or a variant type of the genetic variant, e.g., whether the variant is a missense, nonsense, synonymous, insertion, deletion, or structural variation. Or, for example, the nucleic acid characteristic can include a score-based characteristic such as an allele frequency associated with the genetic variant, a SIFT score associated with the genetic variant, a PolyPhen-2 score associated with the genetic variant, a PolyPhen score associated with the genetic variant, or a PFAM associated with the genetic variant. Or, for example, the nucleic acid characteristic can include a genome-based characteristic such as a zygosity of the genome in which the genetic variant is present, a fractional allele frequency for the corresponding genetic variant in the genome in which the corresponding genetic variant is present, a phenotype of the genome, a phenotype of the genome in which the genetic variant is present, a demographic of the genome in which the genetic variant is present, and a clinical indication of the genome in which the genetic variant is present. Or, for example, the nucleic acid characteristic can include a sample-specific characteristic such as a read quality of the genome in which the genetic variant is present, or a read depth of the genome in which the genetic variant is present. Some specific exemplary sources and uses of such nucleic acid characteristics in query terms are described further below with reference to steps 308-310 of method 300 illustrated in FIG. 3 and in Tables 2-5. Preferably, any such nucleic acid characteristic is stored in alphanumeric form within a respective data field, preferably with a field name indicating the type of nucleic acid characteristic.

FIG. 12 illustrates an exemplary data structure for variant "1.5.g.a" that includes data fields, with corresponding field names, for multiple types of nucleic acid characteristics, e.g., extrinsic information. It should be appreciated that not all of such data fields or nucleic acid characteristics are required, and also that data fields other than those illustrated in FIG. 12 can be included. In particular, as noted above with reference to FIGS. 2A-2B, some data fields of the present data structures can store information about the genomes that include the corresponding genetic variant. Some of such genome-based or sample-specific characteristics can be obtained from the digital representation of the variants within that genome, e.g., from a VCF file or other suitably formatted file for that genome, such as a zygosity of the genome for that genetic variant, a fractional allele frequency for the corresponding genetic variant in the genome in which the corresponding genetic variant is present, a read quality of the genome for that genetic variant, or a read depth of the genome for that genetic variant. Other nucleic acid characteristics that can be stored in data fields of the present data structures includes a demographic of the genome or a phenotype of the genome or a clinical indication of the genome, or a pointer to such phenotype or clinical indication, which can be stored separately.

Referring again to method 300 illustrated in FIG. 3, after the present data structures are generated and modified, they can be stored in a database in a memory or non-transitory computer-readable medium (step 307). As should be appreciated, a variety of different databases and computer-readable media suitably can be used to store the present data structures. For example, as noted above, Lucene databases can be particularly well suited for storing the present data structures, although databases based on SQL and other programming languages alternatively can be used. Additionally, note that data structures are stored in the database, they can be retrieved from the computer-readable medium, modified, and then stored again.

Preferably, the data structures are stored in the database computer-readable medium in such a manner that they can be queried relatively quickly. In particular, the database can receive a query term that includes unique alphanumeric identifiers for one, two, or more genomes, and an operation to be performed (step 308). The query term can use a syntax appropriate to the particular database in which the data structures are stored, and the operation can include, for example, a union, differentiate, intersect, or symmetric differentiate operation such as described above with reference to FIGS. 1B-1E. The database then searches the data fields of data structures stored within the database for any data fields that match the query term and satisfy the operation (step 309), and generates an output that uniquely identifies a genetic variant and any genomes containing that variant that were identified during the search (step 310). Such an output can include a list (or other representation) of the variants corresponding to those data structures. For example, the database can output the labels for those data structures, can output the start and end positions, reference allele, variant allele, or variant type corresponding to those data structures, or can output a graphical representation of the position(s) of the variants within the genomes. In one illustrative example, the output includes a list of variants that are shared between at least two of the genomes identified in the query term, or a list of variants that are unique to at least one of the genomes identified in the query term. Preferably, the database provides such output on a display screen that is either colocated with the database or is remote from the database such as described below with reference to FIG. 14, but the output alternatively can be stored in a computer-readable medium. Exemplary user interfaces for submitting query terms and for displaying query results are described in greater detail below with reference to FIGS. 15A-15L.

Exemplary syntax terms for use with a Lucene database are provided further above with reference to the exemplary operations illustrated in FIGS. 2A-2B. However, it should be appreciated that the present systems, methods, and data structures are compatible with more complex queries, e.g., queries that identify one or more, two or more, three or more, four or more, five or more, six or more, seven or more, eight or more, nine or more, or even ten or more genomes, and can provide outputs responsive to such queries on experimentally practical time scales, e.g., one second or less, or 100 milliseconds or less, or 10 milliseconds or less, or even 1 millisecond or less. In particular, it has been observed that the more complex the query, the more rapidly a result can be obtained, because fewer data records satisfy the query terms. FIGS. 13A-13R illustrates set representations of exemplary query terms that can be received in step 308 of method 300, as well as the results of such queries (the shaded areas within those set representations), and Table 1 lists the genomes, query terms, and results and comments for the set representations illustrated in such figures. Note that in the exemplary queries in Table 1, the term "g" means the field name for the data fields containing unique identifiers for genomes. Also, Table 1 refers to "tumor" or "cancer," but it will be evident that similar techniques can be applied to any phenotype of interest that differs among individuals.

TABLE 1

Exemplary Queries

| FIG. | Genomes | Query Term | Result/Comments |
|------|---------|------------|-----------------|
| 13A | T1: Indiv. 1, Tumor<br>N1: Indiv. 1, Normal | +(+g:T1 −g:N1) | Outputs tumor specific variants, e.g., for use in identifying "driver" or "passenger" mutations in tumor, and key genes involved in tumor related processes |
| 13B | T1: Indiv. 1, Tumor<br>N1: Indiv. 1, Normal<br>N2: Indiv. 2, Normal | +(+g:T1 −(g:N1 g:N2) | Outputs only tumor specific variants. |
| 13C | T1: Indiv. 1, Tumor<br>N1: Indiv. 1, Normal<br>N2: Indiv. 2, Normal | +(+g:T1 − (+g:N1 +g:N2) | Compares tumor variants against normal variants derived from related but disease-free individuals |
| 13D | T1: Indiv. 1, Tumor 1<br>T2: Indiv. 1, Tumor 2<br>N1: Indiv. 1, Normal | +(+(g:T1 g:T2) −g:N1) | Outputs variants specific to tumor genomes. |
| 13E | T1: Indiv. 1, Tumor 1<br>T2: Indiv. 1, Tumor 2<br>N1: Indiv. 1, Normal | +(+(+g:T1 +g:T2) −g:N1) | Outputs variants shared only by tumor genomes. |

TABLE 1-continued

Exemplary Queries

| FIG. | Genomes | Query Term | Result/Comments |
|---|---|---|---|
| 13F | T1: Indiv. 1, Tumor<br>N1: Indiv. 1, Normal<br>T2: Indiv. 2, Tumor<br>N2: Indiv. 2, Normal | +((+g:T1 −g:N1)<br>(+g:T2 −g:N2)) | Outputs range of mutations present in tumor genomes only. |
| 13G | T1: Indiv. 1, Tumor<br>N1: Indiv. 1, Normal<br>T2: Indiv. 2, Tumor<br>N2: Indiv. 2, Normal | +(+(g:T1 g:T2)<br>−(g:N2 g:N2)) | Outputs tumor specific variants. |
| 13H | T1: Indiv. 1, Tumor<br>N1: Indiv. 1, Normal<br>T2: Indiv. 2, Tumor<br>N2: Indiv. 2, Normal | +(+(+g:T1 −g:N1)<br>+(+g:T2 −g:N2)) | Outputs variants shared by tumor genomes. The list can contain candidate cancer related genes important to tumor survival. |
| 13I | T1: Indiv. 1, Tumor 1<br>T2: Indiv. 1, Tumor 2 | +(+g:T2 −g:T1) | Identify variants specific to second tumor as compared to first tumor for same individual.<br>Recurrent tumors for the same individual can carry mutations that confer therapeutic resistance that have evolved in time. In such cases, it is important to identify new mutations acquired by recurrent tumors. |
| 13J | T1: Indiv. 1, Tumor 1<br>T2: Indiv. 1, Tumor 2<br>T3: Indiv. 1, Tumor 3 | +(+g:T3 +g:T2<br>+g:T1) | Serial differentiation outputs variants shared by all three of an individual's tumors. |
| 13K | T1: Indiv. 1, Tumor 1<br>T2: Indiv. 1, Tumor 2<br>T3: Indiv. 1, Tumor 3 | +(+g:T3 −(g:T2<br>g:T1)) | Outputs variants unique to third recurrent tumor relative to first two tumors. |
| 13L | C: Child<br>M: Mother<br>F: Father | +(+g:C −(g:M<br>g:F)) | Differentiates child-specific variants from union of parental variants, e.g., to identify dominant de novo pathogenic mutations in child genome. These de novo variants can be further queried to identify deleterious/pathogenic variants. |
| 13M | C: Child<br>M: Mother<br>F: Father | +((+g:F +g:M)<br>+g:C) | Outputs variants common to mother, father, and child.<br>To identify homozygous variants in child at loci where both parents carry heterozygous variants, define query term to identify homozygous variants, optionally followed by defining query term to identify functionally deleterious variants. |
| 13N | C: Child<br>M: Mother<br>F: Father | +(+(g:F g:M) +g:C) | Outputs variants in mother and father inherited by the child.<br>The list of variants in the child can be queried for genes that carry more than one mutation as a result of the combined inheritance from each parent. The resulting list of genes in the child with co-occurring variants can be further queried for deleterious effects. |
| 13O | A1: Responder 1<br>A2: Responder 2<br>B1: Nonresponder 1<br>B2: Nonresponder 2<br>B3: Nonresponder 3 | +(+(g:A1 g:A2)<br>−(g:B1 g:B2<br>g:B3)) | Differentiate union of responders from union of nonresponders.<br>For identifying drug response phenotype in clinical cohorts from clinical trials. Identify differences between a group of responders and non-responders using percentage-based thresholds. |
| 13P | A1: Responder 1<br>A2: Responder 2<br>B1: Nonresponder 1<br>B2: Nonresponder 2<br>B3: Nonresponder 3 | +(+(+g:A1<br>+g:A2) −(+g:B1<br>+g:B2 +g:B3)) | Differentiate intersection of responders from intersection of nonresponders.<br>For identifying drug response phenotype in clinical cohorts from clinical trials. Identify differences between a group of responders and non-responders using percentage-based thresholds. |
| 13O | A1: Responder 1<br>A2: Responder 2<br>B1: Nonresponder 1<br>B2: Nonresponder 2<br>B3: Nonresponder 3 | +(+(+g:A1<br>+g:A2) −(g:B1<br>g:B2 g:B3)) | Differentiate intersection of responders from union of nonresponders.<br>For identifying drug response phenotype in clinical cohorts from clinical trials. Identify differences between a group of responders and non-responders using percentage-based thresholds. |
| 13R | B1: Indiv. 1, Cancer 1<br>B2: Indiv. 2, Cancer 1<br>B3: Indiv. 3, Cancer 1<br>B4: Indiv. 4, Cancer 1<br>A: Indiv. 5, Healthy | +g:A +(g:B1<br>g:B2 g:B3 g:B4)) | Outputs variants shared between healthy individual (A) and comparison set (B1, B2, B3, B4) having a particular type of cancer (1). Alternatively, comparison set can have a particular phenotype. |

Additionally, as noted above with reference to FIGS. 6-12, the present data structures preferably include data fields respectively storing nucleic acid characteristics such as the names or other identifiers of any genes in which the corresponding variants are present, an indication of whether the variant is in an exon or an intron, or an indication of the variant type. The nucleic acid characteristics can be information such as the zygosity of the genome for the variant corresponding to that data structure, a fractional allele frequency for the corresponding genetic variant in the genome in which the corresponding genetic variant is present, the phenotype of the patient having that genome (e.g., disease diagnosis, responsiveness to a particular treatment, and the like), or a clinical indication of the patient. Such data fields can be included as part of the query term received in step 308 using an analogous syntax as described above. For example, the following query can be used to search within a given genome (1) for any variants that have a non-null ("−") value for gene name, e.g., to perform a "union" operation on the genome having the unique alphanumeric identifier "1" and containing any value in the data field named "gene":

+(g:1)−gene:− where "gene" is the field name for the data field containing the names of genes. Or, for example, the following query can be used to search within a given genome (1) for any variants that fall within the gene named "FHIT," e.g., to perform a "union" operation on the genome having the unique alphanumeric identifier "1" and containing the value "FHIT" in the data field named "gene:"

+(g: 1)+(gene:FHIT).

Or, for example, the following query can be used to retrieve all variants that fall in one of a set or list of genes of particular interest to the researcher, e.g., FHIT, HRAS, RAB5EP, and FLJ23752, e.g., to perform a "union" operation on the genome having the unique alphanumeric identifier "1" and containing the values "FHIT," "HRAS," "RAB5EP," or "FL27352" in the data field named "gene:"

+(g: 1)+(gene:FHIT gene:HRAS gene:RAB5EP gene:FL27352).

Other data fields similarly can be added to the query term. For example, to retrieve only variants for genome (1) that are on chromosome 9, where "c" is the field name for the chromosome data field, a query can use the following syntax, e.g., to perform a "union" operation on the genome having the unique alphanumeric identifier "1" and containing the value "9" in the data field named "c":

+(g:1)+(c:9).

Or, for example, to obtain an output only of variants that include data fields listing missense mutations within a field having the field name "exon", the following query term can be used, e.g., to perform a "union" operation on the genome having the unique alphanumeric identifier "1" and containing the value "missense" in the data field named "exon:"

+(g: 1)+(exon:missense).

Additional query terms may be added to the immediately preceding term so as to retrieve only variants that are homozygous for genome 1 by using the following query term e.g., to perform a "union" operation on the genome having the unique alphanumeric identifier "1" and containing the value "missense" in the data field named "exon" and a zygosity of "1|1" in the data field named "zyg_1":

+(g: 1)+(exon:missense)+zyg_1:11, where zyg_1 is the field name for the zygosity of genome 1 for the corresponding variant. Or, for example, to retrieve only variants that are found in the 5' untranslated (UTR) region for genome 1, the following query term can be used, e.g., to perform a "union" operation on the genome having the unique alphanumeric identifier "1" and containing the value "UTR5*" in the data field named "UTR:"

+(g: 1)+(UTR:UTR5*), where UTR is the field name for data field that contains an alphanumeric indication of the region in which the variant is located, e.g., 5' UTR, 3' UTR, near 5' UTR, or near 3' UTR.

Other query terms that identify other nucleic acid characteristics can be envisioned. Tables 2-5 list exemplary types of nucleic acid characteristics that can be included in data fields of the present data structures, the uses of such information, and the exemplary workflow by which such information can be used while querying a database storing such data structures. As noted above, the nucleic acid characteristic stored within the present data structures can be, for example, a gene-based characteristic, a nucleotide-based characteristic, a score-based characteristic, a genome-based characteristic, and/or a sample-specific characteristic, or any combination thereof. Indeed, any given one of the present data structures may store any suitable number of different nucleic acid characteristics, e.g., may store at least one nucleic acid characteristic in different data fields. For example, any given one of the present data structures may store at least two nucleic acid characteristics in different data fields. Or, for example, any given one of the present data structures may store at least three nucleic acid characteristics in different data fields. Or, for example, any given one of the present data structures may store at least four nucleic acid characteristics in different data fields. Or, for example, any given one of the present data structures may store at least five nucleic acid characteristics in different data fields. Or, for example, any given one of the present data structures may store at least ten nucleic acid characteristics in different data fields. Or, for example, any given one of the present data structures may store at least twenty nucleic acid characteristics in different data fields. Or, for example, any given one of the present data structures may store at least thirty nucleic acid characteristics in different data fields. Or, for example, any given one of the present data structures may store at least forty nucleic acid characteristics in different data fields. Or, for example, any given one of the present data structures may store at least fifty nucleic acid characteristics in different data fields, or even more.

Furthermore, the query term may include an identification of any suitable number of nucleic acid characteristics, based on which the data base may be searched for data structures that not only have data fields storing unique alphanumeric identifiers that match the genome identified in the query term and that satisfy the operation, but that also store the identified nucleic acid characteristic or characteristics. For example, the query term may include an identification of at least one nucleic acid characteristic. Or, for example, the query term may include an identification of at least two nucleic acid characteristics. Or, for example, the query term may include an identification of at least three nucleic acid characteristics. Or, for example, the query term may include an identification of at least four nucleic acid characteristics. Or, for example, the query term may include an identification of at least five nucleic acid characteristics. Or, for example, the query term may include an identification of at least ten nucleic acid characteristics. Or, for example, the query term may include an identification of at least twenty nucleic acid characteristics. Or, for example, the query term may include an identification of at least thirty nucleic acid characteristics. Or, for example, the query term may include an identification of at least forty nucleic acid characteristics. Or, for example, the query term may include an identification of at least fifty nucleic acid characteristics, or even more.

By "gene-based characteristic" it is meant a characteristic of the genetic variant that relates to a gene in which the variant is present or that it is near. For example, if the genetic variant is present in a gene, then the data structure for that variant can include a name or identifier of that gene. However, the present data structures can store information about more complex relationships between genetic variants and genes. For example, the gene-based characteristic can include an identification of a biochemical pathway in which the genetic variant or a gene in which it is present is known to participate, or an indication of whether the genetic variant is listed in a particular curated data source (e.g., a data source that lists genetic variants that have been associated with a particular disease), or a cancer type in which the genetic variant or a gene in which it is present is involved, or a disease phenotype in which the genetic variant or a gene in which it is present is involved, or a gene that is known to be expressed that contains the genetic variant, or a dbSNP associated with the genetic variant.

By "nucleotide-based characteristic" it is meant a characteristic that relates to a location or characteristic of a nucleotide of the genetic variant. For example, the nucleotide can be methylated, or can be present in a genomic location such as an exon, an intron, a regulatory region, a flanking region, a promoter region, or a region that codes for non-coding RNA. Or, for example, the nucleotide can be associated with a particular type of genetic variation, such as a missense, non-sense, synonymous, insertion, deletion, or structural variation.

By "score-based characteristic" it is meant a characteristic that relates to an analysis of the genetic variant that produces a score or other metric of the variant. For example, analyses such as an allele frequency, SIFT, PolyPhen-2, PolyPhen, or PFAM can be performed for the genetic variant, and the score or other metric resulting from that analysis can be stored within a data field of the present data structures.

By "genome-based characteristic," it is meant a characteristic that relates to a genome that contains the genetic variant, or an individual having that genome. For example, a genome that (or an individual who) contains the genetic variant can have a zygosity, e.g., 0|1 or 1|1; a phenotype, e.g., a particular disease; a demographic, e.g., American, African, European, or Asian; a fractional allele frequency of a variant; or a clinical indication, e.g., a positive response to a treatment for a particular disease.

By "sample-specific characteristic" it is meant a characteristic that relates to the specific sample used to generate the digital representation of variants within a genome. For example, the read depth or read quality of the sample can be stored within a data field of the present data structures.

TABLE 2

Gene-Based Characteristics

| Gene-Based Characteristic | Uses | Workflow |
| --- | --- | --- |
| Pathways | Pathways is a powerful way to query for variants to identify mutations in a specific biological pathway. For example, the cell death pathway is important for destroying cells with malignant potential. Knowledge of variants in genes involved in such pathways will help to interpret Next Generation Sequencing (NGS) data. | Select variants by type, location, and effect to output potentially pathogenic mutations. Then add query term corresponding to their role in biological pathways by choosing specific pathways, in order to identify cancer related cellular processes that can be impacted by the mutation. |
| COSMIC | The Catalog of Somatic Mutations in Cancer (COSMIC) is a database of genes with recurrent mutations in different cancers. It can be used to query for COSMIC variants present in the analysis dataset. | Query variants to identify by type, site, and/or damaging score. Then submit additional COSMIC query and choose cancer type relevant to study set. The output will yield all recurrent mutations in the analysis data. |
| OMIM | Online Mendelian Inheritance in Man (OMIM) is a database of variants that are associated with a specific disease phenotype. It is a rich database for querying an uncharacterized genome to identify known pathogenic variants. | Query variants to identify by type, site, and/or damaging score. Then submit additional OMIM query and choose a disease type relevant to study set. The output will yield all OMIM documented mutations in the analysis data. |
| Custom Gene List | A researcher or clinician can be interested in only a few genes so as to focus on mutations in these genes in the investigational disease or patient. The user defined gene list can be used to query for variants present in specific genes in the patient genome. | Upload desired gene list. Then add gene list query and select the list/panel of interest. Now add query terms corresponding to variant type, site, and damaging potential. |
| Transcription Factor Analysis | Transcription factors (TFs) are regulatory proteins that bind to specific regions of the gene sequence and initiate gene transcription. Knowledge of disruptive variants in TFs, e.g., TFs that are at least partially encoded by the genetic variant, and their targets and pathways would greatly assist in interpreting NGS variant data. | Submit query to narrow variant list to TF database. Now add query terms corresponding to variant type, site, and damaging potential. Additional pathways query term can be added to focus on pathways that can be impacted by a pathogenic variant carrying TF. |

TABLE 2-continued

Gene-Based Characteristics

| Gene-Based Characteristic | Uses | Workflow |
|---|---|---|
| TCGA | The Cancer Genome Atlas (TCGA) is a repository of diverse genomic data types and alterations in them associated with genomes with a specific cancer type and clinical phenotype. | Submit query to narrow variant list by variant type, site, and damaging potential. Add query term for TCGA and choose the desired cancer type and clinical phenotype combination. Additional pathways query term can be added to focus on desired pathways that can be impacted. The resulting variant list will contain TCGA documented deleterious mutations in a cancer type and subtype. |
| Gene Ontology | Gene Ontology (GO) is a high quality curated database of all genes and their role in cellular processes, functions, and subcellular locations. Knowledge of GO of genes in it is a logical way of querying for biologically relevant mutations. | Apply any desired query terms. Then add GO query term and choose relevant function/process to see variants in genes that might impact these functions and processes. |
| Gene Expression | To obtain the variant status of genes present in an expression study set, e.g., to identify a gene that contains the genetic variant and that is known to be expressed under a set of study conditions. | Query a list of genomic variants by selecting "gene expression" query term and specifying a desired expression study. |
| dbSNP | To include or exclude variants in the Single Nucleotide Polymorphism Database (dbSNP) based on a specific research question. | Apply dbSNP query term to a list of genomic variants by selecting either only those variants within dbSNP or not within dbSNP. Selecting "off" criteria outputs variants irrespective of dbSNP presence. |

TABLE 3

Nucleotide-Based Characteristics

| Nucleotide-Based characteristic | Uses | Workflow |
|---|---|---|
| CDS | Identify genetic variants by their location in a coding DNA sequence (CDS) in a genome. Knowledge of variants by location will allow for predicting the impact of the alteration on tumor behavior or drug response. | Query for variants in coding DNA sequences (CDS). Variants in CDS are more likely to affect protein structure and consequently its function. |
| Introns | Identify genetic variants by their location in an intron in a genome. Knowledge of variants by location will allow for predicting the impact of the alteration on tumor behavior or drug response. | Query for variants in introns. Mutations in introns can affect splicing and thereby the expressed protein. |
| Regulatory Regions | Identify genetic variants by their location in a regulatory region in a genome. Knowledge of variants by location will allow for predicting the impact of the alteration on tumor behavior or drug response. | Query for variants in a regulatory region. For example, variants in 5', 3', near 5' end, and near 3' end can affect binding of regulatory elements, and methylation patterns. |
| Splicing | Identify genetic variants by their location in a splice site in a genome. Knowledge of variants by location will allow for predicting the impact of the alteration on tumor behavior or drug response. | Query for variants in splice sites. Variants in splice sites can disrupt normal splicing and give rise to defective proteins. |
| Non-Coding RNA | Identify genetic variants by their location in sections of DNA that code for non-coding RNA. Knowledge of variants by location will allow for predicting the impact of the alteration on tumor behavior or drug response. | Query for variants in DNA that code for non-coding RNA. Mutations in one or more of the RNA family (e.g., LiNC RNA, tRNA, miRNA) can be identified using such a query term. |

TABLE 3-continued

Nucleotide-Based Characteristics

| Nucleotide-Based characteristic | Uses | Workflow |
| --- | --- | --- |
| Flanking regions | Identify genetic variants by their location in sections of DNA that are within a defined number of base pairs from a gene. For example, the following flanking regions can be defined:<br>3' Flank: 10,000 base pairs before the 3' end of a gene.<br>5' Flank: 10,000 base pairs before the 5' end of a gene.<br>3' Near Flank: 1,000 base pairs before the 3' end of a gene.<br>5' Near Flank: 1,000 base pairs before the 5' end of a gene. | Query for variants in DNA that are within a defined number of base pairs from a gene. |
| Promoter Regions | Identify genetic variants by their location in sections of DNA that initiate transcription of a gene. For example, the following promoter region can be defined:<br>Promoter: 500: 1,000 base pairs to the 5' end of the gene and 500 base pairs 3' to the same end. | Query for variants in DNA that are within sections of DNA that initiate transcription of a gene. |

TABLE 4

Additional Nucleotide-Based Characteristics

| Nucleotide-based Characteristic | Uses | Workflow |
| --- | --- | --- |
| Missense | Different mutation types, such as missense, have different impacts on protein structure and function. Knowledge of variant type is important to understanding consequences of the mutations, as well as identifying/discovering drug targets. | Submitting query terms identifying variant types in the context of specific genomic locations, genes, or chromosomes can help address specific research questions. Add CDS/exon query term and add missense query term. Querying for missense mutations will output variants that cause changes in amino acid, which can lead to pathogenicity. Apply query terms to whole genome or to specific chromosome. |
| Nonsense | Different mutation types, such as nonsense, have different impacts on protein structure and function. Knowledge of variant type is important to understanding consequences of the mutations, as well as identifying/discovering drug targets. | Submitting query terms identifying variant types in the context of specific genomic locations, genes, or chromosomes can help address specific research questions. Add CDS/exon query term and apply nonsense query term. Nonsense query terms identify premature stop codons leading to truncated, incomplete, nonfunctional proteins. Apply query terms to whole genome or to specific chromosome. |
| Synonymous | Different mutation types, such as synonymous, have different impacts on protein structure and function. Knowledge of variant type is important to understanding consequences of the mutations, as well as identifying/discovering drug targets. | Submitting query terms identifying variant types in the context of specific genomic locations, genes, or chromosomes can help address specific research questions. Add CDS/exon query term and add synonymous query term. These mutations do not cause change of amino acids but can affect stability at transcript level. Apply query terms to whole genome or to specific chromosome. |
| Insertions, Deletions, or Structural Variations | Different mutation types, such as insertions, deletions, or structural variations, have different impacts on protein structure and function. Knowledge of variant type is important to understanding consequences of the mutations, as well | Submitting query terms identifying variant types in the context of specific genomic locations, genes, or chromosomes can help address specific research questions. Add query terms identifying one or more of insertion, deletion, or structural |

TABLE 4-continued

Additional Nucleotide-Based Characteristics

| Nucleotide-based Characteristic | Uses | Workflow |
|---|---|---|
| | as identifying/discovering drug targets. | variations and apply to all variants. These mutations can occur at any location and can be combined with other query terms such as specific genome location(s). Structural variations can involve larger chunks of the genome. Apply query terms to whole genome or to specific chromosome. |

TABLE 5

Score-Based Characteristics

| Score-based Characteristic | Uses | Workflow |
|---|---|---|
| Allele Frequency (AF) | To obtain an overview of the minor allele frequencies in the general population as calculated from the 1000 Genomes Project. This information would help to identify variants that can impact drug response in a select population. | From a list of variants, obtained using query terms that either do or do not identify variant type, location, pathway, or other biological filter, add additional query term identifying AF to query by allele frequency in one or more races. |
| Quantitative and Qualitative Prediction | To predict impact of mutations within coding sequences. Not all mutations in the coding region can alter protein structure and function drastically leading to pathogenic variants. The application of a prediction algorithm aids in removing non-deleterious variants from a long list of variants identified in the genome. | Select mutations based on score output or qualitative predictions by algorithms. SIFT and PolyPhen -2 algorithms provide numerical scores, and PolyPhen provides a flat qualitative prediction. For further details on SIFT scores, see Ng et al., "SIFT: predicting amino acid changes that affect protein function," Nucleic Acids Research, vol. 31 (13): 3812-3814. |
| PFAM | Identify variants that fall within functional domains of a protein. PFAM is a database of protein families that includes their annotations and multiple sequence alignments. | From a list of variants, obtained using query terms that either do or do not identify variant type, location, pathway, or other biological filter, add PFAM query term and select one or more functional domains of interest. The resulting list of variants will include only those variants that fall within important/desired protein domains. |

Additionally, it should be appreciated that different sources of information about genetic variants can be used. For example, the digital representation of an individual's genetic variants can be based on so-called "next-generation sequencing" (NGS) methods. Table 6 lists exemplary genetic information that can be obtained using NGS methods such as known in the art. The nucleic acid characteristics stored within the present data structures can include information obtained using NGS methods (such as whole genome sequencing, whole exome sequencing, or transcriptome shotgun sequencing). For example, the nucleic acid characteristics can include a nucleotide-based characteristic such as an indication of methylation, which can be obtained using NGS methods.

TABLE 6

NGS-Based Information

| Information | Uses | Workflow |
|---|---|---|
| Whole Genome Sequencing Data | Diverse types of genomic alterations at the cellular level can be identified by studying diverse genomic profiles generated by NGS, such as whole genome sequencing (WGS) data. | Enables identification of genome wide alterations/variations of different types described herein. |

TABLE 6-continued

NGS-Based Information

| Information | Uses | Workflow |
| --- | --- | --- |
| Whole Exome Sequencing Data | Diverse types of genomic alterations at the cellular level can be identified by studying diverse genomic profiles generated by NGS, such as whole exome sequencing (WES) data. | Enables identification of variations/alterations present within coding region of the genome. |
| RNAseq | Diverse types of genomic alterations at the cellular level can be identified by studying diverse genomic profiles generated by NGS, such as RNAseq, also referred to as whole transcriptome shotgun sequencing. | Analyze RNAseq data to identify post-transcriptional alterations including splice variants, novel transcripts, expression levels of the gene, and alteration. |
| Methylation | Diverse types of genomic alterations at the cellular level can be identified by studying diverse genomic profiles generated by NGS, such as methylation. | Identify and analyze differentially methylated regions in the genome or in targeted regions, to provide information on the expression status of genes. |
| Copy Number Variation | Diverse types of genomic alterations at the cellular level can be identified by studying diverse genomic profiles generated by NGS, such as copy number variation (CNV). | Identify and analyze CNVs involving large regions of the genome. This includes duplications or deletions which can be determined at higher resolutions using NGS data as compared to comparative genomic hybridization (CGH) data. |
| Loss of Heterozygosity | Diverse types of genomic alterations at the cellular level can be identified by studying diverse genomic profiles generated by NGS, such as loss of heterozygosity (LOH). | Loss of one of the alleles at a locus can lead to loss or mutation of the other allele which can be detected from NGS data. |

Based on the foregoing, it should be appreciated that the present systems, methods, and data structures can facilitate a wide variety of genomic analyses on time frames that can significantly accelerate the pace of such analyses. For example:

Users can examine the variants in one genome, in a group of genomes, or in "computed" genomes, e.g., real-time subtraction of a germ-line genome from a cancer genome.

Users can view variants data at the level of base pairs, genes, or pathways, both in tables and in maps.

Users can "filter" variants dynamically, that is, to add to the query term one or more identifications of corresponding nucleic acid characteristics, to allow focus on features of biological interest. For example, they can submit a query term that excludes all variants present in dbSNP, or that requires only variants that alter protein function, or that requires only variants present in genes found in the COSMIC cancer gene database, or that requires only variants present in genes found in a subset of COSMIC associated with a particular cancer type, or that requires only variants present in genes found in a subset of the Gene Ontology database, or that requires only variants present in a subset of pathways from the NCI/Nature pathway set, or any combination of these. Each additional query operation to add such query terms can take a second or less, e.g., 100 milliseconds or less, or even 10 milliseconds or less.

Variants also can be queried to identify those involved in gene expression (e.g., only to show genes present in a tissue), e.g., by uploading an appropriate data file; or filtered by any uploaded gene set, e.g., genes hypothesized in a new paper to act as drivers for a particular cancer.

Gene sets, created by any of the above-mentioned methods, can be expanded using protein-protein interaction information. For example, variants can be queried using an uploaded breast tumor gene expression set, the query term may identify "cell death" pathways, and the query term then expanded to all the genes that have protein products that interact with the products of the resulting set.

Users also can examine structural variants, and query those variants based on the properties of the genes involved, e.g., to show all tandem repeats involving a COSMIC gene.

The results of such genomic analyses and any additional clinical data can serve as input to a rules engine, followed by a report generator. The report can include findings, notes and recommendations and can be edited. Both the rule set and the report template can be tailored to the researcher's preferences. An exemplary format for such a report is described in greater detail below with reference to FIG. 15K.

It should be appreciated that the present systems, methods, and data structures can facilitate a wide variety of genomic analyses for use in research or clinical contexts. For example, in the research context, a researcher can wish to learn whether a disease is associated with a novel genetic variation that can be detected by analyzing genetic variants. Using graphical user interfaces such as described in greater detail below with reference to FIGS. 15A-15L, the researcher can select a plurality of genomes for investigation and query terms to select only variants for which the genomes are heterozygous, and that are not listed in the dbSNP database. The researcher can further narrow the resulting list of variants by selecting a query term to select only variants that are known to be within a gene. The researcher then can perform further experiments to determine whether the genes for the resulting list of variants can be associated with the disease.

In a clinical context, a clinician can wish to learn whether an individual's disease can be treated with a known treatment. Using graphical interfaces such as described in greater detail below with reference to FIGS. 15A-15L, the clinician can select a genome for investigation and query terms to select only variants having type missense or nonsense, and that are located in an exon. The clinician can further narrow the resulting list of variants by selecting a query term to select only variants that are known to be associated with the disease. The clinician then can run a report, which preferably lists only variants that are known to be associated with the disease and further that are clinically actionable, e.g., that have an FDA approved drug. Based on the report, the clinician then can prepare a treatment plan for the individual.

Computer-Based Systems for Implementing Methods 300, 700, and 1000

Figure 14:
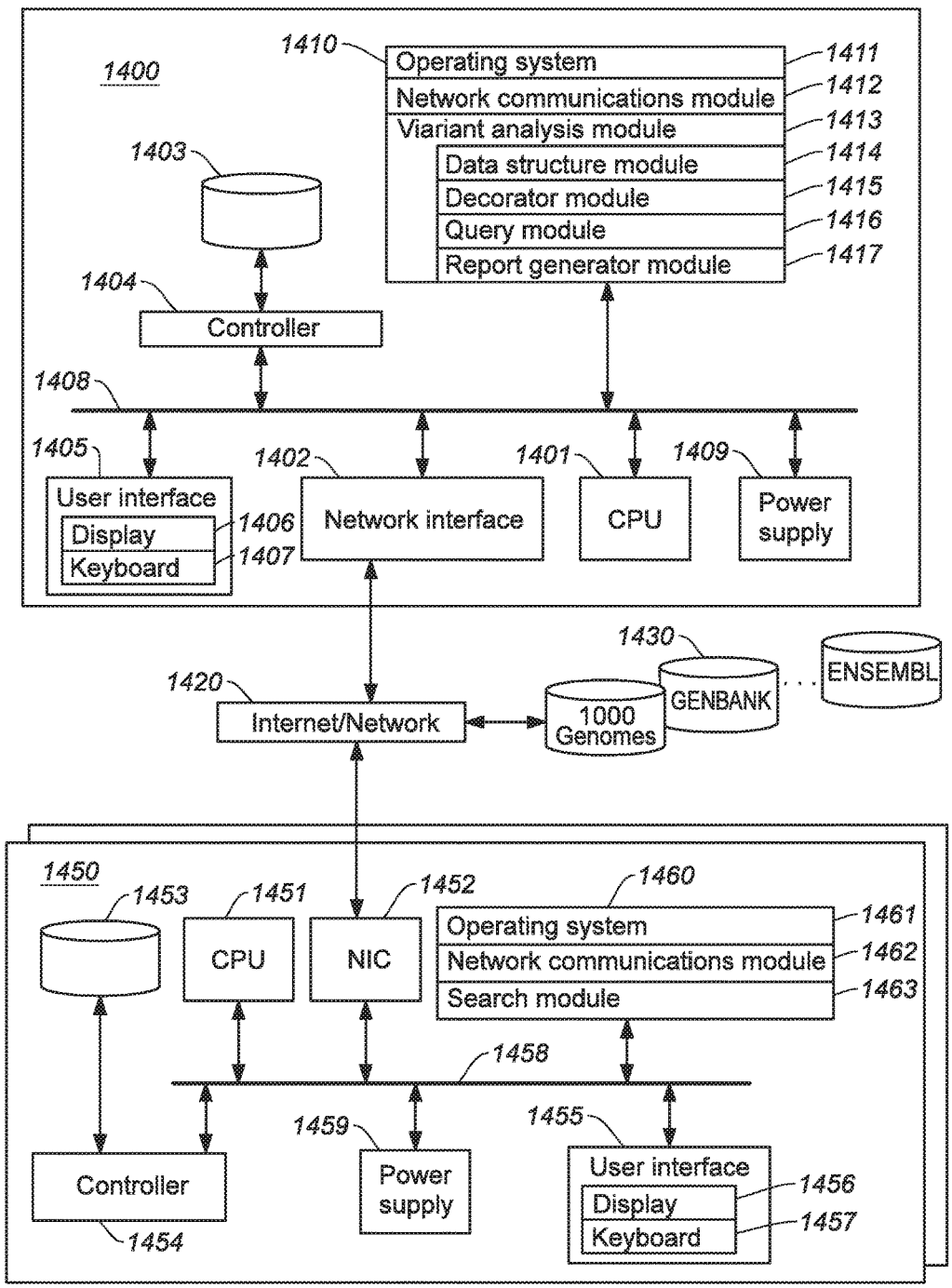
FIG. 14 schematically illustrates an exemplary computer-based system configured to generate, modify, store, and query discrete data structures corresponding to genetic variants within a plurality of genomes, according to some embodiments of the present invention.

Now that an overview of the methods of the present invention, e.g., for generating, modifying, storing, and querying data structures corresponding to genetic variants within a plurality of genomes using steps such as described above with reference to method 300 of FIG. 3, including generating and using genome masks in conjunction with the same such as described above with reference to method 700 of FIG. 7 and method 1000 of FIG. 10, a description of one exemplary suitably programmed computer configured to implement such methods now will be described with reference to FIG. 14.

The computer-based architecture illustrated in FIG. 14 includes variant system 1400 that is configured to implement methods 300, 700, and 1000; a plurality of remote curated data sources 1430 that are configured to store curated intrinsic, extrinsic, or genomic information relating to genetic variants, such as 1000 Genomes, GENBANK, or ENSEMBL, that are configured to communicate with variant system 1400 via the Internet or other network 1420; and a plurality of remote clients 1450 that are configured to communicate with variant system 1400 via the Internet or other network 1420, are configured to receive user queries, to submit such queries to variant system 1400, to receive the results of such queries from variant system 1400, and to output the results of such queries to the user. As noted above, the information within one or more of remote data sources 1430 can be converted to local storage within system 1400. It will be appreciated that remote curated data sources 1430 can be operated by an independent entity and need not necessarily be considered to be part of the present invention; accordingly, the architectural details of such data sources 1430 are omitted from FIG. 14 for simplicity.

As illustrated in FIG. 14, variant system 1400 includes one or more processing units (CPU's) 1401 (e.g., processing means), a network or other communications interface (NIC) 1402 (e.g., networking means), one or more non-volatile, non-transitory, computer readable memory devices or media such as magnetic disk storage or persistent devices 1403 (e.g., memory means or storage means) optionally accessed by one or more controllers 1404, a user interface 1405 including a display 1406 and a keyboard 1407 or other suitable device for accepting user input, a memory 1410 (e.g., memory means or storage means), one or more communication busses 1408 for interconnecting the aforementioned components, and a power supply 1409 for powering the aforementioned components. Data in memory 1410 can be seamlessly shared with non-volatile memory 1403 using known computing techniques such as caching. Memory 1410 or memory 1403 can include mass storage that is remotely located with respect to the central processing unit(s) 1401. In other words, some data stored in memory 1410 or memory 1403 can be hosted on computers that are external to variant system 1400 but that can be electronically accessed by system 1400 over an Internet, intranet, or other form of network or electronic cable using network interface 1402. In one illustrative embodiment, system 1400 is a personal computer. Of course, the present methods equivalently can be performed using a custom hardware with dozens or more processors connected in parallel, at even greater speed.

Memory 1403 preferably stores one or more databases that store data structures corresponding to genetic variants, as well as genome masks and nucleic acid characteristics extracted from remote curated data sources 1430 for use in modifying or "decorating" such data structures. Preferably, such database(s) respond appropriately to queries from various modules that can be stored within memory 1410, such as described further below. Memory 1410 preferably stores an operating system 1411 that is configured to handle various basic system services and to perform hardware dependent tasks, and a network communications module 1412 that is configured to connect variant system 1400 to various other computers such as remote curated data sources 1430 and to clients 1450 via one or more communication networks 120, such as the Internet, other wide area networks, local area networks (e.g., a local wired or wireless network can connect the variant system 1400 to the remote client 1450), metropolitan area networks, and so on.

Memory 1410 preferably also stores a variant analysis module 1413 that includes a plurality of modules configured to cause processing unit 1401 to execute the various steps of method 100. For example, variant analysis module 1413 includes a data structure module 1414 configured to cause processing unit 1401 to obtain digital representations of variants within a plurality of genomes from the 1000 Genomes website or other suitable remote curated data source 1430, such as described above with reference to step 301 of method 300 illustrated in FIG. 3. As noted herein, in one illustrative embodiment the digital representations are VCF files, although other suitable formats can be used. Data structure module 1414 illustrated in FIG. 14 further is configured to cause processing unit 1401 to convert the digital representations of variants within a first genome of the plurality into a plurality of discrete data structures, in which each data structure uniquely corresponds to only one genetic variant in the first genome, and each data structure includes a data field having a unique identifier for the corresponding variant and a data field having a unique identifier for the first genome, such as described above with reference to step 302 of method 300. Data structure module 1414 illustrated in FIG. 14 further is configured to cause processing unit 1401 to determine whether each genetic variant within each additional genome corresponds to an existing data structure, and if so to modify that existing data structure to include a data field having a unique identifier for that additional genome, and if not then to convert the digital representation of that variant into a discrete data structure uniquely corresponding to that variant, including data fields having a unique identifier for that variant and a unique identifier for that additional genome, as described above with reference to steps 303-305 of method 300. Data structure module 1414 also is configured to cause processing unit 1401 to store the data structures within a database in memory 1403, as described above with reference to step 307 of method 300.

Variant analysis module 1413 illustrated in FIG. 14 also includes a decorator module 1415 configured to cause processing unit 1401 to modify the data structures generated by data structure module 1414 so as to include additional data fields describing extrinsic information about the corresponding variants, such as described above with reference to step 306 of method 300. In particular, decorator module 1415 can be configured to cause processing unit 1401 to generate genome masks, to store such genome masks within the database in memory 1403, to generate local, reformatted versions of remote curated data sources and to store those versions within the database in memory 1403 and to use such genome masks in conjunction with remote databases 1430 or local versions thereof to decorate data structures, such as described above with reference to method 700 of FIG. 7 and method 1000 of FIG. 10. Decorator module 1413 can be configured to cause processing unit 1401 to perform such modifications either before or after data structure module 1414 stores the data structures within the database in memory 1403.

Variant analysis module 1413 illustrated in FIG. 14 also includes a query module 1416 configured to cause processing unit 1401 to receive a query term identifying genomes and an operation to be performed such as described above with reference to step 308 of method 300 of FIG. 3. Preferably, query module 1416 causes processing unit 1401 to cause display 1406 to display a graphical user interface (GUI) that allows the user to readily define the query term. For example, the GUI can include a list of genomes that are available for analysis and a mechanism configured to permit the user to select from the list, e.g., by presenting check boxes or radio buttons adjacent the genomes that the user can select, or by allowing the user to highlight within the list the genomes of interest, using keyboard 1407 or other suitable user interface device coupled to variant system 1400. The GUI also can be configured to facilitate the user's selection of a particular operation to be perform on the selected genomes, such as by allowing the user to "drag and drop" or otherwise segregate genomes into lists that respectively define the operation to be performed. For example, genomes within which the variants are to be required can be placed in a first list, and genomes within which the variants are to be excluded can be placed in a second list. The GUI also can include a list of additional query terms that can be added during the query, e.g., that prompt the user to select from among the various types of nucleic acid characteristics that can be stored within the data fields of the data structures, such as with check boxes, radio buttons, or one or more lists that allow the user to highlight any filters of interest. Preferably, such additional query terms are categorized by type so as to facilitate the user's selection of query terms appropriate to the user's research goals. Additionally, as noted below, query module 1416 can cause processing unit 1401 to accept query terms that are defined remotely, e.g., at remote client 1450. Exemplary GUIs for defining queries and receiving the output of queries are described in greater detail below with reference to FIGS. 15A-15L.

Query module 1416 also causes processing unit 1401 to search the data structures stored within the database of memory 1403 for data fields that match the query term and satisfy the operation, such as described above with reference to step 309 of method 300. Based on the database's response to the query, query module 1416 causes processing unit 1401 to generate an output that uniquely identifies a genetic variant and any genomes that contain that variant, such as described above with reference to step 310 of method 300. A variety of suitable outputs are described herein, and others readily can be envisioned. For example, query module 1416 can cause processing unit 1401 to cause display 1406 to display a list of variants or genomes containing those variants, or a map that graphically represents the locations of such variants within a genome, or can store such a list or map within memory 1403. Alternatively, query module 1416 can cause processing unit 1401 to pass the output to report generator module 1417, which can generate a report that can include a representation of genetic variants within the output that are clinically actionable, and a representation of treatments that can be available for those genetic variants, and can be edited by the user. Report generator module 1417 can cause processing unit 1401 to cause such a report to be stored in memory 1403, to be displayed on display 1406, to be printed on an associated printer (not illustrated), or otherwise provided to the user. An exemplary report is described in greater detail below with reference to FIG. 15K.

Optionally, variant system 1400 is connected via a network such as the Internet 1420 to one or more remote clients 1450, which permit users who are remote from variant system 1400 to submit and receive the results of queries to variant system 1400. Typically, remote client 1450 can include one or more processing units (CPUs) 1451; a network or other communications interface (NIC) 1452; one or more magnetic disk storage and/or persistent storage devices 1453 that are accessed by one or more controllers 1454; a user interface 1455 including a display 1456 and a keyboard 1457 or other suitable device configured to accept user input; a memory 1460; one or more communication busses 1458 for interconnecting the aforementioned components; and a power supply 1459 for powering the aforementioned components. In some embodiments, data in memory 1460 can be seamlessly shared with non-volatile memory 1453 using known computing techniques such as caching.

The memory 1460 preferably stores an operating system 1461 configured to handle various basic system services and to perform hardware dependent tasks; and a network communication module 1462 that is configured to connect remote client 1450 to other computers such as variant system 1400. The memory 1460 preferably also stores search module 1463 that is configured to cause processing unit 1451 to receive user input defining query terms in a manner analogous to query module 1416, to transmit such query terms to query module 1416 for use in searching memory 1403 of variant system 1400. Search module 1463 can cause processing unit 1451 to receive a response from query module 1416 based on the query terms, and to output such response in a manner analogous to that described above, e.g., can cause display 1456 to display a list or map of variants or genomes.

Note that memories 1403 and 1410 of variant system 1400 and memories 1453 and 1460 of remote client 1450 can include any suitable internal or external memory device, such as FLASH, RAM, ROM, EPROM, EEPROM, or a magnetic or optical disk or tape. In one illustrative embodiment, the present data structures, genome masks, and local versions of remote curated data sources are stored in a Lucene database within memory 1403 of variant system 1400.

Exemplary graphical user interfaces (GUIs) that can be generated during use of system 1400 are described further below with reference to FIGS. 15A-15L and Examples 2-5.

Example 1

Methods 300, 700, and 1000 respectively described further above with reference to FIGS. 3, 7, and 10 were implemented using a dual-core Macintosh personal computer. Specifically, a digital representation of the genetic variants within Craig Venter's genome was obtained from the 1000 Genomes website, in a version 4.1 VCF file having the format defined online by the 1000 Genomes Project at. An exemplary section of the VCF file is reproduced below:

| #CHROM | POS | ID | REF | ALT | QUAL | FILTER | INFO | FORMAT | Venter |
|---|---|---|---|---|---|---|---|---|---|
| chr20 | 24939990 | . | G | C | 222 | PASS | DP=10 | GT:AD:DP | 1/1:7,3:10 |
| chr20 | 25457049 | . | GCTCCCAC | GC | 217 | PASS | INDEL;DP=10 | GT:AD:DP | 3/1:4,5:10 |
| chr20 | 32664864 | . | cc | cCACc | 214 | . | INDEL;DP=10 | GT:AD:DP | 1/1:5,5:10 |

It can be seen that the first listed genetic variant corresponds to a SNP in which the reference allele "G" is replaced by the variant allele "C." The VCF file was parsed using a data structure module, which extracted the basic genomic positional information along with the genome specific details for the "Venter" genome. Specifically, the data structure module converted the below line:

chr20 24939590. G C 222 PASS DP=10 GT:AD:DP 1/1:7,3:10 into a variant intermediate data structure corresponding to a variant type of "SNP" and having the following data fields, with corresponding field names, in which certain alphanumeric fields can be enclosed with double quotes:

| | |
|---|---|
| "hash": | "200024939590G_C" |
| "chromosome:" | "20" |
| "start": | 24939590 |
| "end": | 24939590 |
| "ref": | "G" |
| "alt": | "C" |
| "varType": | "snp" | as well as a genome intermediate data structure having the following data fields:

| | |
|---|---|
| "hash": | "200024939590G_C" |
| "genome": | "Venter" |
| "quality": | "222.0" |
| "filter": | ["PASS"] |
| "zygosity": | "1|1" |
| "refAllelicDepth": | "7" |
| "altAllelicDepth": | "3" |
| "totalDepth": | "10" |

The genome intermediate data structure was stored in a temporary Genome database with the hash value corresponding to the variant intermediate data structure.

The variant intermediate data structure then was run through a decorator module that implemented step 306 of method 300 to add extrinsic data from curated data sources GENBANK and ENSEMBL with regards of the position of the variant relative to genes. Specifically, a decorator module used genome masks for each of these curated data sources, constructed as described above with reference to method 1000, to submit queries to local versions of remote respective curated data sources for gene information in accordance with method 700. A local, reformatted GENBANK data source was prepared using a method such as described further below, and responded to the query with the gene name "CST7" and the gene identifier "8530," while local, reformatted ENSEMBLE data source was prepare and responded to the query with the gene name "CST7" and the gene identifier "ENSG00000077984." Neither of the curated data sources responded that the gene was present in a UTR region, or in a non-coding RNA region, nor in a splice junction. Accordingly, the decorator module modified the variant data structure to include the following data fields, with corresponding field names in which the prefix "ensembl" differentiates the data fields derived from ENSEMBL from those derived from GENBANK:

| | |
|---|---|
| "geneName": | "CST7" |
| "geneID": | "8530" |
| "utr": | "—" |
| "ncrna": | "—" |
| "splicejunction": | "—" |
| "ensemblgeneName": | "CST7" |
| "ensemblgeneID": | "ENSG00000077984" |
| "ensemblutr": | "—" |
| "ensemblncrna": | "—" |
| "ensemblsplicejunction": | "—" |

In the above example, the "genName" data field stores the symbol for the gene, following the HUGO gene nomenclature committee; the "geneID" data field stores the internal identifier used either by GENBANK and REFSEQ or by ENSEMBL; the "utr" data field stores an indication of whether a position is ("+") or is not ("−") in a 5' or 3' UTR region; the "ncrna" data field stores an indication of whether a position is ("+") or is not ("−") in a non-coding RNA region; and the "splicejunction" data field indicates whether a position is ("+") or is not ("−") in a splice junction region.

The decorator module then used genome masks for each of these curated data sources, constructed as described above with reference to method 1000, to submit queries to the respective curated data sources for information about flanking genes in accordance with method 700. Specifically, genome masks corresponding to a "near flank" that identified whether a given position was within 500 base pairs from the start or end of a gene were constructed for both the 5' and 3' sides, for both of the REFSEQ and ENSEMBL locally stored databases. Genome masks corresponding to a regular "flank" that identified whether a given position was within 10,000 base pairs from the start or end of a gene also were constructed for both the 5' and 3' sides, for both of the REFSEQ and ENSEMBL databases. The decorator module modified the variant intermediate data structure to store the following query responses, with corresponding field names in which the prefix "ensembl" differentiates the data fields derived from ENSEMBL from those derived from REFSEQ:

| | |
|---|---|
| "flank3": | "APMAP" |
| "flank5": | "—" |
| "nearflank3": | "—" |
| "nearflank5": | "—" |
| "splicejunction": | "—" |
| "ensemblflank3": | "APMAP" |
| "ensemblflank5": | "—" |
| "ensemblnearflank3": | "—" |
| "ensemblnearflank5": | "—" |

In the above example, the "flank3" data field stores an indication of whether the variant is within 10,000 base pairs on the 3' side of a gene; the "flank5" data field stores an indication of whether the variant is within 10,000 base pairs on the 5' side of a gene; the "nearflank3" data field stores an indication of whether the variant is within 500 base pairs on the 3' side of a gene; and the "nearflank5" data field stores an indication of whether the variant is within 10,000 base pairs on the 5' side of a gene.

The decorator module then submitted a query based on the chromosome and position of the variant to a local version of the University of Washington's database of segmental duplication information. The database responded with no value, so the decorator module added the following data field with null value to the variant intermediate data structure:

"segdupsegments": "–"

As a point of comparison, a non-null value can have the exemplary format:

| | |
|---|---|
| "segdupsegments": | "20: 1584464-1586007 (0.966077739), 20: 1901736-1903283 (0.966077739)" |

The decorator module then submitted a query based on the chromosome and position of the variant to a local version of the remote dbSNP database, responsive to which the database provided the value "rs1056033," so the decorator module added the following data field to the variant intermediate data structure:

"dbsnp": "rs1056033".

The decorator module then used the SIFT and PolyPhen qualitative and quantitative database from ENSEMBL to determine the effect the variant's effect on the corresponding exon. Specifically, using appropriate genome masks and queries to the local GENBANK and ENSEMBL databases, the following data fields relating to exon and missense regions of the genome were generated, again where "ensembl" in the preamble of the field name distinguishes the information from ENSEMBL from that from GEN-BANK:

| | |
|---|---|
| "exon": | "synonymous" |
| "missense": | "–" |
| "ensemblexon": | "synonymous" |
| "ensemblmissense": | "–" |

Then, the decorator module retrieved the PolyPhen and SIFT scores and stored the scores in the variant intermediate data structure in the following format:

| | |
|---|---|
| "polyphenPrediction": | "benign" |
| "polyphenscore": | "1.0" |
| "siftscore": | "1.0" |

In the above example, the change caused by the variant is synonymous, so the prediction is "benign" and the SIFT and PolyPhen scores are "1.0." As a point of comparison, a variant predicted to be damaging instead can include data fields such as the following:

| | |
|---|---|
| "exon": | "nonsense" |
| "missense": | "–" |
| "ensemblexon": | "nonsense" |
| "ensemblmissense": | "–" |
| "polyphenPrediction": | "probably damaging" |
| "polyphenscore": | "2.64" |
| "siftscore": | "0.05" |

The decorator module then submitted a query based on the chromosome and position of the variant to a local version of the remote PFAM database, responsive to which the database provided the value "PF00031," so the decorator module added the following data field to the variant intermediate data structure:

"pfam": "PF00031".

The decorator module then formed data fields within the variant intermediate data structure describing allele frequency, based on a local version of the remote database of the variants identified by the 1000 Genomes Project:

| | |
|---|---|
| "af": | 0.6 |
| "amr_AF": | 0.6 |
| "asn_AF": | 0.92 |
| "afr_AF": | 0.34 |
| "eur_AF": | 0.52 |

Following addition of the above-described data fields to the variant intermediate data structure, the data structure module then merged together the variant intermediate data structure and the genome intermediate data structure to form a single data structure containing intrinsic and extrinsic information about the corresponding genetic variant and genomic information about Craig Venter's genome. The resulting data structure was stored in a searchable Lucene database.

The data structure module then parsed the second line within the above-noted excerpt from Craig Venter's VCF file as follows:

| | | | | | | |
|---|---|---|---|---|---|---|
| chr20 | 25457049 | . | GCTCCCAC | GC | 217 | PASS |
| INDEL;DP=10 | GT:AD:DP | 0/1:4,5:10. | | | | |

Based on such parsing, the data structure module then formed a genome intermediate data structure having the following data fields:

| | |
|---|---|
| "hash": | "200025457051TCCCACD" |
| "genome": | "Venter" |
| "quality": | "217.0" |
| "filter": | ["PASS"] |
| "zygosity": | "0|1" |
| "refAllelicDepth": | "4" |
| "altAllelicDepth": | "5" |
| "totalDepth": | "10" | as well as a variant intermediate data structure having the following data fields:

| | |
|---|---|
| "hash": | "200025457051TCCCACD" |
| "chromosome:" | "20" |
| "start": | 25457051 |
| "end": | 25457049 |
| "ref": | "TCCAC" |
| "alt": | "" |
| "varType": | "del", | in which it can be seen that the variant type is a deletion ("del") because there is no alternate allele.

The decorator module then submitted queries for extrinsic information associated with this variant analogous to those described above, and stored the received results in the following data fields within the variant intermediate data structure:

| | |
|---|---|
| "geneName": | "NINL" |
| "geneID": | "22981" |
| "utr": | "—" |
| "ncrna": | "—" |
| "splicejunction": | "—" |
| "ensemblgeneName": | "NINL" |
| "ensemblgeneID": | "ENSG00000101004" |
| "ensemblutr": | "—" |
| "ensemblncrna": | "—" |
| "ensemblsplicejunction": | "—" |
| "flank3": | "—" |
| "flank5": | "—" |
| "nearflank3": | "—" |
| "nearflank5": | "—" |
| "splicejunction": | "—" |
| "ensemblflank3": | "—" |
| "ensemblflank5": | "—" |
| "ensemblnearflank3": | "—" |
| "ensemblnearflank5": | "—" |
| "segdupsegments": | "—" |
| "dbsnp": | "rs34410422" |
| "exon": | "—" |
| "missense": | "—" |
| "ensemblexon": | "—" |
| "ensemblmissense: | "—" |
| "polyphenPrediction": | "—" |
| "polyphenscore": | "0.0" |
| "siftscore": | "1.0" |
| "pfam": | "—" |
| "af": | 0.0 |
| "amr_AF": | 0.0 |
| "asn_AF": | 0.0 |
| "afr_AF": | 0.0 |
| "eur_AF": | 0.0 |

Following addition of the above-described data fields to the variant intermediate data structure, the data structure module merged together the variant intermediate data structure and the genome intermediate data structure to form a single data structure containing intrinsic and extrinsic information about the corresponding genetic variant and genomic information about Craig Venter's genome. The resulting data structure was stored in a searchable Lucene database.

The data structure module then parsed the third line within the above-noted excerpt from Craig Venter's VCF file as follows:

```
chr20  32664864  .  cc  cCAGc214  .  INDEL;DP=10
GT:AD:DP  1/1:5,5:10
```

Based on such parsing, the data structure module then formed a genome intermediate data structure having the following data fields:

| | |
|---|---|
| "hash": | "2000326648661_AGC" |
| "genome": | "Venter_exome_CLIA_lab" |
| "quality": | "217.0" |
| "filter": | [ ] |
| "zygosity": | "0|1" |
| "refAllelicDepth": | "100" |
| "altAllelicDepth": | "85" |
| "totalDepth": | "188" | as well as a variant intermediate data structure having the following data fields:

| | |
|---|---|
| "hash": | "2000326648661_AGC" |
| "chromosome:" | "20" |
| "start": | 32664866 |
| "end": | 32664866 |
| "ref": | "" |
| "alt": | "AGC" |
| "varType": | "ins", | in which it can be seen that the variant type is an insertion ("ins") because there is no reference allele.

The decorator module then submitted queries for extrinsic information associated with this variant analogous to those described above, and stored the received results in the following data fields within the variant intermediate data structure:

| | |
|---|---|
| "geneName": | "RALY" |
| "geneID": | "22913" |
| "utr": | "—" |
| "ncrna": | "—" |
| "splicejunction": | "—" |
| "ensemblgeneName": | "RALY" |
| "ensemblgeneID": | "ENSG00000125970" |
| "ensemblutr": | "—" |
| "ensemblncrna": | "—" |
| "ensemblsplicejunction": | "—" |
| "flank3": | "—" |
| "flank5": | "—" |
| "nearflank3": | "—" |
| "nearflank5": | "—" |
| "splicejunction": | "—" |
| "ensemblflank3": | "—" |
| "ensemblflank5": | "—" |
| "ensemblnearflank3": | "—" |
| "ensemblnearflank5": | "—" |
| "segdupsegments": | "—" |
| "dbsnp": | "rs71708002" |
| "exon": | "—" |
| "missense": | "—" |
| "ensemblexon": | "—" |
| "ensemblmissense: | "—" |
| "polyphenPrediction": | "—" |
| "polyphenscore": | "0.0" |
| "siftscore": | "1.0" |
| "pfam": | "—" |
| "af": | 0.0 |
| "amr_AF": | 0.0 |
| "asn_AF": | 0.0 |
| "afr_AF": | 0.0 |
| "eur_AF": | 0.0 |

Following addition of the above-described data fields to the variant intermediate data structure, the data structure module merged together the variant intermediate data structure and the genome intermediate data structure to form a single data structure containing intrinsic and extrinsic information about the corresponding genetic variant and genomic information about Craig Venter's genome. The resulting data structure was stored in a searchable Lucene database.

As noted above, in some circumstances it can reduce the amount of computational power and delay to generate a locally stored and reformatted version of a curated data source. For example, the remote REFSEQ curated data source included a text file that lists genes, exons, and the like the following format:

```
gene    complement(16101279..16124973)
        /gene="NBEAP3"
        /gene_synonym="BCL8C"
```

/note="neurobeachin pseudogene 3; Derived by automated computational analysis using gene prediction method: Curated Genomic."

```
/pseudo
/db_xref="GeneID:100418905"
/db_xref="HGNC:40004"
```

Such a multi-line format was parsed and converted into a format suitable for use in a Lucene database, for use in relatively quickly constructing genome masks and decorating the present data structures based on such genome masks. For example, the above REFSEQ file was converted into the following locally stored database entries:

```
stored<e:16124973>
stored,indexed,tokenized,omitNorms<f:16101279-16124973>
stored<hash:60315800>
stored,indexed,tokenized,omitNorms<i:100418905>
stored,indexed,tokenized,omitNorms<n:NBEAP3>
stored,indexed,tokenized,omitNorms<o:->
stored<s:16101279>
stored<tss:16124973>
```

The above format means the following values for information relevant to generating the present genome masks and data structures:
Chromosome: 22 (because REFSEQ file hs_ref_GRCh37.p9_chr22.gbs was parsed, it can be inferred that the data is for chromosome 22)
Start: 16101279
End: 16124973
Gene Name: NBEAP3
Gene ID: 100418905
Strand/Orientation:—(Negative)

The decorator module included the following exemplary code for submitting a query to retrieve the above information during step 703 of method 700:

```
fGeneSource = FeatureSource.getRefSeqGeneSource(theChromosome);
if (fGeneSource.getFeatureMask( ).test(aVariant)) {
    Feature aGeneFeature =
    fGeneSource.findParentByPosition(aVariant.getStart( ));
    if (aGeneFeature != null) {
        aVariant.setGeneName(aGeneFeature.getGeneName( ));
        aVariant.setGeneID(aGeneFeature.getGeneID( ));
    }
}
```

Example 2

Figure 15A:
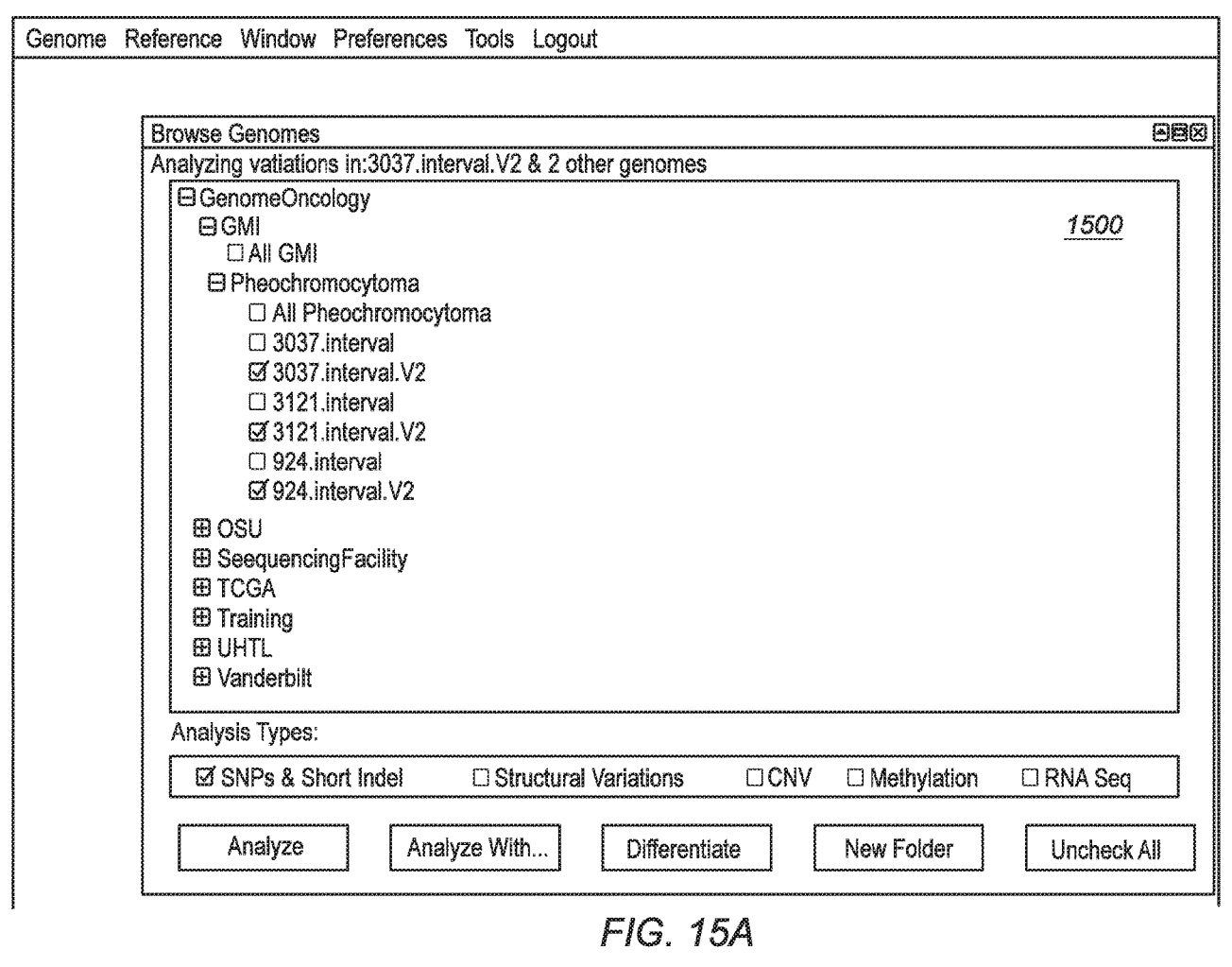

Several exemplary queries were submitted to database storing data structures prepared analogously to those described above in Example 1. Specifically FIG. 15A illustrates a first GUI 1500 generated by system 1400 that permitted a user to select one or more genomes for analysis, as well as to select the type of operation to be performed on those genomes. In this exemplary interface, the genomes available for analysis are listed in a "tree" format, in which different genome sources such as "GMI," "OSU" and the like are listed. Selection of one of such sources presented additional categories of genomes available for analysis, such as the "Pheochromocytoma" category illustrated in FIG. 15A. Selection of such a category then presented the unique alphanumeric identifiers of one or more specific genomes available for analysis, e.g., "3037.interval.V2," "3121.interval.V2," and "924.interval.V2" illustrated in FIG. 15A. A check box was presented next to the alphanumeric identifier for each genome, permitting the user to select one or more genomes to be analyzed. Note that the interface permitted the user to select genomes optionally from different categories or sources than one another.

Exemplary GUI 1500 illustrated in FIG. 15A further included various analysis options from among which the user can select. For example, GUI 1500 included a region labeled "Analysis Types" that lists categories of analysis types that can be available, e.g., SNPs and short insertions or deletions ("indel"), structural variations, copy number variations ("CNV"), methylation, or RNA sequence ("RNA seq."). In this example, only analysis types that are appropriate to the particular genomes selected by the user are available for selection. For example, here the three selected genomes included information about SNPs or short insertions or deletions, so that analysis type was automatically selected using a check box.

The lower region of GUI 1500 also provided additional analytical options among which the user can select, e.g., "analyze," "analyze with . . . " "differentiate," "new folder," and "uncheck all". Selection of the "analyze" option means that the user wishes to perform the union or intersect operations upon the selected genomes, such as described in greater detail above with reference to FIG. 1B or 1D, and thus to list all of the genetic variants contained within the selected genomes, or all of the genetic variants shared between the selected genomes. Further description of GUIs associated with selection of the "analyze" option is provided further below with reference to FIGS. 15B-1 to 15E and 15H-1 to 15L. Selection of the "differentiate" option means that the user wishes to perform the differentiate or symmetric differentiate operations upon the selected genomes, such as described in greater detail above with reference to FIGS. 1C and 1E-1H. Further description of GUIs associated with selection of the "differentiate" option is provided further below with reference to FIGS. 15F-1 to 15G-2. Selection of the "analyze with . . . " option means that the user wishes to use a previously defined method of analysis, e.g., a previously selected analytical option and set of query terms, which can be stored at system 1400. Selection of the "new folder" option permits the user to add a new folder to the genome source tree, and to add another genome for analysis. Selection of the "uncheck all" option permits the user to deselect any previously selected options.

Figure 15B-3:
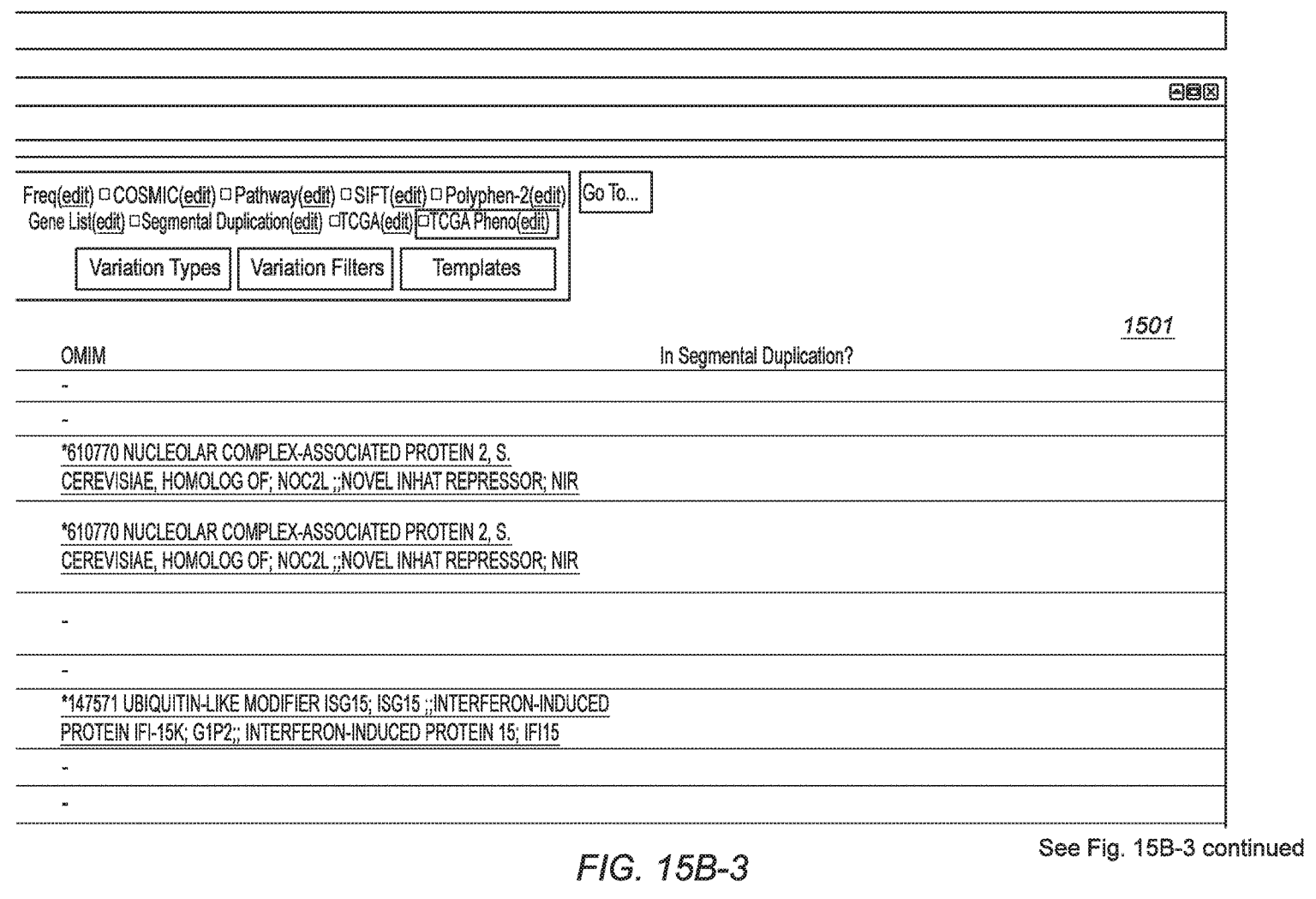

As noted above, selection of the "analyze" option within GUI 1500 permits the user to perform a union or intersect operation upon the selected genomes. GUI 1501 illustrated in FIGS. 15B-1, 15B-2, and 15B-3 illustrates an exemplary output of genetic variants that system 1400 generated based upon the user's selection of the three genomes having the unique alphanumeric identifiers "3037.interval.V2," "3121.interval.V2," and "924.interval.V2" and the "Analyze" option illustrated in FIG. 15A, via which system 1400 performed a "union" operation on the selected genomes. In FIG. 15B-1, it can be seen that the output within GUI 1501 included an identifier of the genome, e.g., "3037.interval.V2" for the first listed genetic variant, the zygosity of the genome for that variant (0|1), the read quality for that variant (q=43), the number N of selected genomes that include that variant (1), the percent of the selected genomes that include that variant (33%), the chromosome on which that variant is present (1), the start position of the variant (865665), the end position of the variant (865665), the variant type "VT" (snp), the reference allele (G), the alternate allele (A), the dbSNP (rs145442390), the average allele frequency "AF" (0), the allele frequency for the American demographic "AMR_AF" (0), the allele frequency for the Asian demographic "ASN_AF" (0), the allele frequency for the African demographic "AFR_AF" (0), and the allele frequency for the European demographic (0). In FIG. 15B-2, which is a continuation of FIG. 15B-1, it can be seen that the output within GUI 1501 further included a name or identifier of a gene in which the variant is present, e.g., SAMD11 for the first listed variant, an indication of a coding DNA sequence "CDS" in which that variant is present (R68Q), the SIFT score for that variant (0.16), the PolyPhen score for that variant (benign), the PolyPhen-2 "PP2" score for that variant (0.001), the PFAM for that variant (PF07647), the TCGA for that variant (no value), and the OMIM for that variant (no value). In FIG. 15B-3, which is a continuation of FIG. 15B-2, it can be seen that the output within GUI 1501 further included a column for segmental duplication; although the first listed variant did not include information within this particular column, it may be seen that other variants did. It should be appreciated that other types and formats of information suitably can be output in GUI 1501. As can be seen in FIG. 15B-2, GUI 1501 included an "export" button permitting the user to export the results to another file format, such as Excel, for further use.

Note that in FIG. 15B-1, it can be seen that some variants were unique to a given genome (e.g., N=1, 33% of genomes having the variant), while other variants were shared between two genomes (e.g., N=2, 67% of genomes having the variant), while still other variants were shared between all three genomes (e.g., N=3, 100% of genomes having the variant). GUI 1501 permitted the user to select the "Fewer Than or Equal To" or the "More Than or Equal To" option, or both, and thereby to enter a minimum or maximum number of genomes, or both, that shared a given variant in order for that variant to be displayed, and thus performed the "intersect" operation on the selected genomes. For example, by selecting "More Than or Equal To" and entering the value 67%, the user required that only variants shared by two or more genomes be displayed, and by selecting "More than or Equal to" and entering the value 100%, the user instead required than only variants shared by all three genomes be displayed. Depending on the particular number of genomes being analyzed, the percentages available for entry or selection in these portions of GUI 1501 automatically updated to appropriate values.

Exemplary GUI 1501 also provided additional options permitting the user to submit further query terms so as to narrow the resulting list of variants. For example, the upper region of GUI 1501 included a plurality of query terms such as "zygosity," "quality," and the like. Selection of a given check box permitted the user to submit an additional query term so as to include only variants that satisfy that query term; the user could select as many of such additional query terms as can be desired, and the listing of variants automatically updated as the system applied the additional query terms. For example, GUI 1502 illustrated in FIGS. 15C-1 and 15C-2 included an output of variants that was analogous to that in FIGS. 15B-1, 15B-2, and 15B-3, but to which additional query terms were applied, specifically a zygosity query term requiring only heterozygous ("het") variants to be listed, a dbSNP query term requiring only variants that were not listed in the dbSNP database to be listed (dbSNP "out"), and an allele frequency query term requiring only variants with an allele frequency of less than 0.001 to be listed. A particular threshold value for allele frequency (such as less than 0.001) was selected by clicking the "edit" link next to the allele frequency filter, and entering the value within a pop-up window. A combination of query terms such as illustrated in FIGS. 15C-1 and 15C-2 can be useful for identifying variants that are not already well-characterized. Specifically, the dbSNP "out" query term selected only non-documented variants, and variants with relatively low allele frequencies are likely to be unfavorable for the organism and thus unlikely to be found under normal conditions. Additionally, although not shown in FIGS. 15C-1 and 15C-2, additional query terms for the variant locations exon or splicesite were selected, and additional query terms for the variant types missense or nonsense were selected, because variants having such locations and types are relatively likely to cause changes to individuals having those variants. As can be seen in FIGS. 15C-1 and 15C-2, the list of variants obtained using such additional query terms was significantly shorter than that of FIGS. 15B-1, 15B-2, and 15B-3; such additional query terms thus may help to focus a user conducting research on genetic variants of potential relevance to the user's research problem.

FIG. 15D illustrates GUI 1503 that was accessed by selecting the "Genes" tab at the top of GUI 1502, and further permitted the user to identify genes that contain one or more variants. In GUI 1503, the user selected "Fewer Than or Equal To" and entered the value 67% and also selected "More Than or Equal To" and entered the value 67%, requiring that only variants that were shared by exactly 67% of the genomes (that is, by exactly two of the genomes) be displayed, e.g., so that the query included the "intersect" operation. Additionally, the user selected the option "SNP gene variants," requiring that only SNP variants that are located within genes be displayed. In the first entry illustrated in GUI 1503, continuing with the exemplary genomes entered using GUI 1500 and query terms entered using GUI 1502, it can be seen that genomes having unique alphanumeric identifiers "3124.interval.V2" and "924.interval.V2" both contain variants located within the gene named DCHS2 and having identifier 54796, having type SNP/small InDel (insertion/deletion), located on chromosome 4, described as being involved in dachsous 2 (*Drosophila*), for which the severity is "Missense, SIFT<0.1". In this example, it can be seen that of all of the variants within the three genomes selected using GUI 1500, only nineteen of such variants were present in exactly two of the genomes and are located within a known gene.

FIG. 15E illustrates GUI 1504 which is analogous to that illustrated in FIG. 15D, but in which the user selected "More Than or Equal To" and entered the value "All," requiring that only variants that are shared by all of the genomes (that is, by exactly three of the genomes in this example) be displayed e.g., so that the query included the "intersect" operation. For analyses in which all three of the genomes being studied have the same disease as one another, such a selection can display genes that are more likely than other genes to be associated with that disease. In the first entry illustrated in GUI 1504, continuing with the exemplary genomes entered using GUI 1500 and query terms entered using GUI 1502, it can be seen that the three selected contained variants located within the same gene, specifically a gene named MAX and having identifier 4149, and a gene named PTCHD3 and having identifier 374306. The type, chromosome, description, and severity for the two shared variants are illustrated in FIG. 15E.

As described further above, a sequence of analytical steps such as illustrated in FIGS. 15A-15E can be used in a research context to determine whether a disease can be associated with a genetic variation that can be detected by analyzing variants. By querying for variants shared by any other desired number of genomes by heterozygosity, that are absent from the dbSNP database, that have a relatively low allele frequency, that are present in genes, and that are present in all of the genomes, genes that are present in all three genomes can be identified and can be selected as the subject of further research, e.g., experimental validation. Other combinations of query terms of course may be selected depending on the particular research problem of interest. Using the present systems, methods, and data structures, such an analysis can be completed within a few seconds or less (including the time it takes the user to select the various genomes, operations, and query terms), and thus can greatly accelerate the pace of genomic research.

Example 3

Referring again to GUI 1500 illustrated in FIG. 15A, the user instead selected the "differentiate" option so as to perform differentiate or symmetric differentiate operations on the selected genomes. For example, upon selection of "differentiate," the GUI presented a pop-up window (not illustrated) via which the user selected which of the genomes were "in," and thus have its variants required in the query results, and which of the genomes were "out," and thus have their variants excluded from the query results. FIGS. 15F-1 and 15F-2 illustrate GUI 1505 in which the above-described genome named 924.interval.V2 was selected as "in" or required, and the genomes named 3037.interval.V2 and 3121.interval.V2 were selected as "out" or excluded. GUI 1505 outputted the variants that are required or excluded in different colors than one another, e.g., outputted the required variants in green (represented in FIG. 15F-1 using rectangles), and outputted the excluded variants in red. For the fourth variant listed in GUI 1505 (having start position 888659), it can be seen that all three of the genomes, including the required genome 924.interval.V2, include that variant. In comparison, for the eighth and ninth variants listed (respectively having start positions 1179802 and 1244924) only the required genome 924.interval.V2 included those variants. As illustrated in GUI 1506 of FIGS. 15G-1 and 15G-2, the user selected "More Than or Equal To" and entered the value "all" so as to exclude any variants that are present in the excluded genomes. Accordingly, all of the variants listed in GUI 1506 were outputted in green (represented in FIG. 15G-1 using the rectangle), and represented variants that are unique only to genome 924.interval.V2.

Example 4

Interfaces such as described above also can be used to perform single-genome analyses. For example, a user used GUI 1500 described above with reference to FIG. 15A to select only a single genome for analysis, and selected the "analyze" option—that is, had system 1400 perform the "union" operation on the selected genome—which generated an output of all variants present within that genome such as illustrated in GUI 1507 of FIGS. 15H-1 and 15H-2, for genome "HCC1187_T," which is a tumor genome. In this example, the user selected the variant type query terms missense and nonsense, selected the variant location query term exon, and then selected a desired gene list query term so as to output only variants that were listed in a curated data source as being relevant to a particular disease. Specifically, FIG. 15I illustrates a pop-up menu 1508 that appeared upon selection of the gene list query term option, in which it can be seen that a variety of gene lists were presented, such as the set of genes identified by Washington University as being associated with ovarian cancer ("WashU-GPS-OvarianCancerSet.txt"), a set of genes identified by Washington University as being associated with myeloid disorder ("WashU-GPS-MyeloidDisorderSet.txt"), and the like. The gene lists were provided in a .txt file format. In the illustrated example, the user selected the set of genes identified by Washington University as being associated with a variety of cancers, also referred to as a cancer panel ("WashU-GPS-CancerPanel.txt"). FIGS. 15J-1 and 15J-2 illustrate GUI 1509 which includes an output of variants that is analogous to that illustrated in GUI 1507, but to which a query based on the selected cancer panel gene list further was applied. It can be seen that of the 8,011 variants initially output in GUI 1507, only the seven that were listed in the noted cancer panel gene list were outputted in GUI 1509.

So as to determine whether any gene mutations that can be caused by the variants output in GUI 1509 were clinically actionable, the user selected the "Report" tab at the top of GUI 1509, which caused system 1400 to generate a clinical report based on those variants. Specifically, report generator module 1417 of system 1400 implemented a set of rules to determine whether any genes in which the output variants were present had an associated treatment (that is, were clinically actionable), and included such genes in the report. FIG. 15K illustrates an exemplary GUI 1510 that included such a report for the four genetic variants output in GUI 1509 that report generator module 1417 determined to be clinically actionable, specifically the variants located in genes named ALK, KIT, MET, and RET. Taking the gene named ALK as an example, the report identified the type of genome, here a tumor genome of HCC1187_T; identified the amino acid (AA) variation resulting from the genetic variant, here the variation I1461V; identified the prevalence of the variation, here ALK NSCLC: 3-7%; identified a therapy for mutations in that gene, here Crizonotib, and provided a description of the clinically observed efficacy of that therapy; and provided a reference for that therapy, and a date on which such information within the data structure for that variant was last updated.

In a clinical setting, such a report can be provided to a clinician such as an oncologist, who can use the information within the report to select a treatment and administer that treatment to the individual. For example, based on the report within GUI 1510 illustrated in FIG. 15K, an oncologist can select to administer the drug Crizonotib because the individual was determined to have a mutation in the ALK gene. However, if the report does not indicate an ALK mutation (or other mutation for which a treatment is specifically indicated), then the oncologist instead can select and administer a standard of care treatment that is not specific to a genetic mutation, but is based on conventional histopathology. Accordingly, the oncologist can use the contents of the report, e.g., an identification of gene mutations arising from genetic variants and an identification of a treatment for such mutation, to personalize the treatment of an individual for a disorder such as cancer or another disease.

Example 5

Additionally, as mentioned above, the present data structures can include data fields that store phenotypic information. In particular, for genomes that are associated with a disease phenotype, the data fields can include information that describes one or more phenotypic characteristics of the disease within that genome. For example, many different diagnostic tests can be used to determine the phenotype of an individual with a particular type of cancer, such as breast cancer. The present data structures can include data fields respectively storing some or all of the results of such diagnostic tests. Additionally, the present data structures further can include data fields respectively storing a description of any treatments that can have been administered to the individual whose genome it is, as well as a description of the individual's response to that treatment. Such information can be used to customize treatment plans for other individuals that can share variants with that genome as well as one or more phenotypic characteristics.

In one example, a user selected one or more genomes for analysis using GUI 1500 illustrated in FIG. 15A in the above-described manner, based upon which system 1400 generated an output such as illustrated in GUI 1501 of FIG. 15B-1. As illustrated in the upper region of GUI 1501, one of the available query terms is "TCGA Pheno," which permitted the user to customize a phenotypic query term based on nucleic information obtained from The Cancer Genome Atlas (TCGA), which as noted above is a repository of diverse genomic data types and alterations in them associated with genomes with a specific cancer type and clinical phenotype. FIG. 15L illustrates an exemplary GUI 1511 that a user used to limit variants by TCGA phenotype responsive to selection of the TCGA Pheno query term in GUI 1501. As can be seen in FIG. 15L, which listed TCGA phenotypic data associated with genomic data derived from patients with breast cancer (BRCA), the query term permitted the user to select from among numerous phenotypes, such as the presence or absence of a breast carcinoma progesterone receptor, an age at initial pathologic diagnosis, the race of the patient, and the like. Additional query terms then were applied based on the selected phenotypic query terms, e.g., the query terms illustrated in GUI 1511. If the genomes being analyzed had any genetic variants and phenotypic characteristics in common with another, the system further outputted (e.g., in the form of a report or a GUI) information regarding whether any of the individuals having those genomes responded positively to a treatment, and the identity of the treatment. If so, then a clinician could develop a therapeutic plan that included such a treatment.

INCORPORATION BY REFERENCE

Various references, such as patents, patent applications, and publications are cited herein, the disclosures of which are hereby incorporated by reference herein in their entireties.

Alternative Embodiments

It should be understood that the examples and code sections provided above are intended to be purely exemplary and not limiting of the present invention.

Additionally, it should be noted that the systems and methods can be implemented on various types of data processor environments (e.g., on one or more data processors) which execute instructions (e.g., software instructions) to perform operations disclosed herein. Non-limiting examples include implementation on a single general purpose computer or workstation, or on a networked system, or in a client-server configuration, or in an application service provider configuration. For example, the methods and systems described herein can be implemented on many different types of processing devices by program code comprising program instructions that are executable by the device processing subsystem. The software program instructions can include source code, object code, machine code, or any other stored data that is operable to cause a processing system to perform the methods and operations described herein. Other implementations can also be used, however, such as firmware or even appropriately designed hardware configured to carry out the methods and systems described herein. For example, a computer can be programmed with instructions to perform the various steps of the flowcharts shown in FIGS. 3, 7, and 10.

It is further noted that the systems and methods can include data signals conveyed via networks (e.g., local area network, wide area network, internet, combinations thereof, etc.), fiber optic medium, carrier waves, wireless networks, etc. for communication with one or more data processing devices. The data signals can carry any or all of the data disclosed herein that is provided to or from a device.

The systems' and methods' data (e.g., associations, mappings, data input, data output, intermediate data results, final data results, etc.) can be stored and implemented in one or more different types of computer-implemented data stores, such as different types of storage devices and programming constructs (e.g., RAM, ROM, Flash memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The systems and methods further can be provided on many different types of computer-readable storage media including computer storage mechanisms (e.g., non-transitory media, such as CD-ROM, diskette, RAM, flash memory, computer's hard drive, etc.) that contain instructions (e.g., software) for use in execution by a processor to perform the methods' operations and implement the systems described herein.

Moreover, the computer components, software modules, functions, data stores and data structures described herein can be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality can be located on a single computer or distributed across multiple computers depending upon the situation at hand.

It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and can be used interchangeably unless the context expressly dictates otherwise; the phrase "exclusive or" can be used to indicate situation where only the disjunctive meaning can apply.

While various illustrative embodiments of the invention are described above, it will be apparent to one skilled in the art that various changes and modifications can be made therein without departing from the invention. For example, although above-described embodiments have primarily focused on analyzing genetic variants that are associated with genomes, it should be understood that the systems, methods, and data structures provided herein can equally be applied to genomes based on deoxyribonucleic acid (DNA) or on ribonucleic acid (RNA), or for analyzing other types of variants, such as can occur in other types of biomolecules such as RNA or proteins. Additionally, it should be understood that the present systems, methods, and data structures suitably can be used to analyze the genomes of any desired species, including mammals such as humans, monkeys, and mice, insects such as *Drosophila*, bacteria such as *Saccharomyces cerevisiae*, or viruses. The appended claims are intended to cover all such changes and modifications that fall within the true spirit and scope of the invention.

What is claimed:

1. A computer-based method for analyzing genetic variants within a plurality of genomes, the method comprising:
submitting a query term to a database storing a plurality of discrete data structures within a memory, each data structure uniquely corresponding to only one of the genetic variants present within the plurality of genomes, each data structure comprising a first data field comprising a unique alphanumeric identifier for the corresponding genetic variant, a second data field comprising a unique alphanumeric identifier for a genome in which the corresponding genetic variant is present, and a third data field comprising an alphanumeric representation of a nucleic acid characteristic, the query term comprising a unique alphanumeric identifier for at least one genome of the plurality of genomes, an identification of a nucleic acid characteristic, and an operation to be performed on that genome;
searching the second and third data fields of the plurality of data structures stored in the database for unique alphanumeric identifiers that match the query term and satisfy the operation; and
generating an output representing the result of performing the search;
wherein the third data field is generated by:
obtaining a genome mask comprising a plurality of chromosome masks, each chromosome mask corresponding to a chromosome and comprising an array of bits, each bit corresponding to a base pair position in the corresponding chromosome, wherein only bits corresponding to a position of the nucleic acid characteristic include a flag;
determining whether a bit within the genome mask that corresponds to the chromosome and position of the corresponding genetic variant includes a flag; and
if the bit is determined to include a flag, submitting a query to the curated data source information about the nucleic acid characteristic at the chromosome and position corresponding to that bit, and storing the query result in the third data field.

2. A computer-based system for analyzing genetic variants within a plurality of genomes, the system comprising:
a processor; and
a memory in operable communication with the processor, the memory storing a query module configured to cause the processor to submit a query term to a database storing a plurality of data structures, each data structure uniquely corresponding to only one of the genetic variants present within the plurality of genomes, each data structure comprising a first data field comprising a unique alphanumeric identifier for the corresponding genetic variant, a second data field comprising a unique alphanumeric identifier for a genome in which the corresponding genetic variant is present, and a third data field comprising an alphanumeric representation of a nucleic acid characteristic, the query term comprising a unique alphanumeric identifier for at least one genome of the plurality of genomes, an identification of a nucleic acid characteristic, and an operation to be performed on that genome, the query module further being configured to cause the processor to search the data fields of the plurality of data structures stored in the database for unique alphanumeric identifiers that match the query term and satisfy the operation, the query module further being configured to cause the processor to generate an output representing the result of performing the search;

wherein the third data field is generated by:
  obtaining a genome mask comprising a plurality of chromosome masks, each chromosome mask corresponding to a chromosome and comprising an array of bits, each bit corresponding to a base pair position in the corresponding chromosome, wherein only bits corresponding to a position of the nucleic acid characteristic include a flag;
  determining whether a bit within the genome mask that corresponds to the chromosome and position of the corresponding genetic variant includes a flag; and
  if the bit is determined to include a flag, submitting a query to the curated data source information about the nucleic acid characteristic at the chromosome and position corresponding to that bit, and storing the query result in the third data field.

3. A computer-based method for generating a database for use in analyzing genetic variants, the method being implemented by one or more computers and comprising:
  converting a digital representation of genetic variants within a first genome into a plurality of discrete data structures, each data structure uniquely corresponding to only one of the genetic variants present in the first genome, each data structure comprising a first data field comprising a unique alphanumeric identifier for the corresponding variant and a second data field comprising a unique alphanumeric identifier for the first genome;
  storing the plurality of discrete data structures in a database in a memory; and
  generating within at least one of the discrete data structures a third data field storing an alphanumeric representation of a nucleic acid characteristic, the generating comprising:
    obtaining a genome mask comprising a plurality of chromosome masks, each chromosome mask corresponding to a chromosome and comprising an array of bits, each bit corresponding to a base pair position in the corresponding chromosome, wherein only bits corresponding to a position of the nucleic acid characteristic include a flag;
    determining whether a bit within the genome mask that corresponds to the chromosome and position of the corresponding genetic variant includes a flag; and
    if the bit is determined to include a flag, submitting a query to the curated data source information about the nucleic acid characteristic at the chromosome and position corresponding to that bit, and storing the query result in the third data field.

4. The method of claim 3, wherein said digital representation of the genetic variants within the first genome comprises alphanumeric fields respectively describing a chromosome, a position along that chromosome, a reference allele, and a variant allele corresponding to each genetic variant, and
  wherein said converting comprises generating the unique alphanumeric identifier for that genetic variant based on the alphanumeric fields respectively describing the position, chromosome, reference allele, and variant allele for that genetic variant.

5. The method of claim 4, wherein the unique alphanumeric identifier is generated by hashing or concatenating the alphanumeric identifiers for the chromosome, position, reference allele, and variant allele for that genetic variant.

6. The method of claim 4, further comprising generating within each discrete data structure a plurality of additional data fields respectively storing the alphanumeric identifiers for the chromosome, position, reference allele, and variant allele of that genetic variant.

7. The method of claim 3, wherein the digital representation of the first genome is a variant call format (VCF) file, a genome variation format (GVF) file, a general feature format (GFF) file, a general transfer format (GTF) file, a sequence alignment data (SAM) file, a binary sequence alignment data (BAM) file, a BED file, a FASTA file, or a FASTQ file.

8. The method of claim 3, wherein obtaining each chromosome mask comprises:
  generating an array of bits, each bit corresponding to a base pair position in the corresponding chromosome; and
  for each bit:
    submitting a query to the curated data source requesting a response of whether the corresponding chromosome includes the nucleic acid characteristic at the position corresponding to that bit;
    flagging the bit if the curated data source responds that the corresponding chromosome does include the nucleic acid characteristic at the position corresponding to that bit; and
    not flagging the bit if the curated data source responds that the corresponding chromosome does not include the nucleic acid characteristic at the position corresponding to that bit.

9. The method of claim 8, wherein flagging the bit comprises setting the bit to "1," and wherein not flagging the bit comprises setting the bit to "0".

10. The method of claim 3, wherein generating the array of bits comprises generating an array of M integers each having length N, wherein M×N≥L, where L is a number of base pairs in the corresponding chromosome.

11. The method of claim 3, wherein the nucleic acid characteristic is selected from the group consisting of: a gene-based characteristic, a nucleotide-based characteristic, a score-based characteristic, a genome-based characteristic, and a sample-specific characteristic.

12. The method of claim 11, wherein the gene-based characteristic is selected from the group consisting of: a name or identifier of a gene in which the corresponding genetic variant is present, a biochemical pathway in which the genetic variant or a gene in which it is present is known to participate, an indication of whether the corresponding genetic variant is listed in a curated data source, a cancer type in which the corresponding genetic variant or a gene in which it is present is involved, a disease phenotype in which the corresponding genetic variant or a gene in which it is present is involved, a gene that is known to be expressed that contains the genetic variant, a dbSNP associated with the corresponding genetic variant, and a transcription factor that is at least partially encoded by the genetic variant.

13. The method of claim 11, wherein the nucleotide-based characteristic is an indication of methylation, is an alphanumeric description of a genomic location in which the corresponding genetic variant is present, the genomic location selected from the group consisting of: an exon, an intron, a regulatory region, a splice site, a flanking region, a promoter region, and a region that codes for non-coding RNA, or is an alphanumeric description of a type of the corresponding genetic variant selected from the group consisting of: missense, nonsense, synonymous, insertion, deletion, and structural variation.

14. The method of claim 11, wherein the score-based characteristic is selected from the group consisting of: an allele frequency associated with the corresponding genetic variant, a SIFT score associated with the corresponding genetic variant, a PolyPhen-2 score associated with the corresponding genetic variant, a PolyPhen score associated with the corresponding genetic variant, and a PFAM associated with the corresponding genetic variant.

15. The method of claim 11, wherein the genome-based characteristic is selected from the group consisting of: a zygosity of the genome in which the corresponding genetic variant is present, a fractional allele frequency for the corresponding genetic variant in the genome in which the corresponding genetic variant is present, a phenotype of the genome in which the corresponding genetic variant is present, a demographic of the genome in which the corresponding genetic variant is present, and a clinical indication of the genome in which the corresponding genetic variant is present.

16. The method of claim 11, wherein the sample-specific characteristic is selected from the group consisting of: a read quality of the genome in which the corresponding genetic variant is present, and a read depth of the genome in which the corresponding genetic variant is present.

17. The method of claim 3, further comprising obtaining digital representations of genetic variants within a plurality of additional genomes, and for each genetic variant within each additional genome:
   determining whether that genetic variant corresponds to a discrete data structure stored within the database;
   if that genetic variant is determined to correspond to a stored discrete data structure, modifying the corresponding stored discrete data structure to include a third data field comprising a unique alphanumeric identifier for the first genome, and storing the modified discrete data structure within the database; and
   if that genetic variant is determined not to correspond to a stored discrete data structure, converting the digital representation of that genetic variant into an additional discrete data structure uniquely corresponding to only that genetic variant, the additional discrete data structure comprising a first data field comprising a unique alphanumeric identifier for the corresponding genetic variant and a second data field comprising a unique alphanumeric identifier for the first genome, and storing the additional discrete data structure within the database.

18. The method of claim 17, wherein determining whether that genetic variant corresponds to a stored discrete data structure comprises:
   generating a unique alphanumeric identifier for that genetic variant; and
   searching the first data fields of the existing discrete data structures stored within the database for a unique alphanumeric identifier that matches the unique alphanumeric identifier for that genetic variant.

19. The method of claim 17, wherein the resulting plurality of discrete data structures includes at least 10 million discrete data structures.

20. The method of claim 3, wherein the method is performed using a personal computer.

21. The method of claim 20, wherein the method is performed in random access memory (RAM) of the personal computer.

22. A computer-based system for generating a database for use in analyzing genetic variants, the system comprising:
   a processor; and
   a memory in operable communication with the processor, the memory storing a data structure module configured to cause the processor to receive a digital representation of genetic variants within a first genome, and for each genetic variant within the digital representation:
   to convert the digital representation of that genetic variant within a discrete data structure uniquely corresponding to only that genetic variant, the data structure comprising a first data field comprising a unique alphanumeric identifier for the corresponding variant and a second data field comprising a unique alphanumeric identifier for the first genome;
   to store the discrete data structure in a database in a memory; and
   to generate within at least one of the discrete data structures a third data field storing an alphanumeric representation of a nucleic acid characteristic, the generating comprising:
   obtaining a genome mask comprising a plurality of chromosome masks, each chromosome mask corresponding to a chromosome and comprising an array of bits, each bit corresponding to a base pair position in the corresponding chromosome, wherein only bits corresponding to a position of the nucleic acid characteristic include a flag;
   determining whether a bit within the genome mask that corresponds to the chromosome and position of the corresponding genetic variant includes a flag; and
   if the bit is determined to include a flag, submitting a query to the curated data source information about the nucleic acid characteristic at the chromosome and position corresponding to that bit, and storing the query result in the third data field.

* * * * *

SEQUENCE LISTING

```
<160> NUMBER OF SEQ ID NOS: 9

<210> SEQ ID NO 1
<211> LENGTH: 22
<212> TYPE: DNA
<213> ORGANISM: Artificial Sequence
<220> FEATURE:
<223> OTHER INFORMATION: made up sequence on Chromosome 1, genome 1 for
      illustrative purpose (see FIG. 1A)

<400> SEQUENCE: 1
ctagataggc taagaaaaca tc                                              22

<210> SEQ ID NO 2
<211> LENGTH: 22
<212> TYPE: DNA
<213> ORGANISM: Artificial Sequence
<220> FEATURE:
<223> OTHER INFORMATION: made up sequence on Chromosome 2, genome 1 for
      illustrative purpose (see FIG. 1A)

<400> SEQUENCE: 2
ctagctaggc taagaaaaca tc                                              22

<210> SEQ ID NO 3
<211> LENGTH: 22
<212> TYPE: DNA
<213> ORGANISM: Artificial Sequence
<220> FEATURE:
<223> OTHER INFORMATION: made up sequence on Chromosome 1, reference
      genome for illustrative purpose (see FIG. 1A)

<400> SEQUENCE: 3
ctagataggc taagaaaacc at                                              22

<210> SEQ ID NO 4
<211> LENGTH: 22
<212> TYPE: DNA
<213> ORGANISM: Artificial Sequence
<220> FEATURE:
<223> OTHER INFORMATION: made up sequence on Chromosome 1, genome 1 for
      illustrative purpose (see FIG. 4A)

<400> SEQUENCE: 4
ctagataggc taagaaaaca tc                                              22

<210> SEQ ID NO 5
<211> LENGTH: 22
<212> TYPE: DNA
<213> ORGANISM: Artificial Sequence
<220> FEATURE:
<223> OTHER INFORMATION: made up sequence on Chromosome 2, genome 1 for
      illustrative purpose (see FIG. 4A)

<400> SEQUENCE: 5
actgataaac gatcccttc ta                                               22

<210> SEQ ID NO 6
<211> LENGTH: 22
<212> TYPE: DNA
```

```
<213> ORGANISM: Artificial Sequence
<220> FEATURE:
<223> OTHER INFORMATION: made up sequence on Chromosome X, genome 1 for
      illustrative purpose (see FIG. 4A)

<400> SEQUENCE: 6
taggcccatt gacaatgcga ga                                              22

<210> SEQ ID NO 7
<211> LENGTH: 22
<212> TYPE: DNA
<213> ORGANISM: Artificial Sequence
<220> FEATURE:
<223> OTHER INFORMATION: made up sequence on Chromosome 1, genome N for
      illustrative purpose (see FIG. 4A)

<400> SEQUENCE: 7
ctagctaggc taagaaaaca tc                                              22

<210> SEQ ID NO 8
<211> LENGTH: 23
<212> TYPE: DNA
<213> ORGANISM: Artificial Sequence
<220> FEATURE:
<223> OTHER INFORMATION: made up sequence on Chromosome 2, genome N for
      illustrative purpose (see FIG. 4A)

<400> SEQUENCE: 8
actgataaaa cgatcccctt cta                                             23

<210> SEQ ID NO 9
<211> LENGTH: 22
<212> TYPE: DNA
<213> ORGANISM: Artificial Sequence
<220> FEATURE:
<223> OTHER INFORMATION: made up sequence on Chromosome X, genome N for
      illustrative purpose (see FIG. 4A)

<400> SEQUENCE: 9
taggcccatt gagaatgcga ga                                              22
```